United States Patent
Zeghouf et al.

(10) Patent No.: US 12,152,012 B2
(45) Date of Patent: Nov. 26, 2024

(54) BRAG2 INHIBITORS AND APPLICATIONS THEREOF

(71) Applicant: CENTRE NATIONAL DE LA RECHERCHE SCIENTIFIQUE, Paris (FR)

(72) Inventors: Mahel Zeghouf, Palaiseau (FR); Raphaël Rodriguez, Paris (FR); Jacqueline Cherfils, Gif sur Yvette (FR); Agata Nawrotek, Saint-Remy les Chevreuse (FR); Sarah Benabdi, Paris (FR); Supaporn Niyomchon, Paris (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 918 days.

(21) Appl. No.: 17/260,630

(22) PCT Filed: Jul. 16, 2019

(86) PCT No.: PCT/EP2019/069142
§ 371 (c)(1),
(2) Date: Jan. 15, 2021

(87) PCT Pub. No.: WO2020/016239
PCT Pub. Date: Jan. 23, 2020

(65) Prior Publication Data
US 2021/0284620 A1   Sep. 16, 2021

(30) Foreign Application Priority Data
Jul. 16, 2018  (EP) ..................................... 18305962

(51) Int. Cl.
*C07D 311/22* (2006.01)
*A61K 45/06* (2006.01)
(Continued)

(52) U.S. Cl.
CPC ............ *C07D 311/22* (2013.01); *A61P 35/00* (2018.01); *A61K 45/06* (2013.01)

(58) Field of Classification Search
CPC ........ C07D 311/22; A61P 35/00; A61P 25/00; A61K 45/06; A61K 31/352
See application file for complete search history.

(56) References Cited

U.S. PATENT DOCUMENTS 6,518,301 B1   2/2003  Barlaam et al.
2015/0322033 A1  11/2015  Hiramatsu et al.

FOREIGN PATENT DOCUMENTS

JP   2002542187 A   12/2002
JP   2007097421 A    4/2007
(Continued)

OTHER PUBLICATIONS

One-pot synthesis of functionalized benzo[c]coumarins and their precursors via the reaction of 2-(polyfluoroalkyl)chromones with 4-alkyl-3-cyanocoumarins, RSC Adv., 6, pp. 58188-58202 by Sosnovskikh et al. (Year: 2016).*

(Continued)

*Primary Examiner* — Jeffrey S Lundgren
*Assistant Examiner* — Alexander K. Showalter
(74) *Attorney, Agent, or Firm* — WC&F IP

(57) ABSTRACT

The present invention relates to molecules having the following chemical structure (I). The present invention concerns molecules, in particular active as BRAG2 inhibitors and applications thereof. In particular, the invention concerns BRAG2 inhibitors in the treatment of a cancer or angiogenesis.

Figure 1:
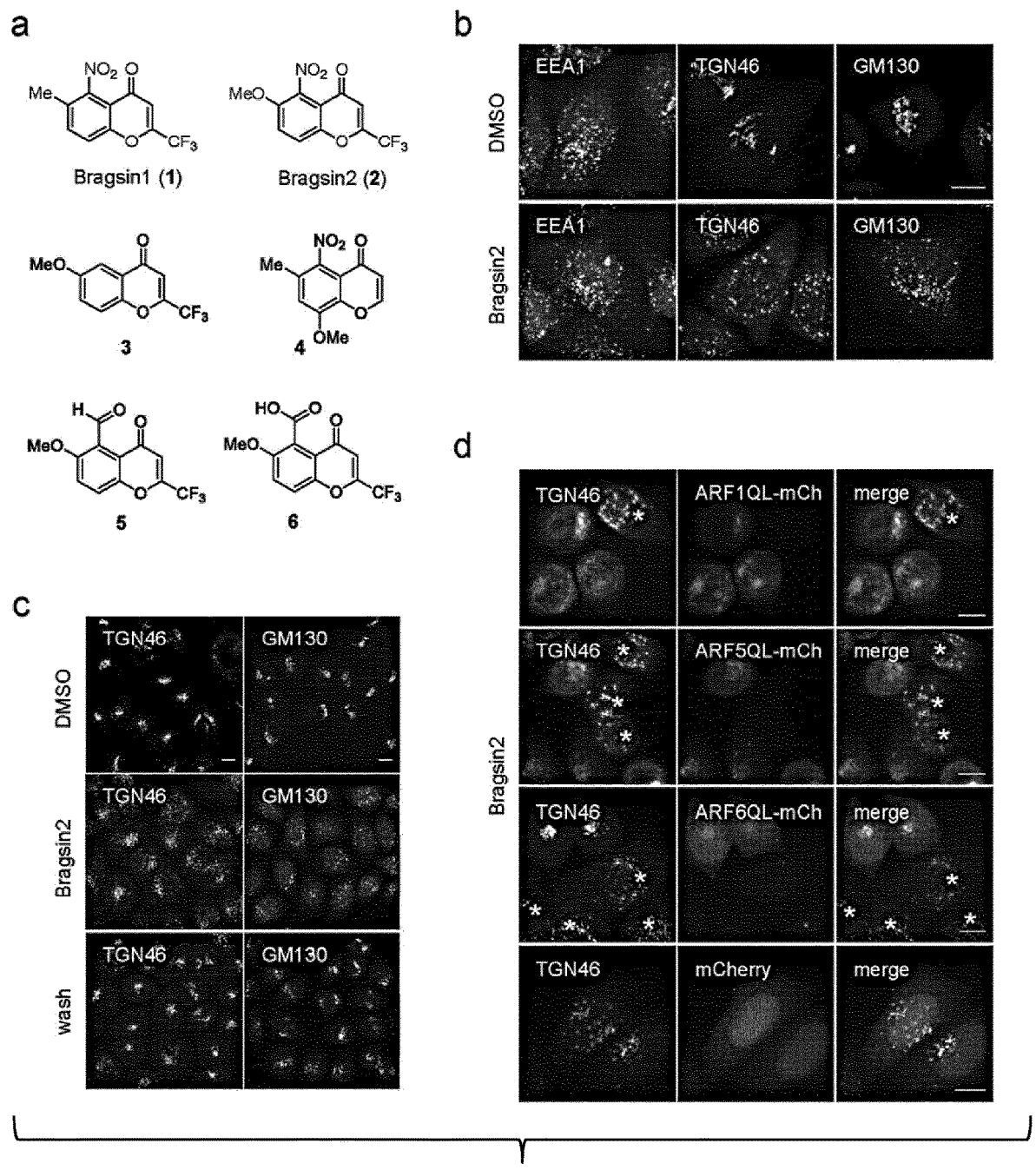

15 Claims, 27 Drawing Sheets
Specification includes a Sequence Listing.

(51) Int. Cl.
  *A61P 35/00* (2006.01)
  *A61K 31/352* (2006.01)
  *A61P 25/00* (2006.01)

(56) References Cited

FOREIGN PATENT DOCUMENTS

WO 2009026657 A1 3/2009
WO 2012170371 A1 12/2012

OTHER PUBLICATIONS

Antagonism of human formyl peptide receptor 1 (FPR1) by chromones and related isoflavones, Biochem. Pharmacol., 92, pp. 627-641 by Schepetkin et al. (Year: 2014).*
Principles of early drug discovery, Br. J. Pharmacol., 162, pp. 1239-1249 by Hughes et al. (Year: 2011).*
New development in studies of formyl-peptide receptors: critical roles in host defense, J. Leukoc. Biol., 99, pp. 425-435 by Li et al. (Year: 2015).*
ARF-GEP100, a guanine nucleotide-exchange protein for ADP-ribosylation factor 6, P.N.A.S., 98, pp. 2413-2418 by Someya et al. (Year: 2001).*
Angiogenesis, Chapter 1: Overview of Angiogenesis, Morgan & Claypoool Life Sciences by Adair et al. (Year: 2010).*
Schepetkin et al., Antagonism of human formyl peptide receptor 1 (FPR1) by chromones and related isoflavones, Biochem. Pharmacol., 92, pp. 627-641 (Year: 2014).*
Sosnovskikh et al., One-pot synthesis of functionalized benzo[c-]coumarins and their precursors via the reaction of 2-(polyfluoroalkyl)chromones with 4-alkyl-3-cyanocoumarins, RSC Adv., 6, pp. 58188-58202 (Year: 2016).*
Zhu, W. et al., "Small GTPase ARF6 controls VEGFR2 trafficking and signaling in diabetic retinopathy", J Clin Invest. 2017;127(12):4569-4582. https://doi.org/10.1172/JCI91770.
Ginistier, C. et al., "ALDH1 Is a Marker of Normal and Malignant Human Mammary Stem Cells and a Predictor of Poor Clinical Outcome", Stem Cell 1, 2007.
Adams, P. et al., "PHENIX: a comprehensive Python-based system for macromolecular structure solution", Acta Crystallogica D66, 2010.
Benabdi, S. et al., "Family-wide Analysis of the Inhibition of Arf Guanine Nucleotide Exchange Factors with Small Molecules: Evidence of Unique Inhibitory Profiles", Biochemistry 56, 2017.
Aizel, K. et al., "Integrated Conformational and Lipid-Sensing Regulation of Endosomal ArfGEF BRAG2", PLOS Biology 11:9, 2013.
Cheng, T. et al., "Formyl Peptide Receptor 1 Expression Is Associated with Tumor Progression and Survival in Gastric Cancer", Anticancer Research 34, 2014.
Bondarenko, S. et al., "Synthesis of Analogs of Natural Isoflavonoids Containing Phloroglucinol", Chemistry of Natural Compounds 39:3, 2003.
Blanc, E. et al., "Refinement of severely incomplete structures with maximum likelihood in BUSTER±TNT", Acta Crystallographica D60, 2004.
CharafeJauffret, E. et al., "ALDH1-Positive Cancer Stem Cells Predict Engraftment of Primary Breast Tumors and Are Governed by a Common Stem Cell Program", Cancer Research 73:24, 2013.
D'Souza, R. and Casanova, J., "The BRAG/IQSec family of Arf GEFs", SMALL GTPASES 7:4, 2016.
Das, S. et al., "Structural Organization and Dynamics of Homodimeric Cytohesin Family Arf GTPase Exchange Factors in Solution and on Membranes", Structure 27:12, 2009.
XP-002788245.
DiNitto, J. et al., "Structural Basis and Mechanism of Autoregulation in 3-Phosphoinositide-Dependent Grp1 Family Arf GTPase Exchange Factors" Molecular Cell 28, 2007.
XP-002788246.

Gaspar, A. et al., "Chromone: A Valid Scaffold in Medicinal Chemistry", Chemical Reviews 114, 2014.
Emsley, P. and Cowtan, K., "Coot: model-building tools for molecular graphics", Acta Crystallographica D60, 2004.
Menju, T. et al., "Engagement of Overexpressed Her2 with GEP100 Induces Autonomous Invasive Activities and Provides a Biomarker for Metastases of Lung Adenocarcinoma", PLOS One 6:9, 2011.
Hashimoto, A. et al., "GEP100-Arf6-AMAP1-Cortactin Pathway Frequently Used in Cancer Invasion Is Activated by VEGFR2 to Promote Angiogenesis", PLOS One 6:8, 2011.
Hu, Z. et al., "GEP100 regulates epidermal growth factor-induced MDA-MB-231 breast cancer cell invasion through the activation of Arf6/ERK/uPAR signaling pathway", Experimental Cell Research 319, 2013.
Horton, D. et al., "The Combinatorial Synthesis of Bicyclic Privileged Structures or Privileged Substructures", Chem. Rev. 103, 2003.
Jian, X. et al., "The Pleckstrin Homology (PH) Domain of the Arf Exchange Factor Brag2 Is an Allosteric Binding Site*", The Journal of Biological Chemistry 287:9, 2012.
Hu, Z. et al., "GEP100/Arf6 Is Required for Epidermal Growth Factor-Induced ERK/Rac1 Signaling and Cell Migration in Human Hepatoma HepG2 Cells", PLOS One 7:6, 2012.
Karandur, D. et al., "Multiple interactions between an Arf/GEF complex and charged lipids determine activation kinetics on the membrane", PNAS 114:43, 2017.
Khilya, V. et al., "Synthesis and Properties of Heterocyclic Analogs of Isoflavones", Khimiya Geterotsiklicheskikh Soedinenii, 1973.
Kharrat, S. et al., "Synthesis of 3-Trifluoromethyl- and 3-Perfluoroalkyl-Substituted 3-Aryloxyand 3-Heteroaryloxypropenoic Acids and of the Cyclization Products, 2-Trifluoromethyl- and 2-Perfluoroalkyl-4H-chromen-4-ones", Synthesis 22, 2007.
Lemmon, M., "Membrane recognition by phospholipid-binding domains", Molecular Cell Biology 9, 2008.
Manavski, F. et al., "Brag2 differentially regulates β1- and β3-integrin-dependent adhesion in endothelial cells and is involved in developmental and pathological angiogenesis", Basic Res Cardiol 109:44, 2014.
McCoy, A. et al., "Phaser crystallographic software", Journal of Applied Crystallography 40, 2007.
Matsumoto, Y. et al., "Inhibition of epithelial-mesenchymal transition by cetuximab via the EGFR-GEP100-Arf6-AMAP1 pathway in head and neck cancer", Head & Neck, 2017.
Sosnovskikh, V. et al., "One-Pot Domino Synthesis of Polyfunctionalized Benzoxanthones, Dihydroxanthones, and m-Terphenyls from 2-(Polyfluoroalkyl)chromones", Eur. J. Org. Chem., 2015.
Nastou, K. et al., "The Human Plasma Membrane Peripherome: Visualization and Analysis of Interactions", BioMed Research International, 2014.
Parmar, V. et al., "Anti-invasive Activity of Alkaloids and Polyphenolics in Vitro", Bioorganic & Medicinal Chemistry 5:8, 1997.
Morishige, M. et al., "GEP100 links epidermal growth factor receptor signalling to ARF6 activation to induce breast cancer invasion", Nature Cell Biology 10:1, 2008.
Peurois, F. et al., "Characterization of the activation of small GTPases by their GEFs on membranes using artificial membrane tethering", Biochemical Journal 474, 2017.
Sosnovskikh, V. & Usachev, B., "2-Polyfluroalkylchromones", Russian Chemical Bulletin, International Edition 50:3, 2001.
Sosnovskikh, V. et al., "Ite gioselective Nucleophilic I,4-Trifluoromethylation of 2-Polyfluoroalkylchromones with (Trifluoromethyl)trimethylsilane. Synthesis of Fluorinated Analogs of Natural 2,2-Dimethylchroman-4-ones and 2,2-Dimethylchromenes", J. Org. Chem. 68, 2003.
Sosnovskikh, V. & Usachev, B., "2Polyf luoroalkylchromones 13.* Synthesis and nitration of 6,8dibromo2trifluoromethylchromone", Russian Chemical Bulletin, International Edition 51:10, 2002.
Shoubridge, C. et al., "Mutations in the guanine nucleotide exchange factor gene IQSEC2 cause nonsyndromic intellectual disability", Nat Genet. 42:6, 2010.

(56) References Cited

OTHER PUBLICATIONS

Sakurai, A. et al., "Phosphatidylinositol-4-phosphate 5-Kinase and GEP100/Brag2 Protein Mediate Antiangiogenic Signaling by Semaphorin 3E-Plexin-D1 through Arf6 Protein*", The Journal of Biological Chemistry 286:39.
Schindelin, J. et al., "Fiji—an Open Source platform for biological image analysis", Nature Methods 9:7, 2012.
Schepetkin, I. et al., "Antagonism of human formyl peptide receptor 1 (FPR1) by chromones and related isoflavones", Biochemical Pharmacology 92, 2014.
Sabe, H. et al., "The EGFR-GEP100-Arf6-AMAP1 Signaling Pathway Specific to Breast Cancer Invasion and Metastasis†", Traffic 10, 2009.
UniprotKB-Q6DN90.
Tamura, K. et al., "Synthesis of 2-polyfluoroalkylated thiochromones and chromones", Journal of Fluorine Chemistry 68, 1994.
Viaud, J. et al., "Structure-based discovery of an inhibitor of Arf activation by Sec7 domains through targeting of protein-protein complexes", PNAS 104:25, 2007.
Wang, L. et al., "Synthesis, Crystal Structure, and Biological Evaluation of a Series of Phloretin Derivatives", Molecules 19, 2014.
Vonrheim, C. et al., "Data processing and analysis with the autoPROC toolbox", Acta Crystallographica D67, 2011.
Wall, M. et al., "Antimutagenic Agents From Natural Products1", Journal of Natural Products 55:11, 1992.
Xie, X. et al., "Down-Regulation of GEP100 Causes Increase in ECadherin Levels and Inhibits Pancreatic Cancer Cell Invasion", PloS ONE 7:5, 2012.
Yoo, J. et al., "ARF6 Is an Actionable Node that Orchestrates Oncogenic GNAQ Signaling in Uveal Melanoma", Cancer Cell 29, 2016.

* cited by examiner a b c a b

SEQUENCE LISTING

<160> NUMBER OF SEQ ID NOS: 10

<210> SEQ ID NO 1
<211> LENGTH: 963
<212> TYPE: PRT
<213> ORGANISM: Homo sapiens
<220> FEATURE:
<223> OTHER INFORMATION: IQ motif and SEC7 domain-containing protein 1

<400> SEQUENCE: 1

```
Met Trp Cys Leu His Cys Asn Ser Glu Arg Thr Gln Ser Leu Leu Glu
1               5                   10                  15

Leu Glu Leu Asp Ser Gly Val Glu Gly Glu Ala Pro Ser Ser Glu Thr
            20                  25                  30

Gly Thr Ser Leu Asp Ser Pro Ser Ala Tyr Pro Gln Gly Pro Leu Val
        35                  40                  45

Pro Gly Ser Ser Leu Ser Pro Asp His Tyr Glu His Thr Ser Val Gly
50                  55                  60

Ala Tyr Gly Leu Tyr Ser Gly Pro Pro Gly Gln Gln Gln Arg Thr Arg
65                  70                  75                  80

Arg Pro Lys Leu Gln His Ser Thr Ser Ile Leu Arg Lys Gln Ala Glu
                85                  90                  95

Glu Glu Ala Ile Lys Arg Ser Arg Ser Leu Ser Glu Ser Tyr Glu Leu
            100                 105                 110

Ser Ser Asp Leu Gln Asp Lys Gln Val Glu Met Leu Glu Arg Lys Tyr
        115                 120                 125

Gly Gly Arg Leu Val Thr Arg His Ala Ala Arg Thr Ile Gln Thr Ala
    130                 135                 140

Phe Arg Gln Tyr Gln Met Asn Lys Asn Phe Glu Arg Leu Arg Ser Ser
145                 150                 155                 160

Met Ser Glu Asn Arg Met Ser Arg Arg Ile Val Leu Ser Asn Met Arg
                165                 170                 175

Met Gln Phe Ser Phe Glu Gly Pro Glu Lys Val His Ser Ser Tyr Phe
            180                 185                 190

Glu Gly Lys Gln Val Ser Val Thr Asn Asp Gly Ser Gln Leu Gly Ala
        195                 200                 205

Leu Val Ser Pro Glu Cys Gly Asp Leu Ser Glu Pro Thr Thr Leu Lys
    210                 215                 220

Ser Pro Ala Pro Ser Ser Asp Phe Ala Asp Ala Ile Thr Glu Leu Glu
225                 230                 235                 240

Asp Ala Phe Ser Arg Gln Val Lys Ser Leu Ala Glu Ser Ile Asp Asp
                245                 250                 255

Ala Leu Asn Cys Arg Ser Leu His Thr Glu Glu Ala Pro Ala Leu Asp
            260                 265                 270

Ala Ala Arg Ala Arg Asp Thr Glu Pro Gln Thr Ala Leu His Gly Met
        275                 280                 285

Asp His Arg Lys Leu Asp Glu Met Thr Ala Ser Tyr Ser Asp Val Thr
    290                 295                 300

Leu Tyr Ile Asp Glu Glu Leu Ser Pro Pro Leu Pro Leu Ser Gln
305                 310                 315                 320

Ala Gly Asp Arg Pro Ser Ser Thr Glu Ser Asp Leu Arg Leu Arg Ala
                325                 330                 335

Gly Gly Ala Ala Pro Asp Tyr Trp Ala Leu Ala His Lys Glu Asp Lys
            340                 345                 350

Ala Asp Thr Asp Thr Ser Cys Arg Ser Thr Pro Ser Leu Glu Arg Gln
```

```
            355                 360                 365
Glu Gln Arg Leu Arg Val Glu His Leu Pro Leu Leu Thr Ile Glu Pro
            370                 375                 380
Pro Ser Asp Ser Ser Val Asp Leu Ser Asp Arg Ser Glu Arg Gly Ser
385                 390                 395                 400
Leu Lys Arg Gln Ser Ala Tyr Glu Arg Ser Leu Gly Gly Gln Gln Gly
            405                 410                 415
Ser Pro Lys His Gly Pro His Ser Gly Ala Pro Lys Ser Leu Pro Arg
            420                 425                 430
Glu Glu Pro Glu Leu Arg Pro Arg Pro Arg Pro Leu Asp Ser His
            435                 440                 445
Leu Ala Ile Asn Gly Ser Ala Asn Arg Gln Ser Lys Ser Glu Ser Asp
    450                 455                 460
Tyr Ser Asp Gly Asp Asn Asp Ser Ile Asn Ser Thr Ser Asn Ser Asn
465                 470                 475                 480
Asp Thr Ile Asn Cys Ser Ser Glu Ser Ser Arg Asp Ser Leu Arg
            485                 490                 495
Glu Gln Thr Leu Ser Lys Gln Thr Tyr His Lys Glu Ala Arg Asn Ser
            500                 505                 510
Trp Asp Ser Pro Ala Phe Ser Asn Asp Val Ile Arg Lys Arg His Tyr
            515                 520                 525
Arg Ile Gly Leu Asn Leu Phe Asn Lys Lys Pro Glu Lys Gly Val Gln
            530                 535                 540
Tyr Leu Ile Glu Arg Gly Phe Val Pro Asp Thr Pro Val Gly Val Ala
545                 550                 555                 560
His Phe Leu Leu Gln Arg Lys Gly Leu Ser Arg Gln Met Ile Gly Glu
            565                 570                 575
Phe Leu Gly Asn Arg Gln Lys Gln Phe Asn Arg Asp Val Leu Asp Cys
            580                 585                 590
Val Val Asp Glu Met Asp Phe Ser Thr Met Glu Leu Asp Glu Ala Leu
            595                 600                 605
Arg Lys Phe Gln Ala His Ile Arg Val Gln Gly Glu Ala Gln Lys Val
625                 610                 615                 620
Glu Arg Leu Ile Glu Ala Phe Ser Gln Arg Tyr Cys Ile Cys Asn Pro
625                 630                 635                 640
Gly Val Val Arg Gln Phe Arg Asn Pro Asp Thr Ile Phe Ile Leu Ala
            645                 650                 655
Phe Ala Ile Ile Leu Leu Asn Thr Asp Met Tyr Ser Pro Asn Val Lys
            660                 665                 670
Pro Glu Arg Lys Met Lys Leu Glu Asp Phe Ile Lys Asn Leu Arg Gly
            675                 680                 685
Val Asp Asp Gly Glu Asp Ile Pro Arg Glu Met Leu Met Gly Ile Tyr
            690                 695                 700
Glu Arg Ile Arg Lys Arg Glu Leu Lys Thr Asn Glu Asp His Val Ser
705                 710                 715                 720
Gln Val Gln Lys Val Glu Lys Leu Ile Val Gly Lys Lys Pro Ile Gly
            725                 730                 735
Ser Leu His Pro Gly Leu Gly Cys Val Leu Ser Leu Pro His Arg Arg
            740                 745                 750
Leu Val Cys Tyr Cys Arg Leu Phe Glu Val Pro Asp Pro Asn Lys Pro
            755                 760                 765
Gln Lys Leu Gly Leu His Gln Arg Glu Ile Phe Leu Phe Asn Asp Leu
            770                 775                 780
```

Leu Val Val Thr Lys Ile Phe Gln Lys Lys Asn Ser Val Thr Tyr
785                 790                 795                 800

Ser Phe Arg Gln Ser Phe Ser Leu Tyr Gly Met Gln Val Leu Leu Phe
            805                 810                 815

Glu Asn Gln Tyr Tyr Pro Asn Gly Ile Arg Leu Thr Ser Ser Val Pro
        820                 825                 830

Gly Ala Asp Ile Lys Val Leu Ile Asn Phe Asn Ala Pro Asn Pro Gln
    835                 840                 845

Asp Arg Lys Lys Phe Thr Asp Asp Leu Arg Glu Ser Ile Ala Glu Val
850                 855                 860

Gln Glu Met Glu Lys His Arg Ile Glu Ser Leu Glu Lys Gln Lys
865                 870                 875                 880

Gly Val Val Arg Pro Ser Met Ser Gln Cys Ser Ser Leu Lys Lys Glu
            885                 890                 895

Ser Gly Asn Gly Thr Leu Ser Arg Ala Cys Leu Asp Asp Ser Tyr Ala
        900                 905                 910

Ser Gly Glu Gly Leu Lys Arg Ser Ala Leu Ser Ser Leu Arg Asp
        915                 920                 925

Leu Ser Glu Ala Gly Lys Arg Gly Arg Arg Ser Ser Ala Gly Ser Leu
    930                 935                 940

Glu Ser Asn Val Glu Phe Gln Pro Phe Glu Pro Leu Gln Pro Ser Val
945                 950                 955                 960

Leu Cys Ser

<210> SEQ ID NO 2
<211> LENGTH: 20
<212> TYPE: DNA
<213> ORGANISM: Unknown
<220> FEATURE:
<223> OTHER INFORMATION: BRAG2 primer1

<400> SEQUENCE: 2
cgtggcattt ctttggtgtc                                          20

<210> SEQ ID NO 3
<211> LENGTH: 20
<212> TYPE: DNA
<213> ORGANISM: Unknown
<220> FEATURE:
<223> OTHER INFORMATION: BRAG2 primer1

<400> SEQUENCE: 3
acccgagaat tgatgagtcg                                          20

<210> SEQ ID NO 4
<211> LENGTH: 20
<212> TYPE: DNA
<213> ORGANISM: Unknown
<220> FEATURE:
<223> OTHER INFORMATION: ARNO primer1

<400> SEQUENCE: 4
ttgtgtcaag gatagggctg                                          20

<210> SEQ ID NO 5
<211> LENGTH: 20
<212> TYPE: DNA
<213> ORGANISM: Unknown
<220> FEATURE:
<223> OTHER INFORMATION: ARNO primer2

```
<400> SEQUENCE: 5
acttcacctt catagaggcg                                              20

<210> SEQ ID NO 6
<211> LENGTH: 20
<212> TYPE: DNA
<213> ORGANISM: Unknown
<220> FEATURE:
<223> OTHER INFORMATION: GBF1 primer1

<400> SEQUENCE: 6
tgtcactctc tacctttgcg                                              20

<210> SEQ ID NO 7
<211> LENGTH: 20
<212> TYPE: DNA
<213> ORGANISM: Unknown
<220> FEATURE:
<223> OTHER INFORMATION: GBF1 primer2

<400> SEQUENCE: 7
aaatctccgc tgtgtccatc                                              20

<210> SEQ ID NO 8
<211> LENGTH: 21
<212> TYPE: DNA
<213> ORGANISM: Unknown
<220> FEATURE:
<223> OTHER INFORMATION: GAPDH primer1

<400> SEQUENCE: 8
acaagaggaa gagagagacc c                                            21

<210> SEQ ID NO 9
<211> LENGTH: 20
<212> TYPE: DNA
<213> ORGANISM: Unknown
<220> FEATURE:
<223> OTHER INFORMATION: GADPH primer2

<400> SEQUENCE: 9
tacatgacaa ggtgcggctc                                              20

<210> SEQ ID NO 10
<211> LENGTH: 1114
<212> TYPE: PRT
<213> ORGANISM: Unknown
<220> FEATURE:
<223> OTHER INFORMATION: BRAG2 isoform2

<400> SEQUENCE: 10

Met Ala Cys Arg Arg Arg Tyr Phe Val Glu Gly Glu Ala Pro Ser Ser
1               5                   10                  15

Glu Thr Gly Thr Ser Leu Asp Ser Pro Ser Ala Tyr Pro Gln Gly Pro
            20                  25                  30

Leu Val Pro Gly Ser Ser Leu Ser Pro Asp His Tyr Glu His Thr Ser
        35                  40                  45

Val Gly Ala Tyr Gly Leu Tyr Ser Gly Pro Pro Gly Gln Gln Gln Arg
    50                  55                  60

Thr Arg Arg Pro Lys Leu Gln His Ser Thr Ser Ile Leu Arg Lys Gln
65                  70                  75                  80

Ala Glu Glu Glu Ala Ile Lys Arg Ser Arg Ser Leu Ser Glu Ser Tyr
```

```
                85              90              95
Glu Leu Ser Ser Asp Leu Gln Asp Lys Gln Val Glu Met Leu Glu Arg
            100             105             110

Lys Tyr Gly Gly Arg Leu Val Thr Arg His Ala Ala Arg Thr Ile Gln
            115             120             125

Thr Ala Phe Arg Gln Tyr Gln Met Asn Lys Asn Phe Glu Arg Leu Arg
        130             135             140

Ser Ser Met Ser Glu Asn Arg Met Ser Arg Arg Ile Val Leu Ser Asn
145             150             155             160

Met Arg Met Gln Phe Ser Phe Glu Gly Pro Glu Lys Val His Ser Ser
                165             170             175

Tyr Phe Glu Gly Lys Gln Val Ser Val Thr Asn Asp Gly Ser Gln Leu
            180             185             190

Gly Ala Leu Val Ser Pro Glu Cys Gly Asp Leu Ser Glu Pro Thr Thr
            195             200             205

Leu Lys Ser Pro Ala Pro Ser Ser Asp Phe Ala Asp Ala Ile Thr Glu
        210             215             220

Leu Glu Asp Ala Phe Ser Arg Gln Val Lys Ser Leu Ala Glu Ser Ile
225             230             235             240

Asp Asp Ala Leu Asn Cys Arg Ser Leu His Thr Glu Glu Ala Pro Ala
                245             250             255

Leu Asp Ala Ala Arg Ala Arg Asp Thr Glu Pro Gln Thr Ala Leu His
            260             265             270

Gly Met Asp His Arg Lys Leu Asp Glu Met Thr Ala Ser Tyr Ser Asp
            275             280             285

Val Thr Leu Tyr Ile Asp Glu Glu Glu Leu Ser Pro Pro Leu Pro Leu
        290             295             300

Ser Gln Ala Gly Asp Arg Pro Ser Ser Thr Glu Ser Asp Leu Arg Leu
305             310             315             320

Arg Ala Gly Gly Ala Ala Pro Asp Tyr Trp Ala Leu Ala His Lys Glu
                325             330             335

Asp Lys Ala Asp Thr Asp Thr Ser Cys Arg Ser Thr Pro Ser Leu Glu
            340             345             350

Arg Gln Glu Gln Arg Leu Arg Val Glu His Leu Pro Leu Leu Thr Ile
            355             360             365

Glu Pro Pro Ser Asp Ser Ser Val Asp Leu Ser Asp Arg Ser Glu Arg
        370             375             380

Gly Ser Leu Lys Arg Gln Ser Ala Tyr Glu Arg Ser Leu Gly Gly Gln
385             390             395             400

Gln Gly Ser Pro Lys His Gly Pro His Ser Gly Ala Pro Lys Ser Leu
                405             410             415

Pro Arg Glu Glu Pro Glu Leu Arg Pro Arg Pro Arg Pro Leu Asp
            420             425             430

Ser His Leu Ala Ile Asn Gly Ser Ala Asn Arg Gln Ser Lys Ser Glu
            435             440             445

Ser Asp Tyr Ser Asp Gly Asp Asn Asp Ser Ile Asn Ser Thr Ser Asn
        450             455             460

Ser Asn Asp Thr Ile Asn Cys Ser Ser Glu Ser Ser Ser Arg Asp Ser
465             470             475             480

Leu Arg Glu Gln Thr Leu Ser Lys Gln Thr Tyr His Lys Glu Ala Arg
                485             490             495

Asn Ser Trp Asp Ser Pro Ala Phe Ser Asn Asp Val Ile Arg Lys Arg
            500             505             510
```

```
His Tyr Arg Ile Gly Leu Asn Leu Phe Asn Lys Lys Pro Glu Lys Gly
            515                 520                 525

Val Gln Tyr Leu Ile Glu Arg Gly Phe Val Pro Asp Thr Pro Val Gly
            530                 535                 540

Val Ala His Phe Leu Leu Gln Arg Lys Gly Leu Ser Arg Gln Met Ile
545                 550                 555                 560

Gly Glu Phe Leu Gly Asn Arg Gln Lys Gln Phe Asn Arg Asp Val Leu
                    565                 570                 575

Asp Cys Val Val Asp Glu Met Asp Phe Ser Thr Met Glu Leu Asp Glu
                580                 585                 590

Ala Leu Arg Lys Phe Gln Ala His Ile Arg Val Gln Gly Glu Ala Gln
            595                 600                 605

Lys Val Glu Arg Leu Ile Glu Ala Phe Ser Gln Arg Tyr Cys Ile Cys
            610                 615                 620

Asn Pro Gly Val Val Arg Gln Phe Arg Asn Pro Asp Thr Ile Phe Ile
625                 630                 635                 640

Leu Ala Phe Ala Ile Ile Leu Leu Asn Thr Asp Met Tyr Ser Pro Asn
                    645                 650                 655

Val Lys Pro Glu Arg Lys Met Lys Leu Glu Asp Phe Ile Lys Asn Leu
            660                 665                 670

Arg Gly Val Asp Asp Gly Glu Asp Ile Pro Arg Glu Met Leu Met Gly
            675                 680                 685

Ile Tyr Glu Arg Ile Arg Lys Arg Glu Leu Lys Thr Asn Glu Asp His
690                 695                 700

Val Ser Gln Val Gln Lys Val Glu Lys Leu Ile Val Gly Lys Lys Pro
705                 710                 715                 720

Ile Gly Ser Leu His Pro Gly Leu Gly Cys Val Leu Ser Leu Pro His
                725                 730                 735

Arg Arg Leu Val Cys Tyr Cys Arg Leu Phe Glu Val Pro Asp Pro Asn
                740                 745                 750

Lys Pro Gln Lys Leu Gly Leu His Gln Arg Glu Ile Phe Leu Phe Asn
            755                 760                 765

Asp Leu Leu Val Val Thr Lys Ile Phe Gln Lys Lys Lys Asn Ser Val
770                 775                 780

Thr Tyr Ser Phe Arg Gln Ser Phe Ser Leu Tyr Gly Met Gln Val Leu
785                 790                 795                 800

Leu Phe Glu Asn Gln Tyr Tyr Pro Asn Gly Ile Arg Leu Thr Ser Ser
                805                 810                 815

Val Pro Gly Ala Asp Ile Lys Val Leu Ile Asn Phe Asn Ala Pro Asn
                820                 825                 830

Pro Gln Asp Arg Lys Lys Phe Thr Asp Asp Leu Arg Glu Ser Ile Ala
            835                 840                 845

Glu Val Gln Glu Met Glu Lys His Arg Ile Glu Ser Glu Leu Glu Lys
            850                 855                 860

Gln Lys Gly Val Val Arg Pro Ser Met Ser Gln Cys Ser Ser Leu Lys
865                 870                 875                 880

Lys Glu Ser Gly Asn Gly Thr Leu Ser Arg Ala Cys Leu Asp Asp Ser
                885                 890                 895

Tyr Ala Ser Gly Glu Gly Leu Lys Arg Ser Ala Leu Ser Ser Ser Leu
                900                 905                 910

Arg Asp Leu Ser Glu Ala Gly Lys Arg Gly Arg Arg Ser Ser Ala Gly
            915                 920                 925
```

```
Ser Leu Glu Ser Asn Val Glu Gly Ser Ile Ile Ser Ser Pro His Met
    930             935             940
Arg Arg Arg Ala Thr Ser Thr Arg Glu Cys Pro Ser Arg Pro His Gln
945             950             955             960
Thr Met Pro Asn Ser Ser Ser Leu Leu Gly Ser Leu Phe Gly Ser Lys
            965             970             975
Arg Gly Lys Pro Pro Pro Gln Ala His Leu Pro Ser Ala Pro Ala Leu
            980             985             990
Pro Pro Pro His Pro Pro Val Val Leu Pro His Leu Gln His Ser Val
        995             1000            1005
Ala Gly His His Leu Gly Pro Pro Glu Gly Leu Pro Gln Ala Ala Met
    1010            1015            1020
His Gly His His Thr Gln Tyr Cys His Met Gln Asn Pro Pro Tyr
1025            1030            1035            1040
His His His His His His His Pro Pro Gln His Ile Gln His Ala His
            1045            1050            1055
Gln Tyr His His Gly Pro His Gly Gly His Pro Ala Tyr Gly Ala His
        1060            1065            1070
Ala His Gly His Pro Pro Leu Pro Ser Ala His Val Gly His Thr Val
    1075            1080            1085
His His His Gly Gln Pro Pro Ala Pro Pro Pro Thr Ser Ser Lys
    1090            1095            1100
Ala Lys Pro Ser Gly Ile Ser Thr Ile Val
1105            1110
```

BRAG2 INHIBITORS AND APPLICATIONS THEREOF

The present invention concerns molecules, in particular active as BRAG2 inhibitors and applications thereof.

In particular, the invention concerns BRAG2 inhibitors in the treatment of a cancer or angiogenesis.

PRIOR ART

Cells response to variations in their environment by assembling dynamic signalling complexes at the surface of membranes, which collect signals and transmit information. Such signalling platforms are often dysfunctional in disease, either because of mutations that affect their regulation or because they are appropriated by pathological pathways. Drugs modulating their activity are thus highly sought-after, but signalling nodes have remained challenging targets by conventional competitive inhibitors because of their structural flexibility, which commonly involves large conformational changes, their widespread protein-protein interfaces and their multiple protein-lipid interactions. Consequently, a current drug discovery challenge is to develop novel strategies that use the structural features of membrane-associated signalling complexes.

Small GTPases and their regulators belong to the category of peripheral membrane proteins involved in pathologies. Proteins of the large family of small GTPases are chief organizers of signalling platforms at the surface of membranes with crucial functions in signal transduction, cell motility, membrane traffic and the coordination between these pathways. Because of their importance in normal cell homeostasis, small GTPase functions are twisted or hijacked in diverse pathologies, such as cancer, cardiovascular diseases and bacterial or viral infections. Inhibiting their activities in pathological contexts is therefore a compelling, unmet need in drug discovery. Small GTPases regulation is highly complex as it combined a GDP/GTP switch and a cytosol/membrane cycle where the GTP-bound GTPase is attached to the membrane. Added to this, the output of GTPase signalling involves multiple activators (guanine nucleotide exchange factors or GEFs, which stimulate the GDP/GTP exchange), inhibitors (GTPase-activating proteins or GAPs, which accelerate GTP hydrolysis and GDIs, which wrap their lipidic anchor to solubilize them), and effectors, which collectively assemble signalling platforms. GEFs, GAPs and effectors are themselves highly regulated through structural rearrangements and protein-membrane interactions. To date, some strategies inhibit the membrane/cytosol cycle by targeting either enzymes involved in the anchoring of their lipid post-translational modification or GDIs. Yet, inhibitors that directly target the regulatory protein-membrane interactions have never been described.

Peripheral membrane proteins coordinate cell responses to signals coming from their environment and are hence involved in numerous diseases. Despite their significance, they have remained elusive targets for conventional competitive inhibitors and alternate approaches are highly needed.

Aims of the Invention

The present invention aims to solve the technical problem of providing a BRAG2 inhibitor and applications thereof.

The present invention aims to solve the technical problem of providing new route for the treatment of a cancer or angiogenesis.

More particularly, the present invention aims to solve the technical problem of providing new route for the treatment of a cancer or angiogenesis by a BRAG2 inhibitor.

The present invention also aims to solve the technical problem of providing a molecule binding a protein-membrane interface.

DETAILED DESCRIPTION

The present invention solves at least one and preferably all technical problem set forth in the present invention.

In particular, the present invention relates to molecules having the following chemical structure (I) or a pharmaceutically acceptable salt thereof or a prodrug thereof, for use in a method of therapeutic treatment:

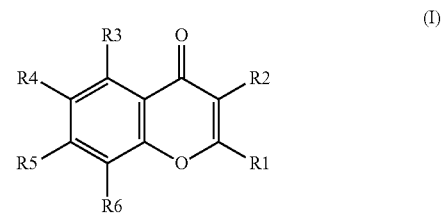

(I)

wherein:
- R1 is a fluorinated alkyl, preferably CF3;
- R3 is a chemical group comprising at least one oxygen and/or a nitrogen;
- R2, R4, R5 and R6 are independently atoms or groups of atoms.

The invention also relates to molecules having the following chemical structure (I):

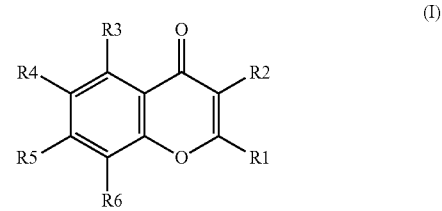

(I)

wherein:
- R1 is a fluorinated alkyl, preferably CF3;
- R3 is a chemical group comprising at least one oxygen and/or a nitrogen;
- R6 is an atoms or group of atoms different than hydrogen;
- R2, R4, R5 and are independently atoms or groups of atoms.

In particular, the present invention relates to a BRAG2 inhibitor having a structure of a molecule as defined in the present invention.

BRAG2 designates the protein Brefeldin-resistant Arf-GEF 2 protein (SEQ ID NO:1) (IQ motif and SEC7 domain-containing protein 1, i.e. see UniProtKB-Q6DN90 (IQEC1_HUMAN)-SEQ ID NO:1). This protein is also designated as ADP-ribosylation factors guanine nucleotide-exchange protein 100 or ADP-ribosylation factors guanine nucleotide-exchange protein 2. Another isoform of BRAG2 exists, referenced as UniProtKB-A0A087WWK8 (SEQ ID NO:10). This isoform shares a high sequence identity (same PH domain), but differs mainly by a longer N-terminus. Inhibitors of BRAG2 of the present invention inhibiting BRAG2 (Q6DN90) are considered to inhibit also this isoform (A0A087WWK8) as they bind to PH domain.

In particular the invention relates to non-competitive inhibition of its protein-membrane interactions having potent and selective inhibition of a membrane-associated regulator of small GTPases. Molecules according to the invention designated as Bragsin, inhibit the activation of Arf GTPases. Such inhibition is performed for example by their guanine nucleotide exchange factor BRAG2 in vitro, and this effect is specific and manifests only in the presence of membranes. Advantageously, in cells, molecules according to the invention affect the trans-Golgi network, and this effect is rescued by ectopic expression of BRAG2 or constitutively active Arf and is phenocopied by BRAG2 gene silencing.

In one embodiment, said molecule is selected from the group consisting of:

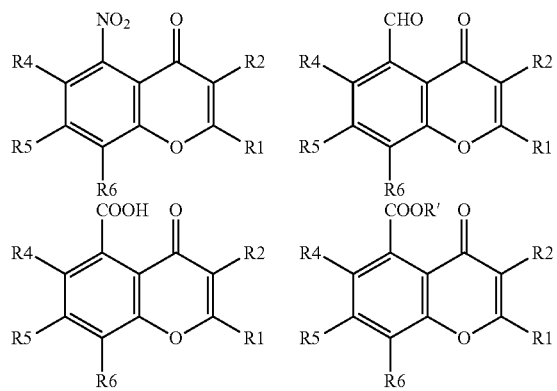

wherein R' is a chemical group of atoms, for example an alkyl optionally substituted or COOR' form an ester salt, for example a sodium ester.

In one embodiment, R4 is selected from the group consisting of an hydrogen, an hydroxy, an alkyl, preferably a methyl (Me) or ethyl (Et), an O-alkyl (or alkoxy), preferably OMe or OEt, an alkene, an O-alkylene, an alkyne, preferably —CCH, or an O-alkyne, preferably —OCH2-CCH.

In one embodiment, R6 is selected from the group consisting of an hydrogen, an hydroxy, an alkyl, preferably a methyl (Me) or ethyl (Et), an O-alkyl, preferably OMe or OEt, an alkene, an O-alkylene, an alkyne, preferably —CCH or an O-alkyne, preferably —OCH2-CCH.

In one embodiment, R5 is selected from the group consisting from the group consisting of an hydrogen, an hydroxy, an alkyl, preferably a methyl (Me) or ethyl (Et), an O-alkyl, preferably OMe or OEt, an alkene, an O-alkylene, an alkyne, preferably —CCH or an O-alkyne, preferably-OCH2-CCH.

In one embodiment, R2 is H.
In one embodiment, R4 is H.
In one embodiment, R5 is H.
In one embodiment, R6 is H.
In one embodiment, R6 is selected from the group consisting of an hydroxy, an alkyl, preferably a methyl (Me) or ethyl (Et), an O-alkyl (or alkoxy), preferably OMe or OEt, an alkene, an O-alkylene, an alkyne, preferably —CCH, or an O-alkyne, preferably —OCH2-CCH.
In one embodiment, R6 is OMe.
In one embodiment, R2, R5 and R6 are hydrogen atoms.
In one embodiment, said molecule is selected from the group consisting of:

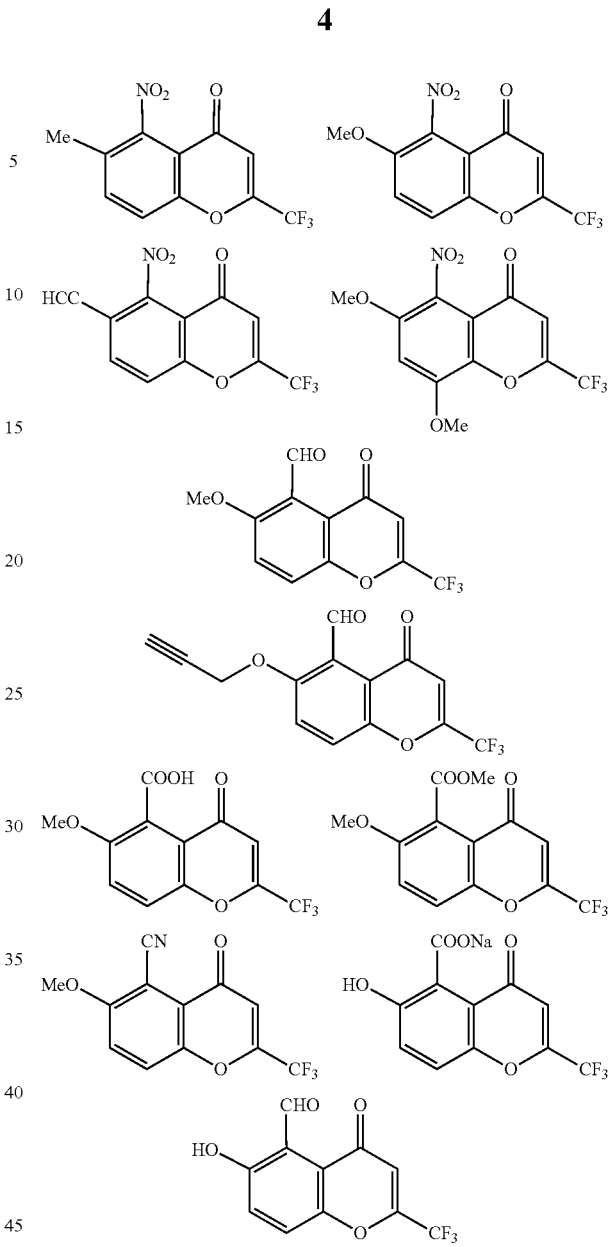

In one embodiment, said molecule is selected from the group consisting of:

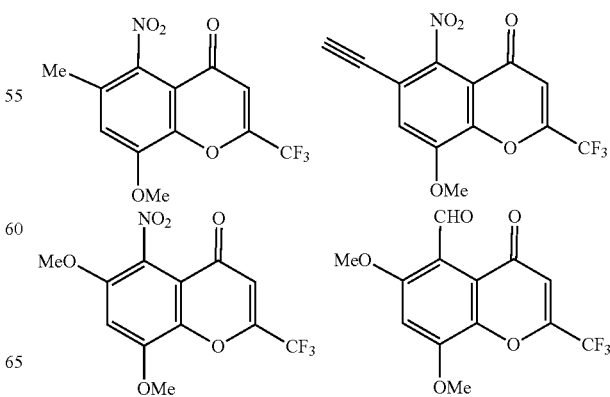

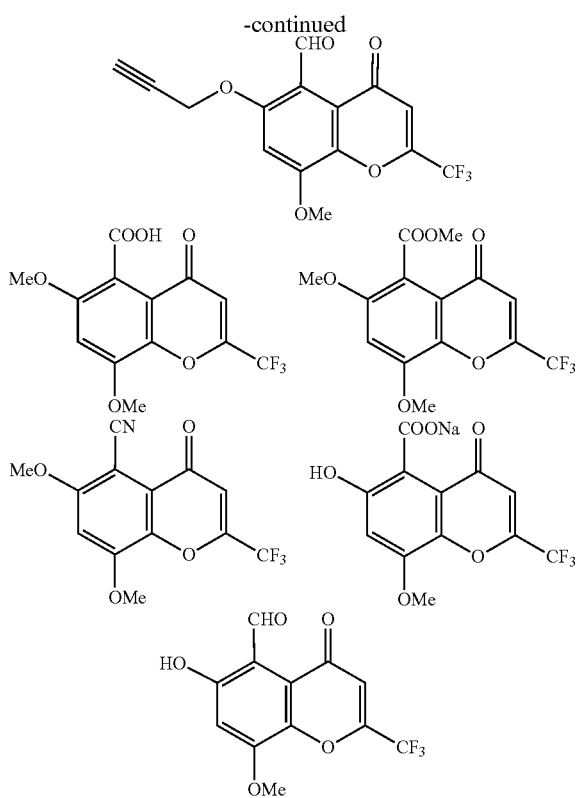

In one embodiment, wherein R1 is CF3.
In one embodiment, wherein R3 is NO$_2$.
In one embodiment, wherein R3 is NO$_2$ and R1 is CF$_3$.

As used herein, the term "alkyl group" means a saturated straight chain or branched non-cyclic hydrocarbon having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be optionally substituted with one or more substituents.

As used herein, the term "alkoxy" or "O-alkyl" refers to an alkyl group which is attached to another moiety by an oxygen atom. Examples of alkoxy groups include methoxy, isopropoxy, ethoxy, tert-butoxy, and the like. Alkoxy groups may be optionally substituted with one or more substituents.

As used herein, the term "heterocycloalkyl" means a monocyclic or polycyclic group having at least one heteroatom selected from O, N or S, and which has 2-11 carbon atoms, which may be saturated or unsaturated, but is not aromatic. Examples of heterocycloalkyl groups include (but are not limited to): piperidinyl, piperazinyl, 2-oxopiperazinyl, 2-oxopiperidinyl, 2-oxopyrrolidinyl, 4-piperidonyl, pyrrolidinyl, hydantoinyl, valerolactamyl, oxiranyl, oxetanyl, tetrahydropyranyl, tetrahydrothiopyranyl, tetrahydropyrindinyl, tetrahydropyrimidinyl, tetrahydrothiopyranyl sulfone, tetrahydrothiopyranyl sulfoxide, morpholinyl, thiomorpholinyl, thiomorpholinyl sulfoxide, thiomorpholinyl sulfone, 1,3-dioxolane, tetrahydrofuranyl, dihydrofuranyl-2-one, tetrahydrothienyl, and tetrahydro-1,1-dioxothienyl. Typically, monocyclic heterocycloalkyl groups have 3 to 7 members. Preferred 3 to 7 membered monocyclic heterocycloalkyl groups are those having 5 or 6 ring atoms. A heteroatom may be substituted with a protecting group known to those of ordinary skill in the art, for example, the hydrogen on a nitrogen may be substituted with a tert-butoxycarbonyl group. Furthermore, heterocycloalkyl groups may be optionally substituted with one or more substituents. In addition, the point of attachment of a heterocyclic ring to another group may be at either a carbon atom or a heteroatom of a heterocyclic ring. Only stable isomers of such substituted heterocyclic groups are contemplated in this definition.

As used herein the term "substituent" or "substituted" means that a hydrogen radical on a compound or group is replaced with any desired atom or group of atoms. Examples of substituents are those found in the exemplary compounds and embodiments disclosed herein when he molecule still present a BRAG2 inhibitor activity. Examples of substituents are haloge; alkyl; alkenyl; alkynyl; hydroxy; alkoxy; nitro; thiol; thioether; imine; cyano; amido; phosphonato; phosphine; carboxyl; thiocarbonyl; sulfonyl; sulfonamide; ketone; aldehyde; ester; oxygen (—O); haloalkyl (e.g., trifluoromethyl); cycloalkyl, which may be monocyclic or fused or non-fused polycyclic, or a heterocycloalkyl, which may be monocyclic or fused or non-fused polycyclic, monocyclic or fused or non-fused polycyclic aryl or heteroaryl; amino (primary, secondary, or tertiary); CO2CH3; CONH2; OCH2CONH2; NH2; SO2NH2; OCHF2; CF3; OCF3; and such moieties may also be optionally substituted by a fused-ring structure or bridge, for example —OCH2O—. These substituents may optionally be further substituted with a substituent selected from such groups. In one embodiment, the term "substituent" or the adjective "substituted" refers to a substituent selected from the group consisting of an alkyl, an alkenyl, an alkynyl, an cycloalkyl, an cycloalkenyl, a heterocycloalkyl, an aryl, a heteroaryl, an aralkyl, a heteraralkyl, a haloalkyl, —C(O)NR11R12, —NR13C(O)R14, a halo, —OR13, cyano, nitro, a haloalkoxy, —C(O)R13, —NR11R12, —SR13, —C(O)OR13, —OC(O)R13, —NR13C(O)NR11R12, —OC(O)NR11R12, —NR13C(O)OR14, —S(O)rR13, —NR13S(O)rR14, —OS(O)rR14, S(O)rNR11R12, —O, —S, and —N—R13, wherein r is 1 or 2; R11 and R12, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl; or R11 and R12 taken together with the nitrogen to which they are attached is optionally substituted heterocycloalkyl or optionally substituted heteroaryl; and R13 and R14 for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl.

The term "halogen" means —F, —Cl, —Br or —I. In one embodiment, Halogen is —Br. In one embodiment, Halogen is —Cl.

The crystal structure of the complex between BRAG2 and molecules according to the invention and structure-activity analysis using BRAG2 mutants and analogs of molecules according to the invention revealed that Preferably, a molecule according to the invention binds at the interface between the PH domain of BRAG2 and the lipid bilayer in a manner that renders BRAG2 unable to activate lipidated Arf.

Preferably, a molecule according to the invention depletes a cancer stem cell population in mammary tumor cell lines.

Preferably, a molecule according to the invention is for use in a treatment of a breast cancer, especially a breast cancer involving a BRAG2 overexpression.

A molecule according to the invention thus pioneers a novel class of cell-active inhibitors that impair protein-membrane interactions without disruption. The present invention is a new class of drugs targeting peripheral membrane proteins.

The invention also relates to an inhibitor having one or more protein-membrane interactions and inhibiting a mammal BRAG2, and preferably a human BRAG2, for use in a treatment of a cancer.

The invention also relates to an inhibitor of a mammal BRAG2, and preferably a human BRAG2, said inhibitor having a structure according to any one of claims 1 to 6.

The invention also relates to a method, notably in vitro or in cellulo, for inhibiting a mammal BRAG2, and preferably a human BRAG2, said method comprising putting BRAG2 in contact with a BRAG2 inhibitor as defined in the present invention.

The invention also relates to an inhibitor of a mammal BRAG2, and preferably a human BRAG2, said inhibitor having a structure as defined in the present invention.

The invention also relates to a method, notably in vitro or in cellulo, for inhibiting a mammal BRAG2, and preferably a human BRAG2, said method comprising putting BRAG2 in contact with a BRAG2 inhibitor as defined in the present invention.

The present invention focused notably on Arf GTPases, which orchestrate a variety of regulatory functions in lipid and membrane trafficking, and their GEF BRAG2. BRAG2 belongs to the BRAG family, whose members activate Arf GTPases to control signaling and/or endocytosis of integrins and other receptors and cell adhesion (D'Souza, R. S., & Casanova, J. E. (2016).—see below).

In one embodiment, molecules according to the present are inhibitors of Arf pathways.

In one embodiment, molecules according to the present invention are inhibitors of the activation of myristoylated Arf1 and myristoylated Arf6 by BRAG2.

In one embodiment, molecules according to the present invention do not inhibit the nucleotide exchange activity of BIG1, a Golgi ArfGEF, ARNO and EFA6a.

In one embodiment, molecules according to the present invention bind to PH domain of BRAG2.

In one embodiment, molecules according to the present invention are inhibitors of Sec7 domain of BRAG2.

Surprisingly, in one preferred embodiment, molecules according to the present invention are specific to BRAG2 over BIG1, a Golgi ArfGEF, and of ARNO, EFA6a.

Surprisingly, in one preferred embodiment, molecules according to the present invention are BRAG2 inhibitors in the presence of an artificial membrane, and even more surprisingly of a membrane containing $PIP_2$. In one embodiment, molecules according to the present invention bind at the interface between the PH domain and the membrane.

In one embodiment, molecules according to the present invention disperse TGN46 immuno-staining in cells.

The present invention also relates to a complex of BRAG2, especially human BRAG2, and more particularly $BRAG2^{Sec7-PH}$, with a molecule according to the present invention.

BRAG2 is implicated in severe pathologies, including breast cancer (Morishige, M. et al. (2008)), uveal melanoma (Yoo, J. H. et al. (2016)), diabetic retinopathy Zhu, W. et al. (2017)) and mental retardation Shoubridge, C. et al. (2010)). BRAG family members contain a Sec7 domain, which is responsible for stimulating GDP/GTP exchange, followed by a pleckstrin homology (PH) domain, which binds $PIP_2$-containing membranes with high affinity. Previous work has shown that $PIP_2$-containing membranes potentiate the GEF activity of BRAG2 by more than three orders of magnitude (Aizel, K. et al. Integrated conformational and lipid-sensing regulation of endosomal ArfGEF BRAG2. *PLOS Biol* 11, e1001652 (2013) and Jian, X., Gruschus, J. M., Sztul, E. & Randazzo, P. A. The pleckstrin homology (PH) domain of the Arf exchange factor Brag2 is an allosteric binding site. *J Biol Chem* 287, 24273-83 (2012). This large increase in activity is determined by the interaction of BRAG2 with multiple lipids, resulting in its precisely oriented apposition to the membrane (Karandur, D., Nawrotek, A., Kuriyan, J. & Cherfils, J. Multiple interactions between an Arf/GEF complex and charged lipids determine activation kinetics on the membrane. *Proc Natl Acad Sci USA* 114, 11416-11421 (2017).

The present invention also relates to a pharmaceutical composition comprising at least one molecule as defined in the present invention, said composition comprising one or more excipients and optionally one other pharmaceutically active ingredient.

As is known to the person skilled in the art, various forms of excipients can be used adapted to the mode of administration and some of them can promote the effectiveness of the active molecule, e.g. by promoting a release profile rendering this active molecule overall more effective for the treatment desired.

The pharmaceutical compositions of the invention are thus able to be administered in various forms, more specially for example in an injectable, pulverizable or ingestible form, for example via the intramuscular, intravenous, subcutaneous, intradermal, oral, topical, rectal, vaginal, ophthalmic, nasal, transdermal or parenteral route. A preferred route is oral administration. The present invention notably covers the use of a compound according to the present invention for the manufacture of pharmaceutical composition.

Such medicament can take the form of a pharmaceutical composition adapted for oral administration, which can be formulated using pharmaceutically acceptable carriers well known in the art in suitable dosages. Such carriers enable the pharmaceutical compositions to be formulated as tablets, pills, dragees, capsules, liquids, gels, syrups, slurries, suspensions, and the like, for ingestion by the patient. In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

The present invention also relates to a molecule or a pharmaceutical composition as defined in the present invention for use in a method of a therapeutic treatment of disease presenting a deregulated expression of BRAG2, preferably an overexpression of BRAG2.

The present invention also relates to a molecule or a pharmaceutical composition as defined in the present invention as a drug having a protein-membrane interaction for use in a method of a therapeutic treatment of disease in need of a protein-membrane interaction.

In one embodiment, said disease is selected from the group consisting of a cancer, in particular an invasive cancer, a cancer with metastasis, a cancer resistant to an EGFR and/or ErbB2 modulator, angiogenesis, diabetic retinopathy, nonsyndromic intellectual disability, etc.

The present invention also relates to a molecule or a pharmaceutical composition as defined in the present invention for use in a method of a therapeutic treatment of a disease is selected from the group consisting of a cancer, in particular an invasive cancer, a cancer with metastasis, a cancer resistant to an EGFR and/or ErbB2 modulator, angiogenesis, diabetic retinopathy, non-syndromic intellectual disability, etc.

The present invention also relates to a method of therapeutic treatment, said method comprising administering to a mammal in need thereof an effective amount of at least one molecule as defined in the present invention.

Preferably, said mammal is a human patient.

In one embodiment, said method of treatment is for treating breast cancer, and in particular breast cancer in need of targeting bCSC population.

A method of treatment of a cancer or angiogenesis according to the invention is for example supported by:

Brag2 and Cancers

D'Souza, R. S., & Casanova, J. E. (2016). The BRAG/IQSec family of Arf GEFs. *Small GTPases*, 7(4), 257-264. http://doi.org/10.1080/21541248.2016.1219442

Matsumoto, Y., Sakurai, H., Kogashiwa, Y., Kimura, T., Matsumoto, Y., Shionome, T., et al. (2017). Inhibition of epithelial-mesenchymal transition by cetuximab via the EGFR-GEP100-Arf6-AMAP1 pathway in head and neck cancer. *Head & Neck*, 39(3), 476-485. http://doi.org/10.1002/hed.24626

Xie, C.-G., Wei, S.-M., Chen, J.-M., Xu, X.-F., Cai, J.-T., Chen, Q.-Y., & Jia, L.-T. (2012). Down-Regulation of GEP100 Causes Increase in E-Cadherin Levels and Inhibits Pancreatic Cancer Cell Invasion. *PLOS ONE*, 7(5), e37854. http://doi.org/10.1371/journal.pone.0037854

Hu, Z., Du, J., Yang, L., Zhu, Y., Yang, Y., Zheng, D., et al. (2012). GEP100/Arf6 is required for epidermal growth factor-induced ERK/Rac1 signaling and cell migration in human hepatoma HepG2 cells. *PLOS ONE*, 7(6), e38777. http://doi.org/10.1371/journal.pone.0038777

Menju, T., Hashimoto, S., Hashimoto, A., Otsuka, Y., Handa, H., Ogawa, E., et al. (2011). Engagement of overexpressed Her2 with GEP100 induces autonomous invasive activities and provides a biomarker for metastases of lung adenocarcinoma. *PLOS ONE*, 6(9), e25301. http://doi.org/10.1371/journal.pone.0025301

Yoo, J. H. et al. ARF6 Is an Actionable Node that Orchestrates Oncogenic GNAQ Signaling in Uveal Melanoma. *Cancer Cell* 29, 889-904 (2016).

Breast Cancer

Hu, Z., Xu, R., Liu, J., Zhang, Y., Du, J., Li, W., et al. (2013). GEP100 regulates epidermal growth factor-induced MDA-MB-231 breast cancer cell invasion through the activation of Arf6/ERK/uPAR signaling pathway. *Experimental Cell Research*, 319(13), 1932-1941. http://doi.org/10.1016/j.yexcr.2013.05.028

Sabe, H., Hashimoto, S., Morishige, M., Ogawa, E., Hashimoto, A., Nam, J.-M., et al. (2009). The EGFR-GEP100-Arf6-AMAP1 signaling pathway specific to breast cancer invasion and metastasis. *Traffic (Copenhagen, Denmark)*, 10(8), 982-993. http://doi.org/10.1111/j.1600-0854.2009.00917.x Sabe, H., Hashimoto, S., Morishige, M., Ogawa, E., Hashimoto, A., Nam, J.-M., et al. (2009). The EGFR-GEP100-Arf6-AMAP1 signaling pathway specific to breast cancer invasion and metastasis. *Traffic (Copenhagen, Denmark)*, 10(8), 982-993. http://doi.org/10.1111/j.1600-0854.2009.00917.x Morishige, M. et al. GEP100 links epidermal growth factor receptor signalling to Arf6 activation to induce breast cancer invasion. *Nat Cell Biol* 10, 85-92 (2008).

Angiogenesis

Manavski, Y., Carmona, G., Bennewitz, K., Tang, Z., Zhang, F., Sakurai, A., et al. (2014). Brag2 differentially regulates β1- and β3-integrin-dependent adhesion in endothelial cells and is involved in developmental and pathological angiogenesis. *Basic Research in Cardiology*, 109(2), 404. http://doi.org/10.1007/s00395-014-0404-2

Hashimoto, A., Hashimoto, S., Ando, R., Noda, K., Ogawa, E., Kotani, H., et al. (2011). GEP100-Arf6-AMAP1-cortactin pathway frequently used in cancer invasion is activated by VEGFR2 to promote angiogenesis. *PLOS ONE*, 6(8), e23359. http://doi.org/10.1371/journal.pone.0023359

Zhu, W., Shi, D. S., Winter, J. M., Rich, B. E., Tong, Z., Sorensen, L. K., et al. (2017). Small GTPase ARF6 controls VEGFR2 trafficking and signaling in diabetic retinopathy. *The Journal of Clinical Investigation*, 127 (12). http://doi.org/10.1172/JCI91770

Sakurai, A., Jian, X., Lee, C. J., Manavski, Y., Chavakis, E., Donaldson, J., et al. (2011). Phosphatidylinositol-4-phosphate 5-kinase and GEP100/Brag2 protein mediate anti-angiogenic signaling by semaphorin 3E-plexin-D1 through Arf6 protein. *Journal of Biological Chemistry*, 286(39), 34335-34345. http://doi.org/10.1074/jbc.M111.259499

And also:

Zhu, W. et al. Small GTPase ARF6 controls VEGFR2 trafficking and signaling in diabetic retinopathy. *J Clin Invest* (2017).

Shoubridge, C. et al. Mutations in the guanine nucleotide exchange factor gene IQSEC2 cause nonsyndromic intellectual disability. *Nat Genet* 42, 486-8 (2010).

Figure 11:
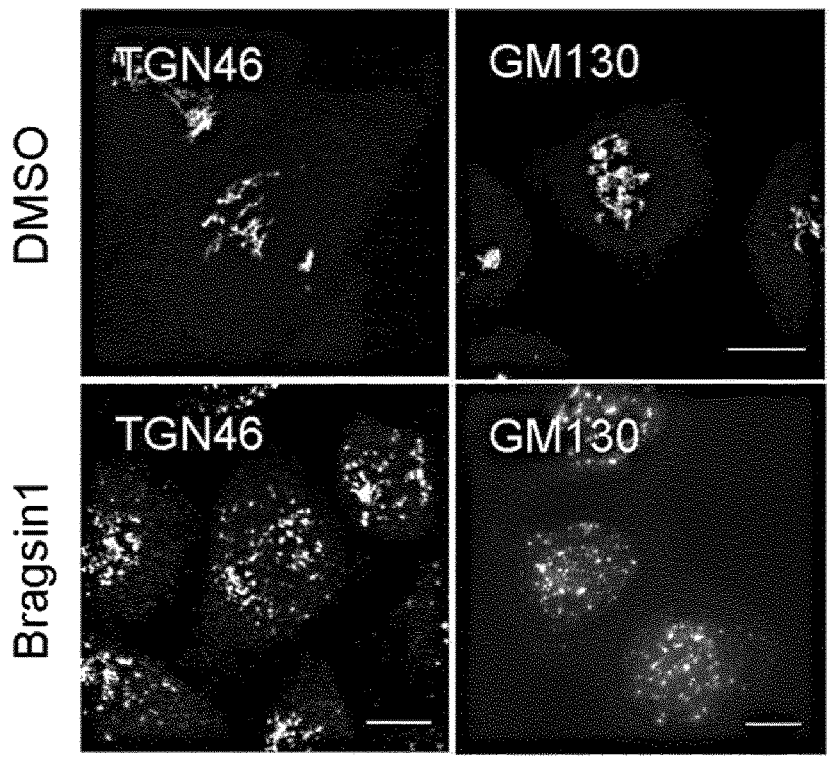
Figure 12:
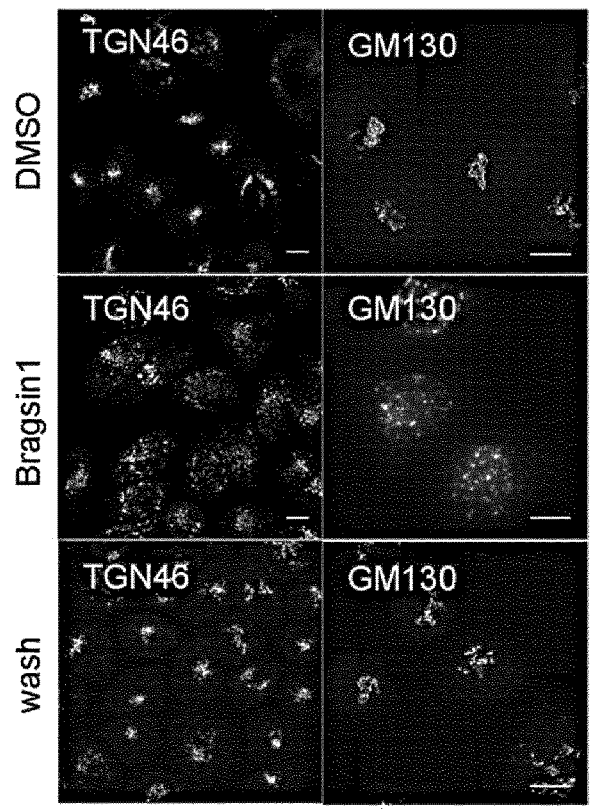
Figure 13:
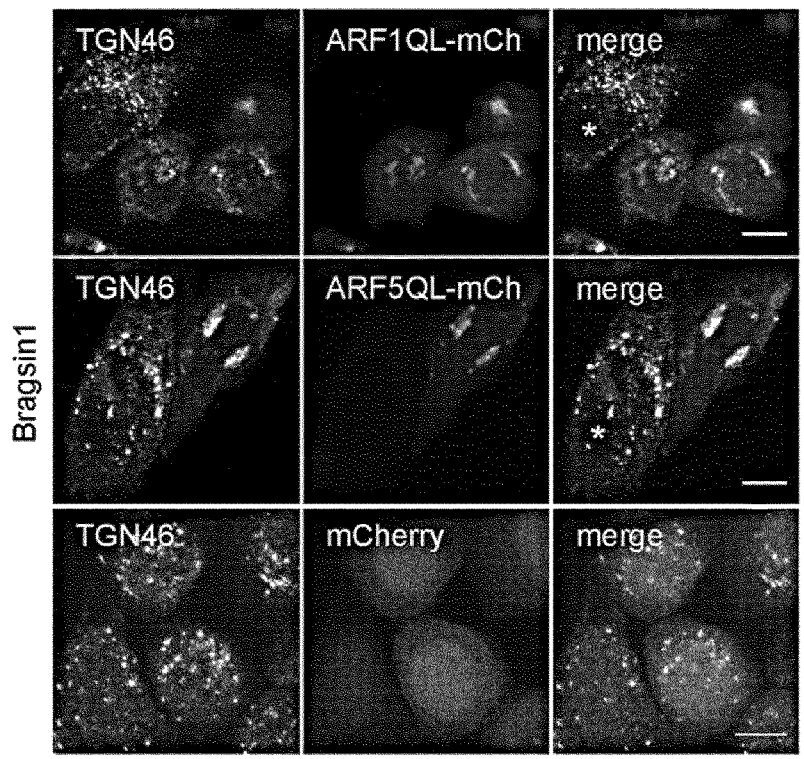

In the figures:

FIG. 1. Bragsin2 affects Arf pathways in cells
  a. Chemical structures of Bragsin1 and Bragsin2 and derivatives used in this study. Chemical synthesis and structural characterization of the compounds are described in example 6.
  b. Bragsin2 disperses the TGN46 and GM130 markers. HeLa cells were treated with either DMSO (0.25%) or Bragsin2 (50 μM) for 30 min, immunostained for TGN46, GM130 or EEA1 (green channel) and analysed by confocal microscopy. The effect of Bragsin1 treatments are shown in FIG. 11.
  c. Dispersion of GM130 and TGN46 by Bragsin2 is reversible. Hela cells were treated as in FIG. 1a and were incubated for an additional 30 min in fresh medium (wash panel) prior to immunostaining and confocal microscopy analysis. Reversibility of the effect of Bragsin1 is shown in FIG. 12.

d. Expression of Arf-mCherry constructs carrying an activating mutation rescues the effect of Bragsin2. Hela cells were transfected with constitutively active Q/L mutants of Arf-mCherry. Note the difference between non-transfected cells (white asterisk) and transfected cells. Rescue of Bragsin1 phenotype by constitutively active Arf mutants is shown in FIG. 13. Scale bars, 10 µm.

Figure 2:
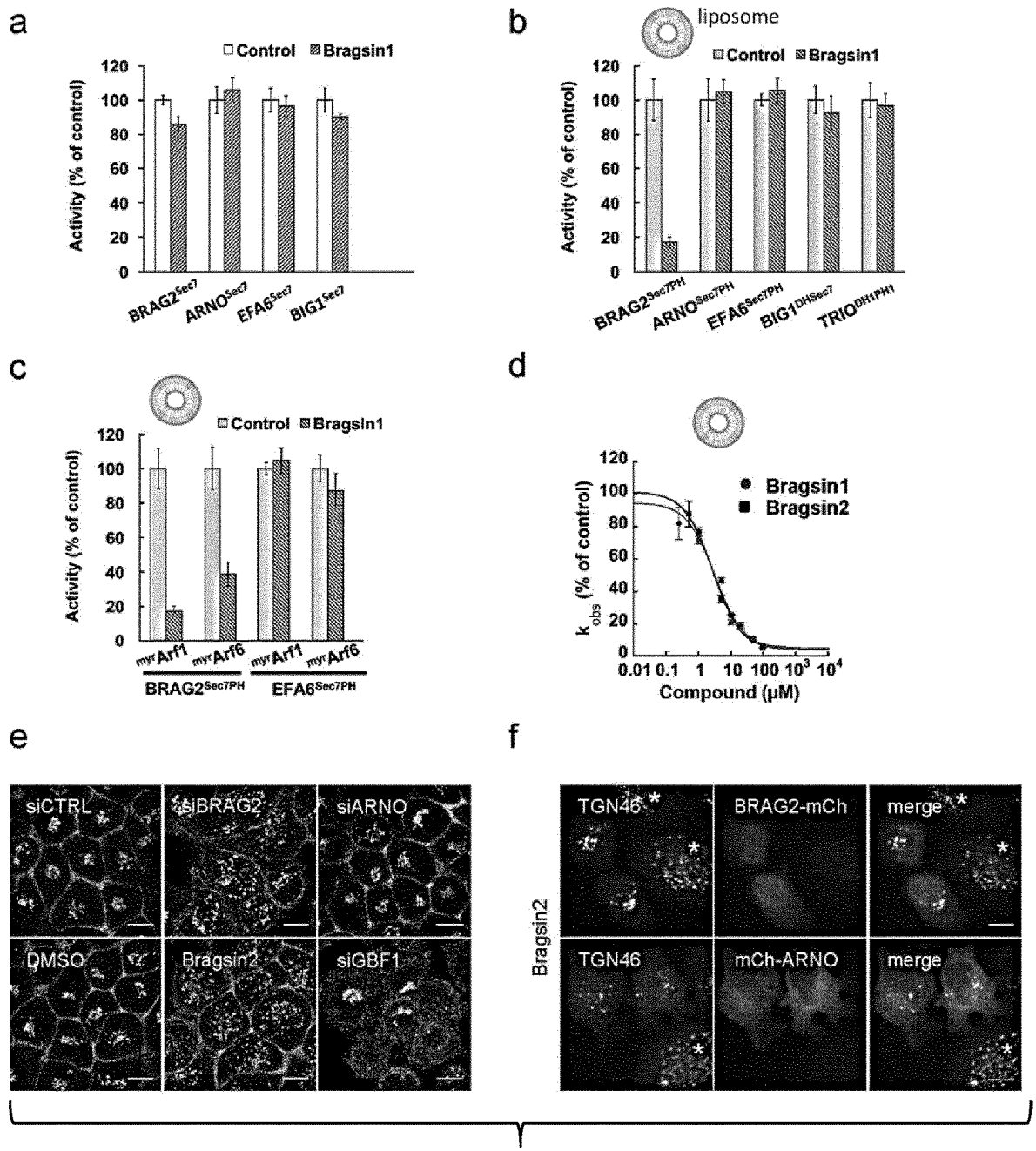
Figure 17:
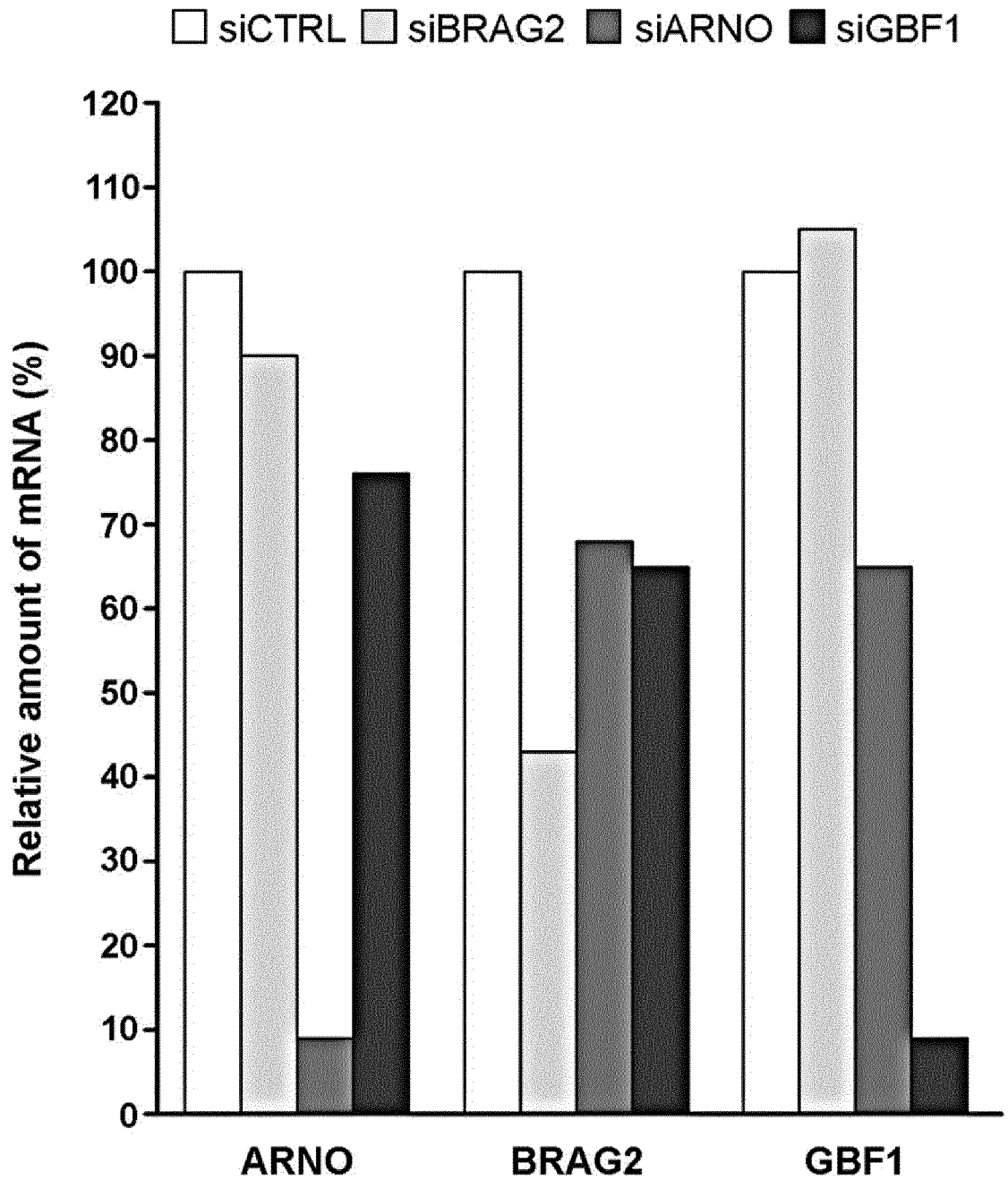
Figure 19:
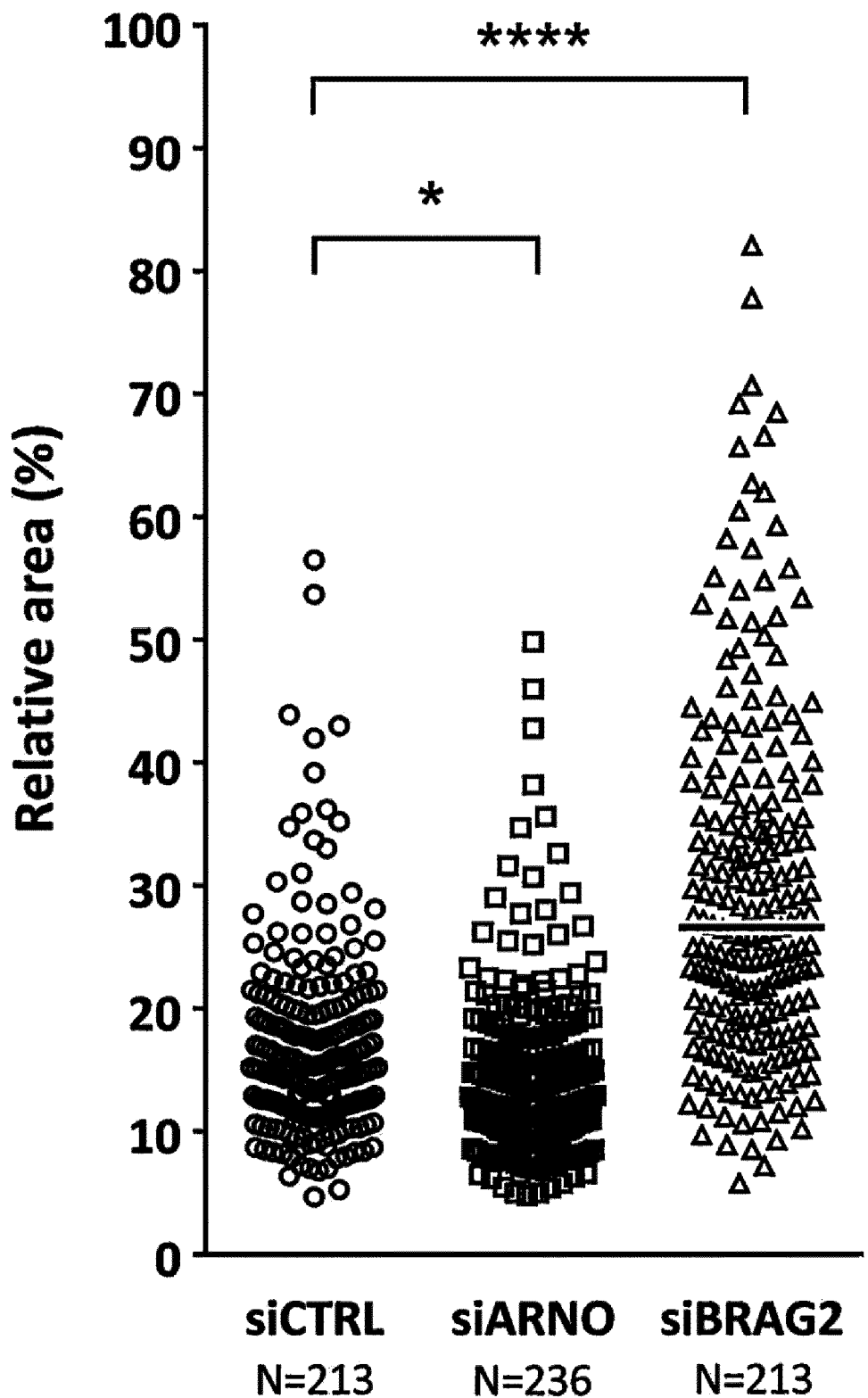
Figure 20:
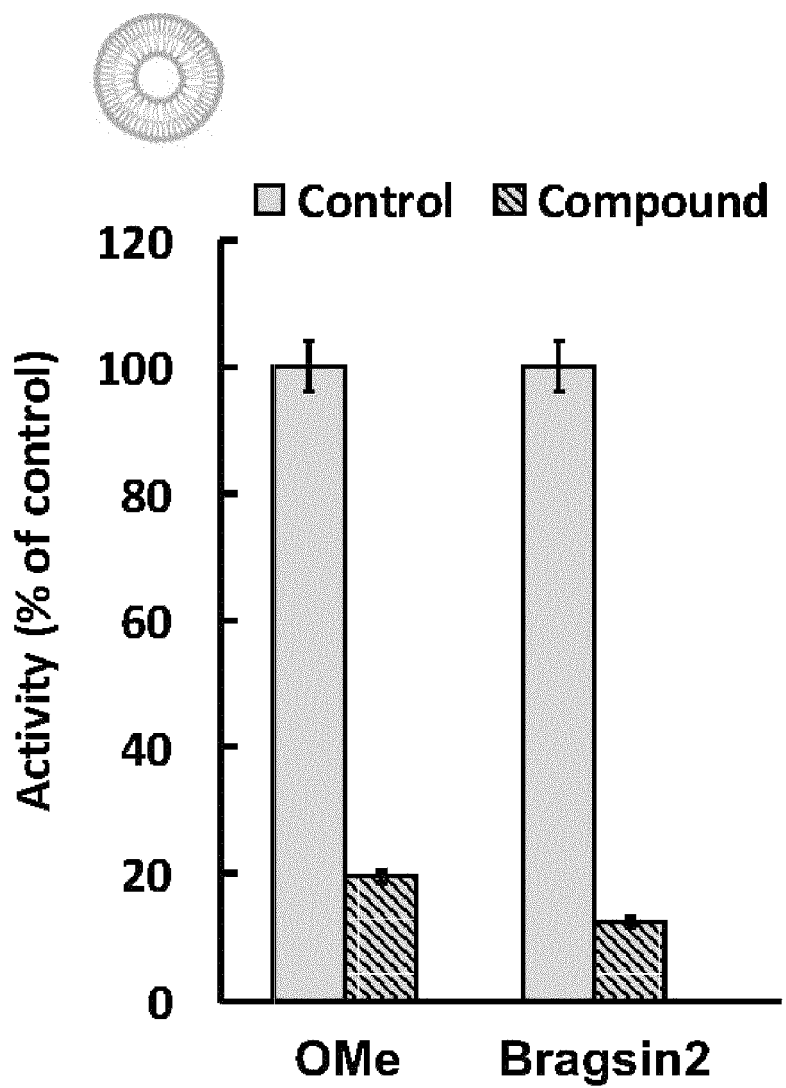
Figure 21:
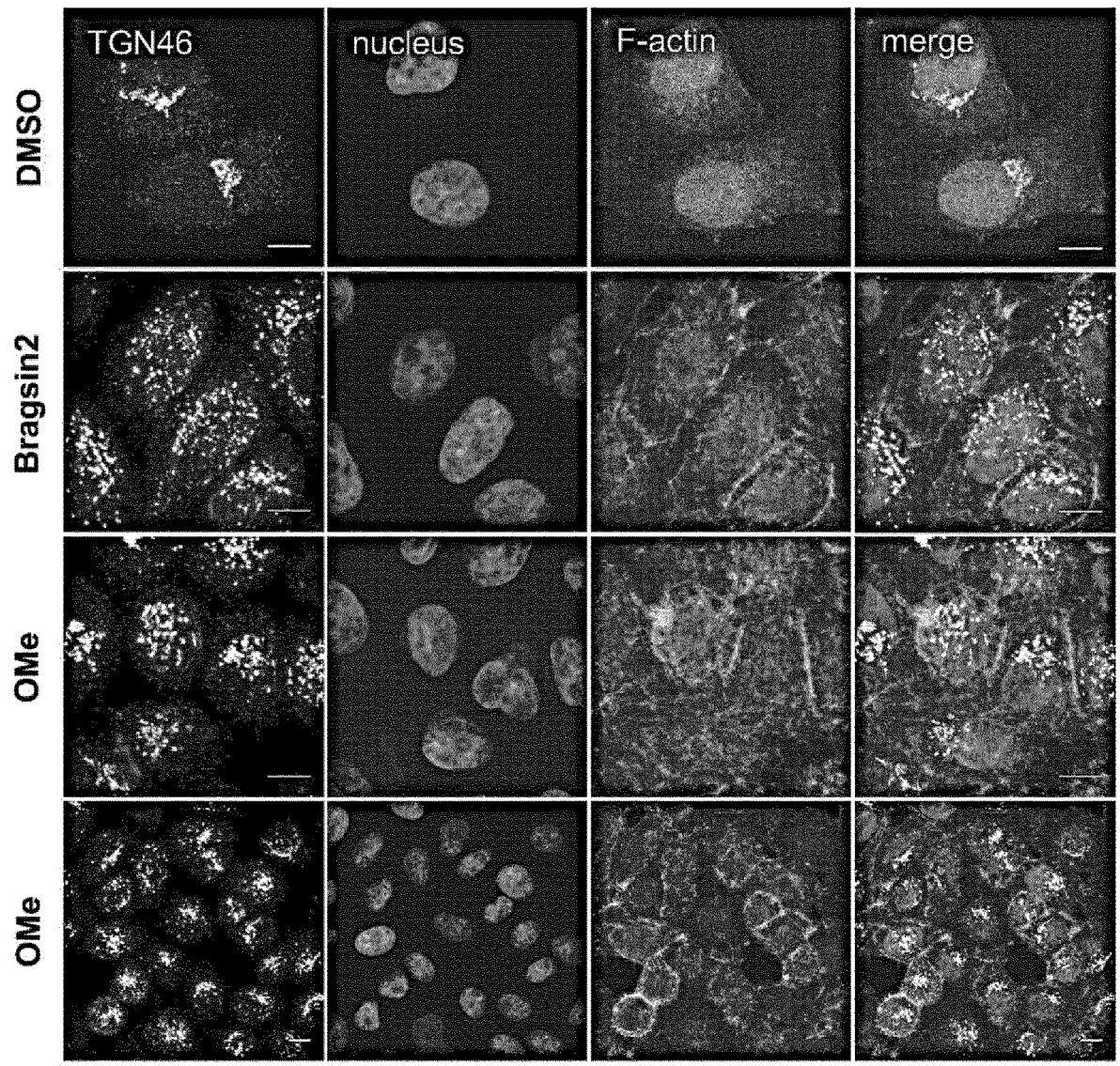
Figure 22:
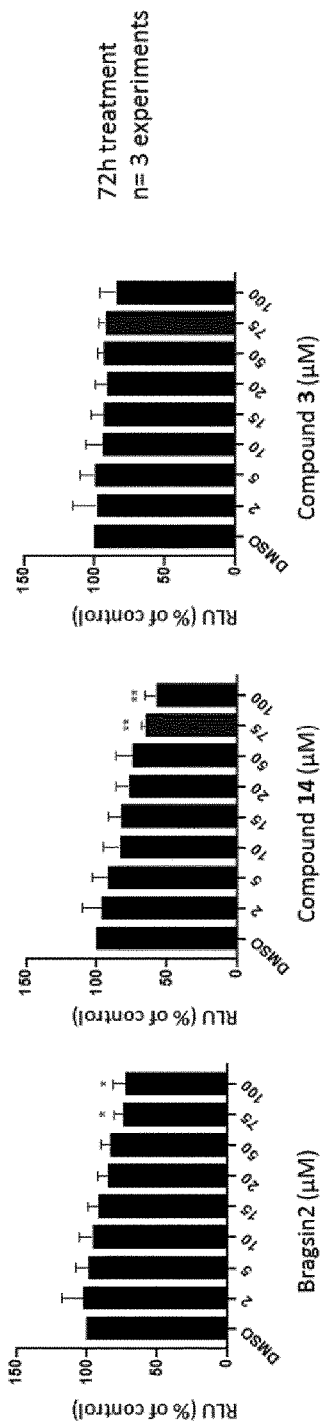
Figure 22:
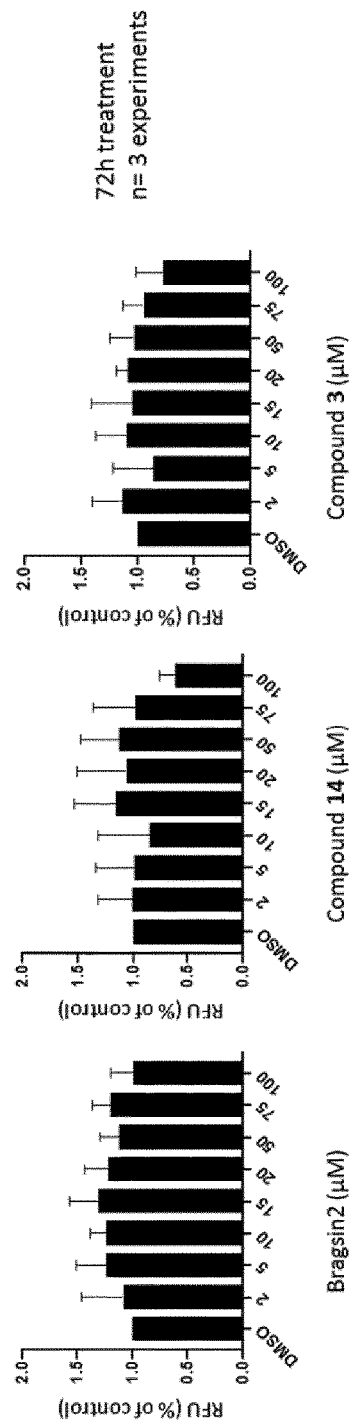
Figure 23:
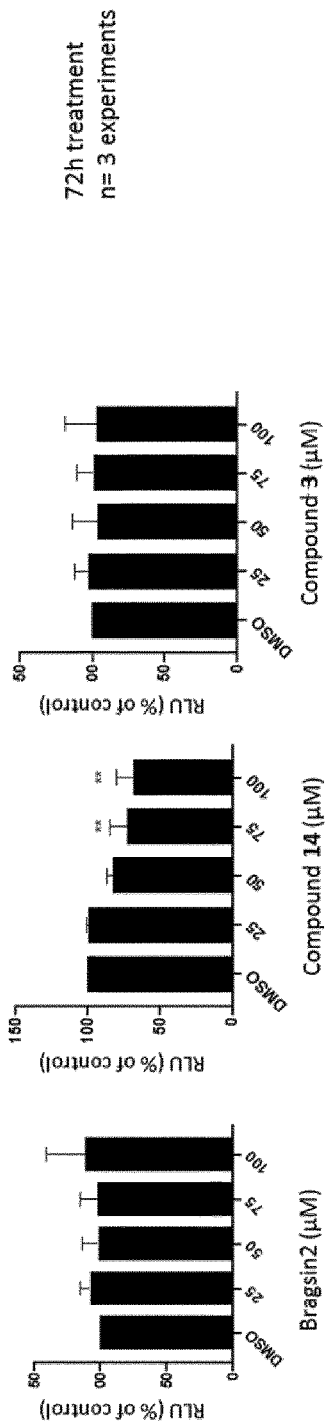
Figure 23:
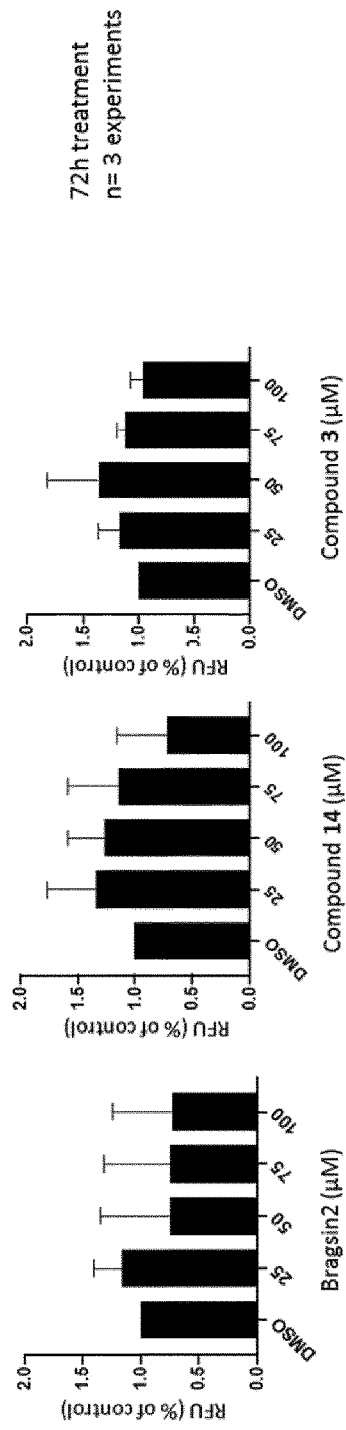
Figure 24:
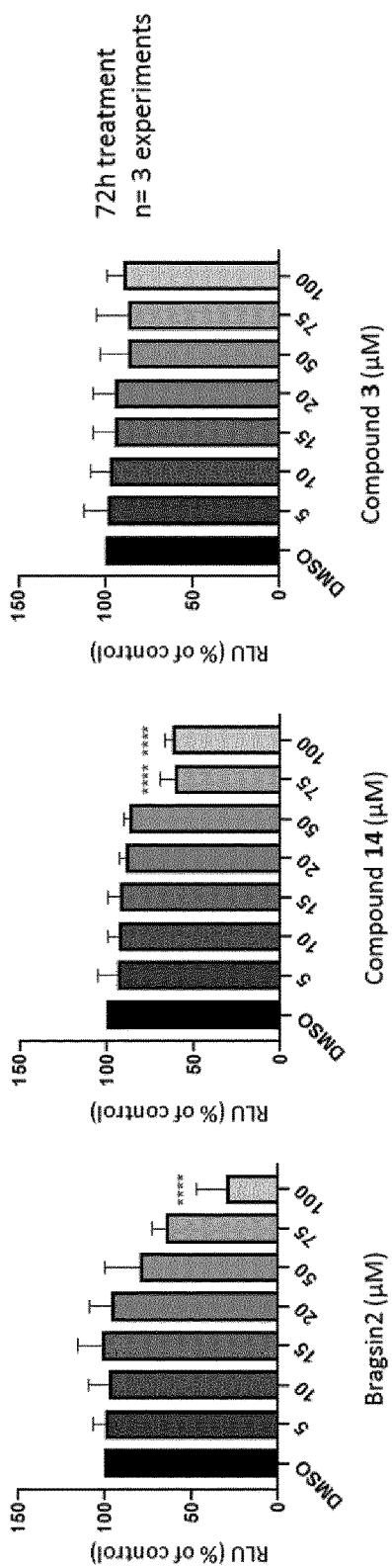
Figure 25:
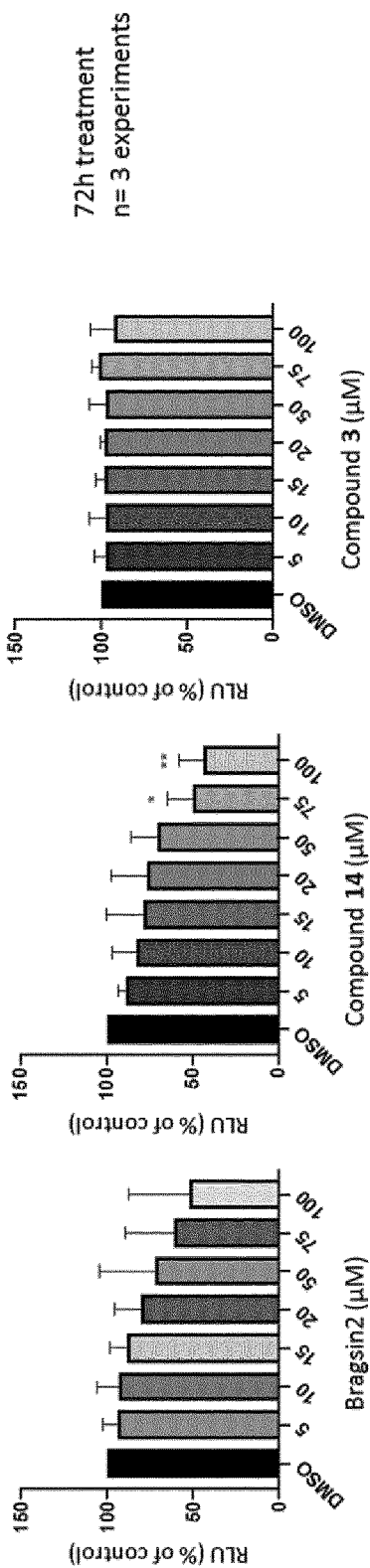
Figure 26:
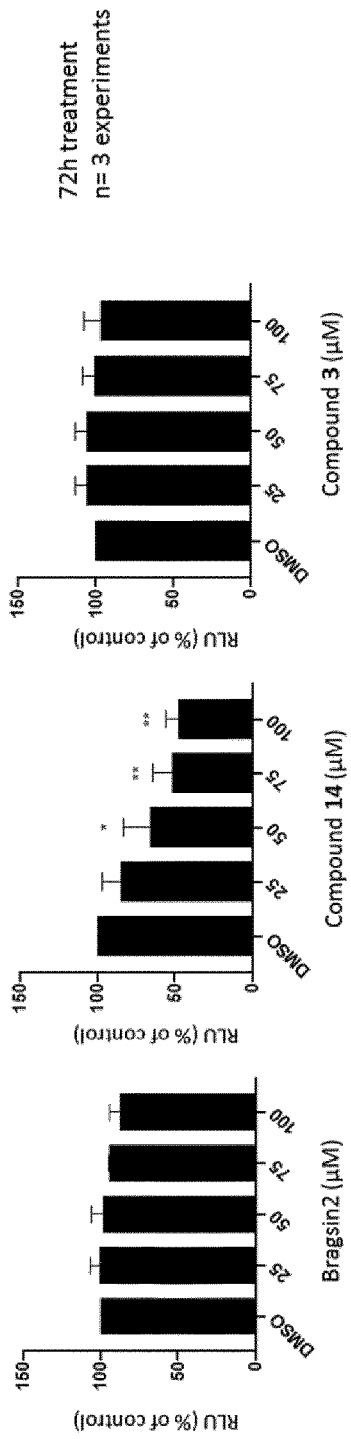
Figure 26:
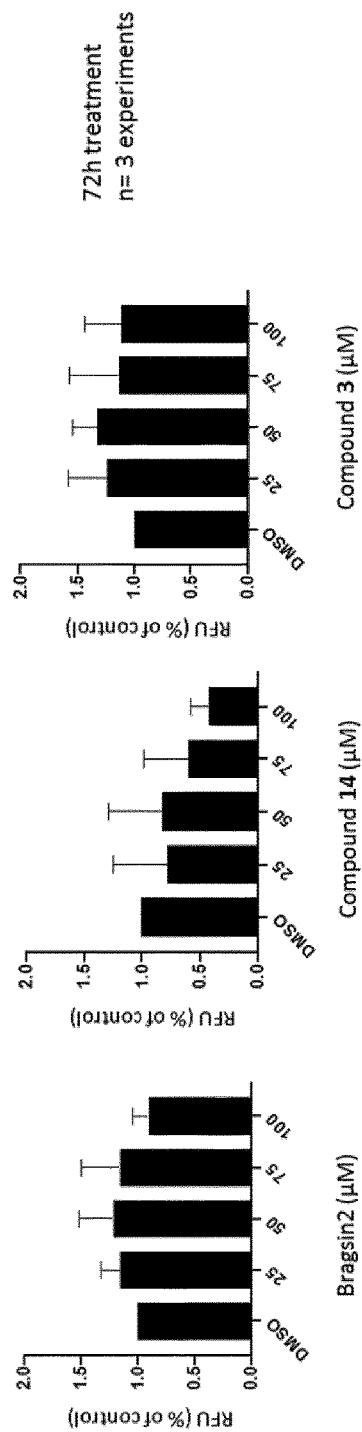
Figure 27:
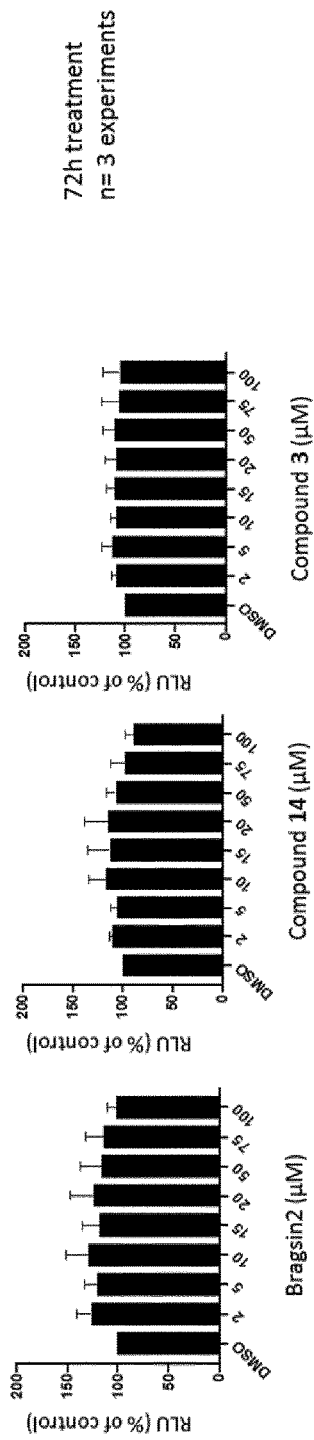
Figure 27:
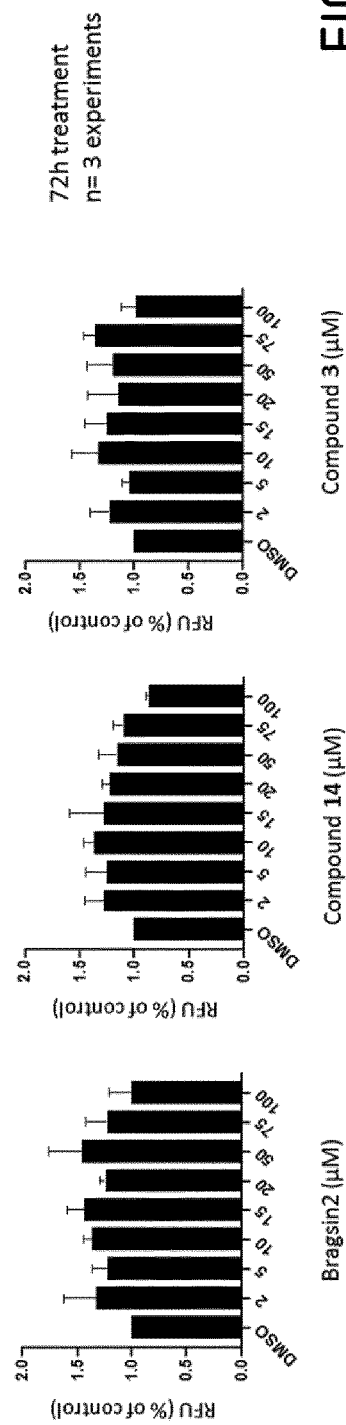
Figure 28:
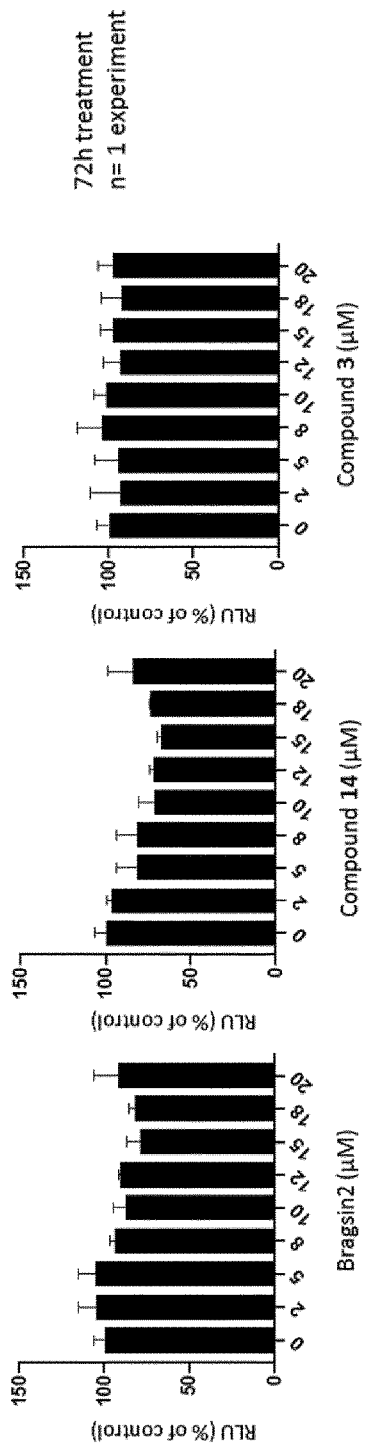
Figure 28:
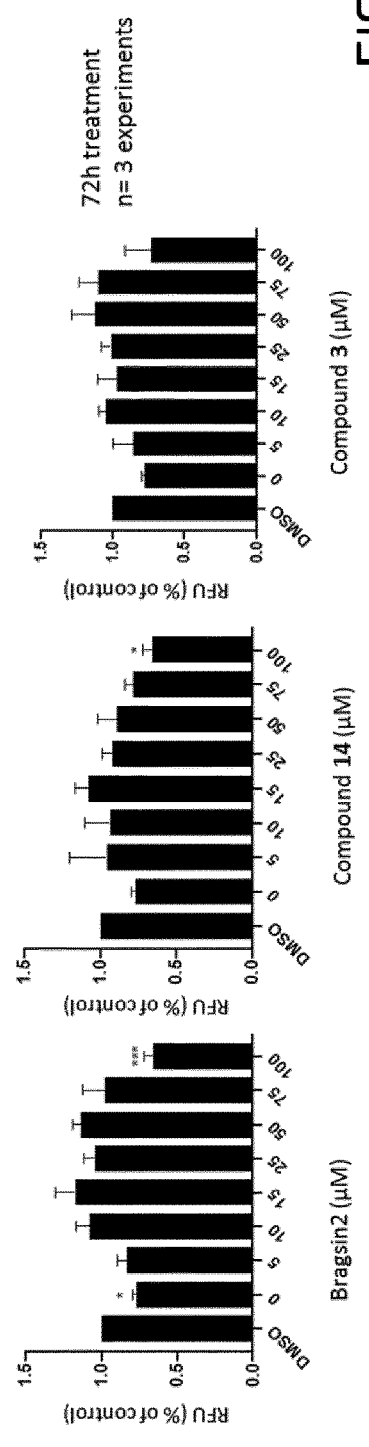
Figure 29:
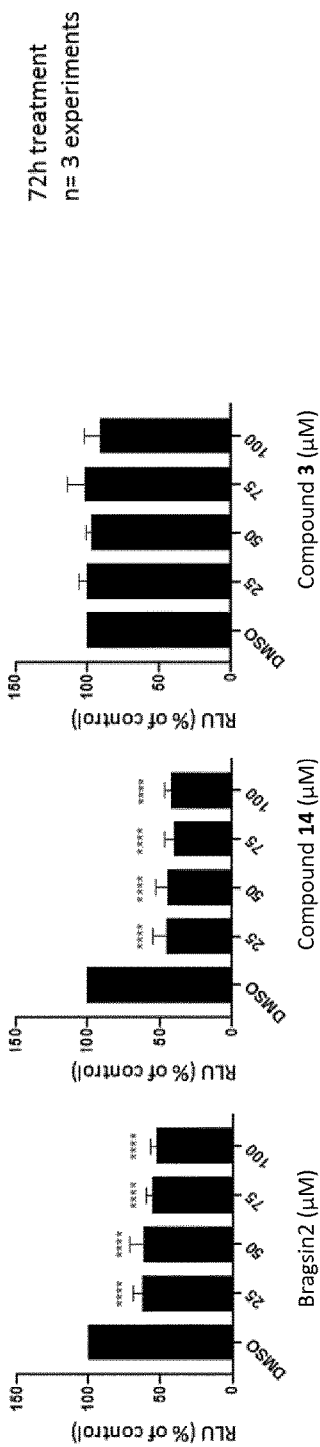
Figure 29:
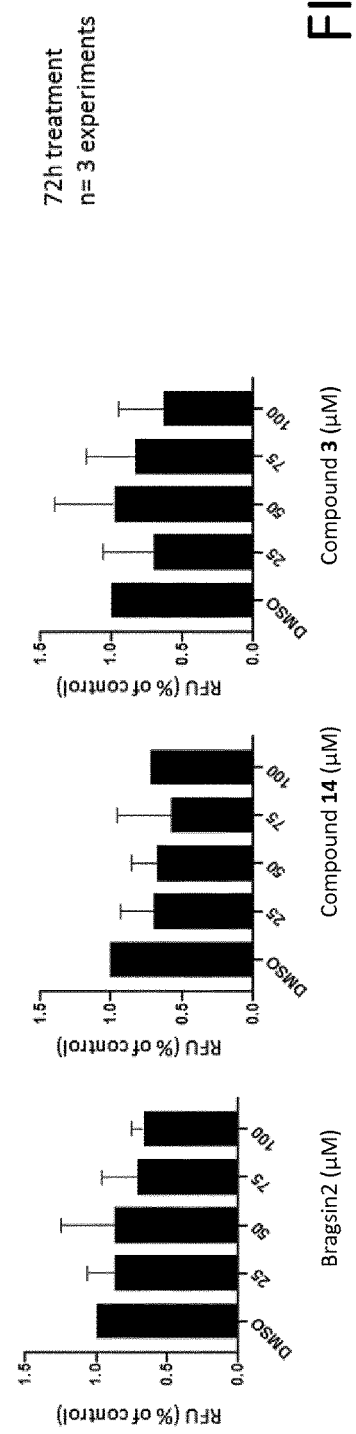

FIG. 2. Bragsin is a specific inhibitor of the ArfGEF BRAG2 a. Bragsin1 has no effect on the Sec7 domain of human ArfGEFs in solution. Nucleotide exchange kinetics were measured by fluorescence kinetics in the presence of Bragsin1 (50 µM) or DMSO using purified Sec7 domains and a truncated version of Arf1 (D17Arf1), which can be activated in solution. Representative kinetic profiles are given in FIG. 14.

b. Bragsin1 specifically inhibits BRAG2 in the presence of liposomes. Nucleotide exchange kinetics were determined in the presence of Bragsin1 (50 µM) or DMSO with ArfGEF constructs carrying membrane-binding domains and myristoylated Arf1. Rac1 was artificially tethered to liposomes by a C-terminal hexahistidine tag as described in (Peurois, F. et al. *Biochem J* 474, 1259-1272 (2017). Representative kinetic profiles are given in FIG. 15.

c. Bragsin1 inhibits the activation of myristoylated Arf6 by BRAG2 on liposomes. Experiments were carried out as in FIG. 2*b*. Representative kinetic profiles are given in FIG. 16.

d. Dose-response of Bragsin1 and Bragsin2 towards myristoylated Arf1 and BRAG2 on liposomes. Experiments were carried out as in FIG. 2*b*.

e. Silencing of BRAG2 phenocopies the effect of Bragsin2 on the TGN46 compartment. Hela cells were treated with DMSO or Bragsin2 (50 µM) or transfected with siRNAs targeting BRAG2, ARNO or GBF1 or with a control siRNA (siCTRL). Immunofluorescence staining of TGN46 is in green (white-grey on the black-white figures). Cell boundaries were highlighted by actin staining (magenta (grey on the black-white figures). SiRNA silencing efficiencies are shown in FIG. 17. Scale bars, 10 µm. Statistical analysis of the dispersal of TGN46 staining is shown in FIG. 19.

f. Overexpression of BRAG2 rescues the dispersion of the TGN46 compartment induced by Bragsin. Hela cells were transfected with BRAG2-mCherry (magenta channel) and treated with Bragsin2 (50 µM). Immunofluorescence staining of TGN46 is in green (white-grey on the black-white figures).

Figure 3:
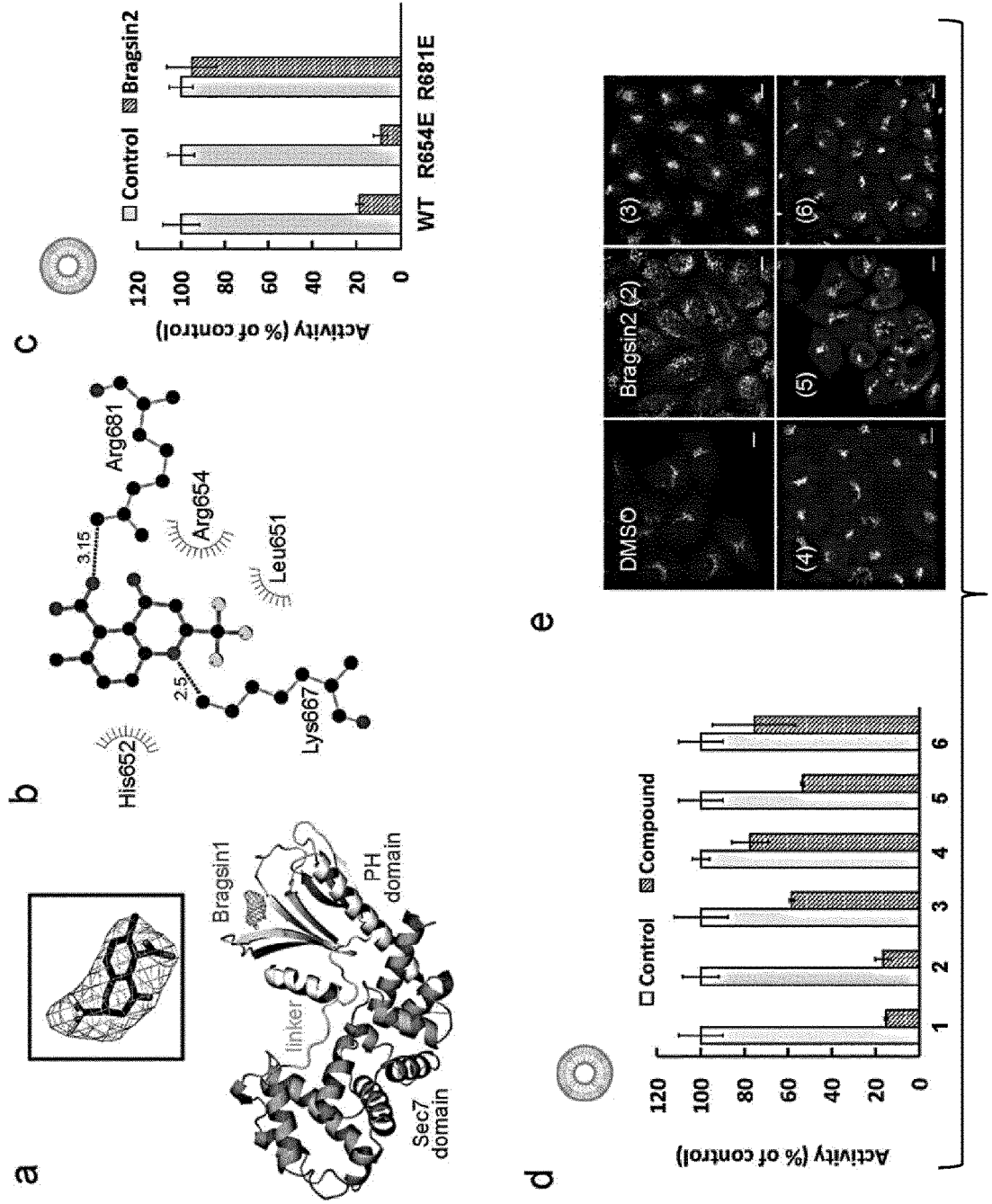

FIG. 3. Bragsin binds to the PH domain of BRAG2 a. Crystallographic structure of Bragsin1 bound to the PH domain of BRAG2. The inset shows an electron density omit map of the inhibitor. The Sec7 domain is in pink, the linker in yellow, the PH domain in blue.

b. Interactions of Bragsin1 with residues of the PH domain. Hydrogen bonds are shown in dotted lines.

c. Analysis of the inhibition of BRAG2 mutants by Bragsin2. GEF efficiencies were measured by fluorescence kinetics using myristoylated Arf1 as in FIG. 2*b*.

d. Structure-activity relationship analysis of Bragsin analogs. All compounds were used at 20 mM. GEF activities were measured by fluorescence kinetics using myristoylated Arf1 as in FIG. 2*b*.

e. Effect of Bragsin analogs on the TGN46 compartment. Hela cells treated with the compounds (50 mM) were immunostained and analysed by confocal microscopy as in FIG. 1*b*.

Figure 4:
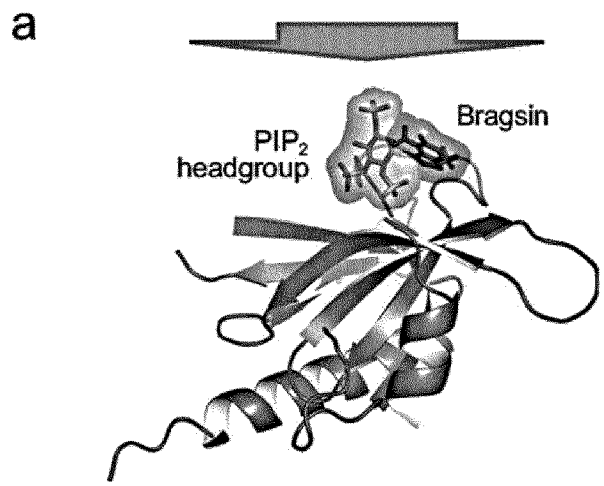
Figure 4:
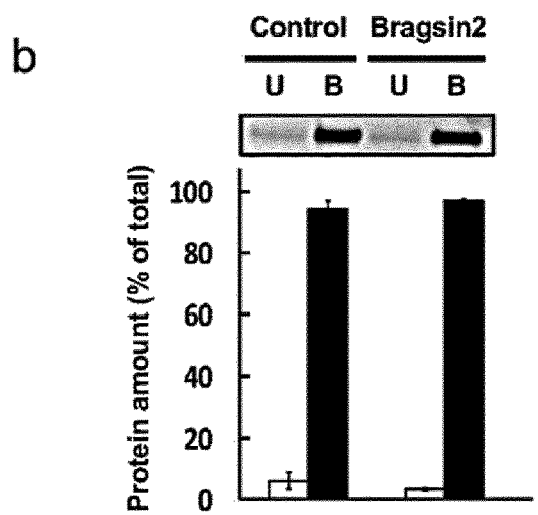
Figure 4:
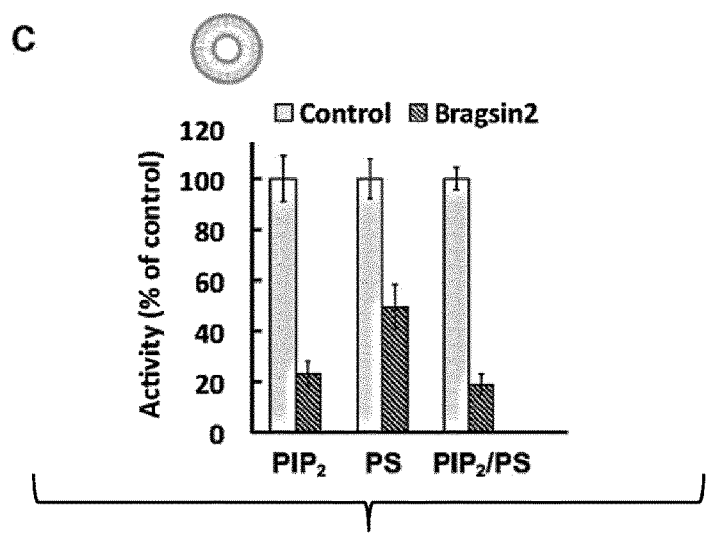

FIG. 4. Bragsin is a non-competitive inhibitor of protein-membrane interactions a. Bragsin1 (in violet) overlaps with the canonical phosphoinositide-binding site of the PH domain of BRAG2. IP3 (in red) is from the GRP1-IP3 complex (DiNitto, J. P. et al. Structural basis and mechanism of autoregulation in 3-phosphoinositide-dependent Grp1 family Arf GTPase exchange factors. *Mol Cell* 28, 569-83 (2007)). The position of the membrane is indicated by an arrow.

b. Bragsin2 does not impair binding of BRAG2 to liposomes. Binding was measured by liposome flotation. U: bottom fraction, containing unbound proteins; B: top fraction, containing liposome-bound proteins. Proteins are revealed by Instant Blue staining after SDS-PAGE. Quantification is shown below.

c. Inhibition of BRAG2 by Bragsin2 is stronger in the presence of liposomes that contain $PIP_2$ lipids. Kinetics were measured as in FIG. 2*b*.

Figure 5:
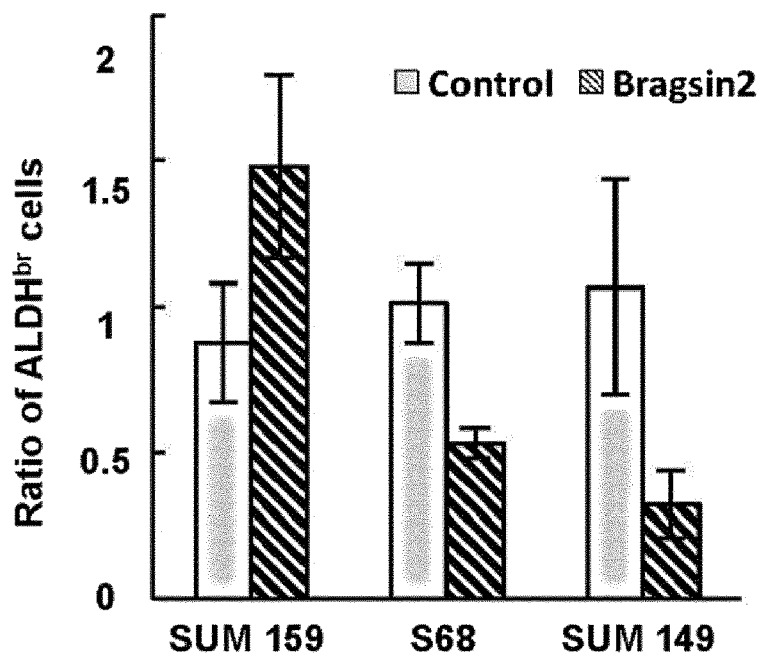
Figure 5:
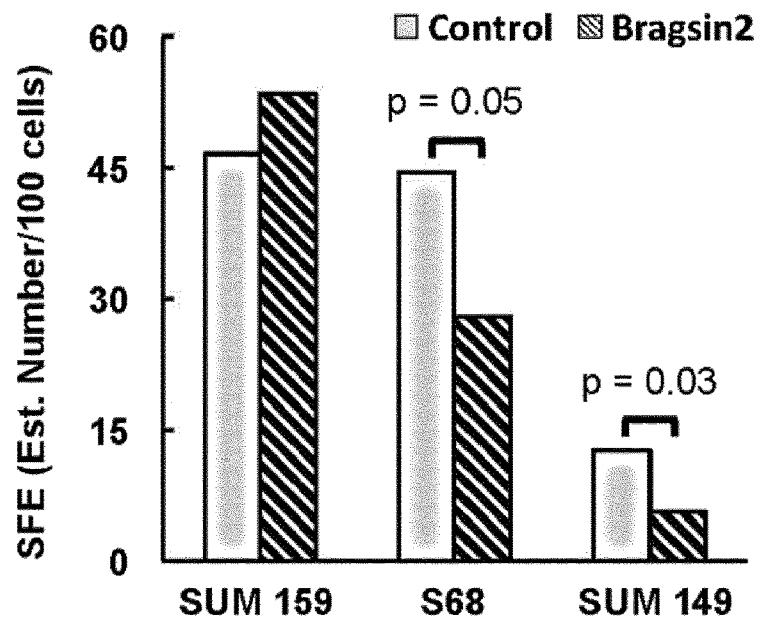

FIG. 5. Bragsin affects breast cancer stem cells a. Evolution of the proportion of $ALDH^{br}$ cells after treatment with Bragsin2 using the Aldefluor assay. Results are expressed as mean±SD.

b. Tumorsphere-forming efficiency (SFE) was calculated using an extreme limiting dilution analysis (ELDA) algorithm. Results are expressed as the estimated number of tumorspheres obtained for 100 cells plated.

Figure 6:
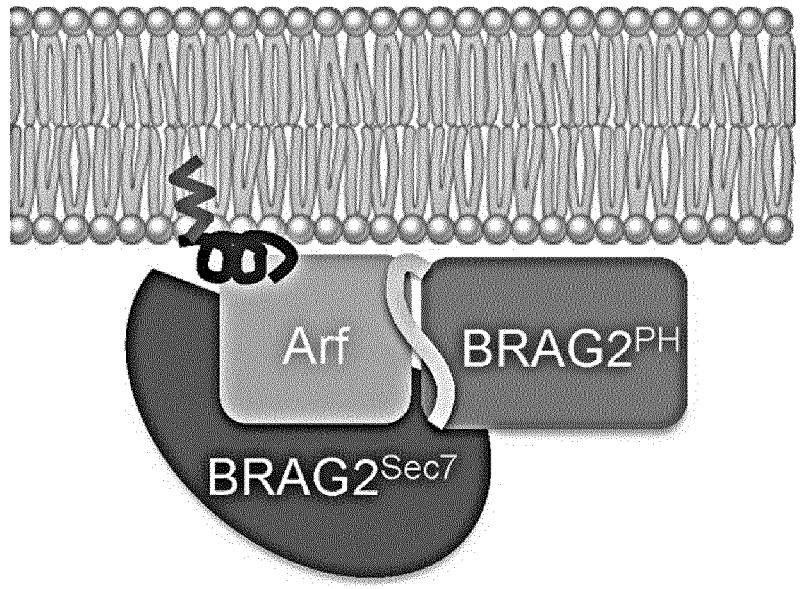
Figure 6:
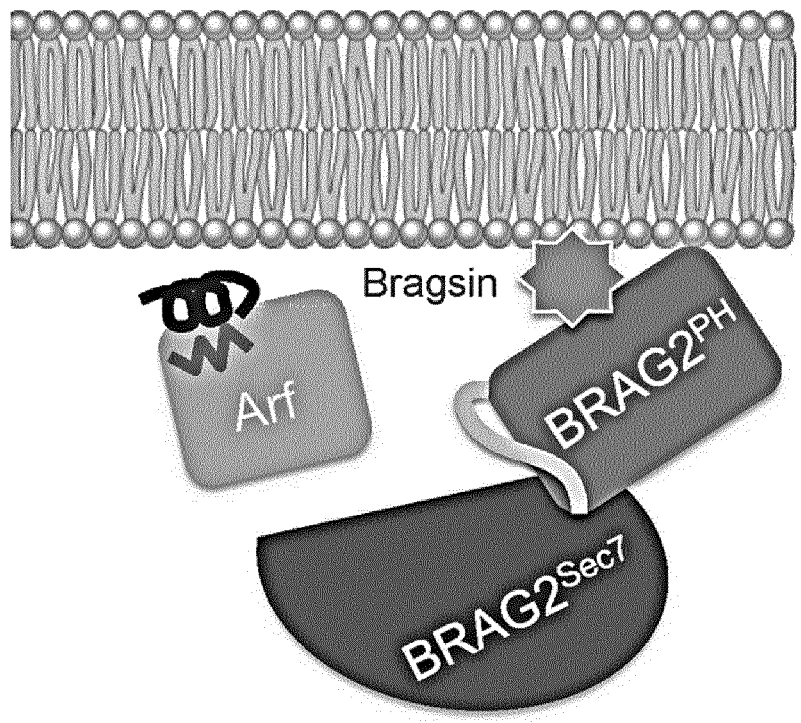

FIG. 6. A model for protein-membrane interfacial inhibition by Bragsin

Figure 7:
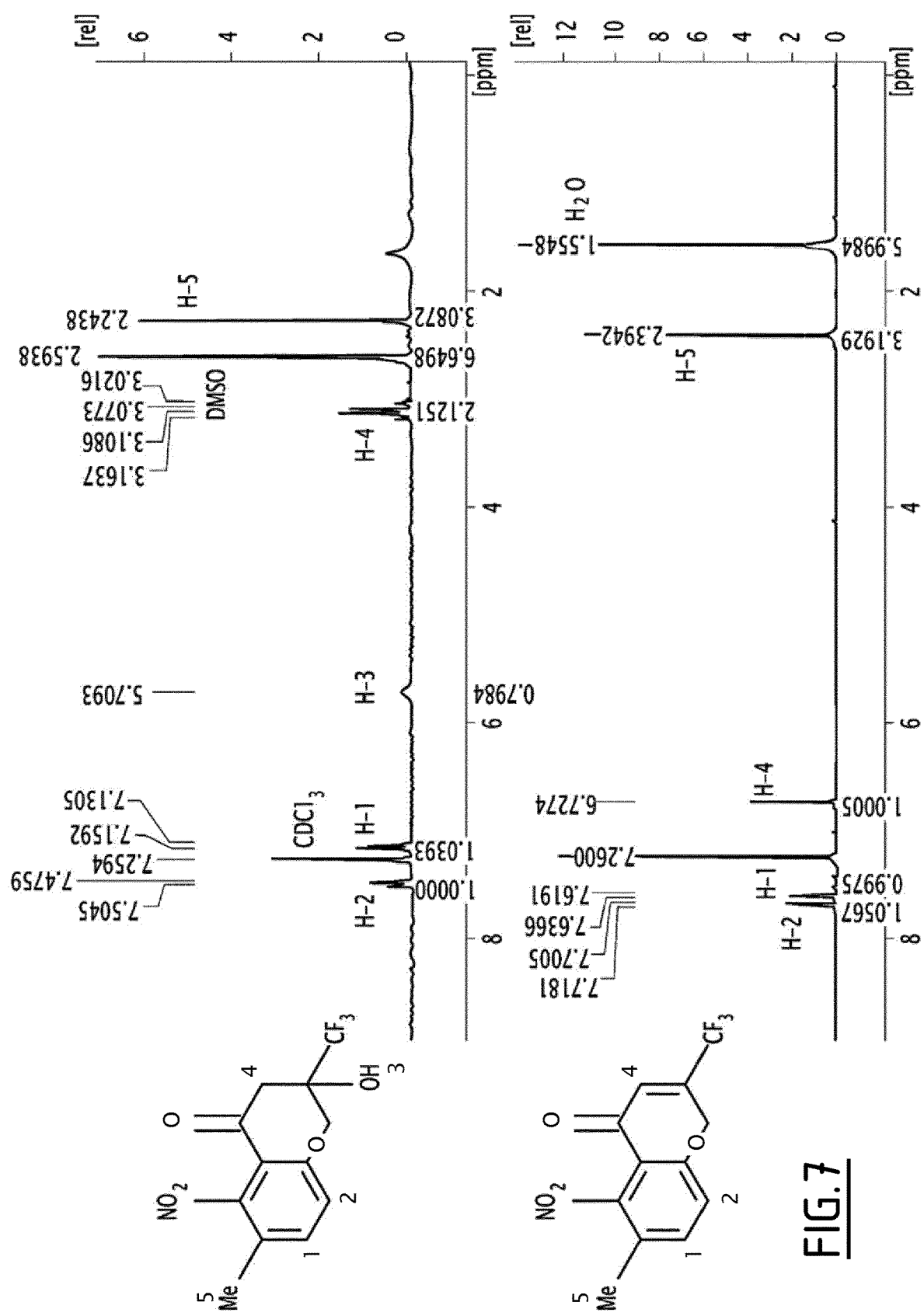
Figure 8:
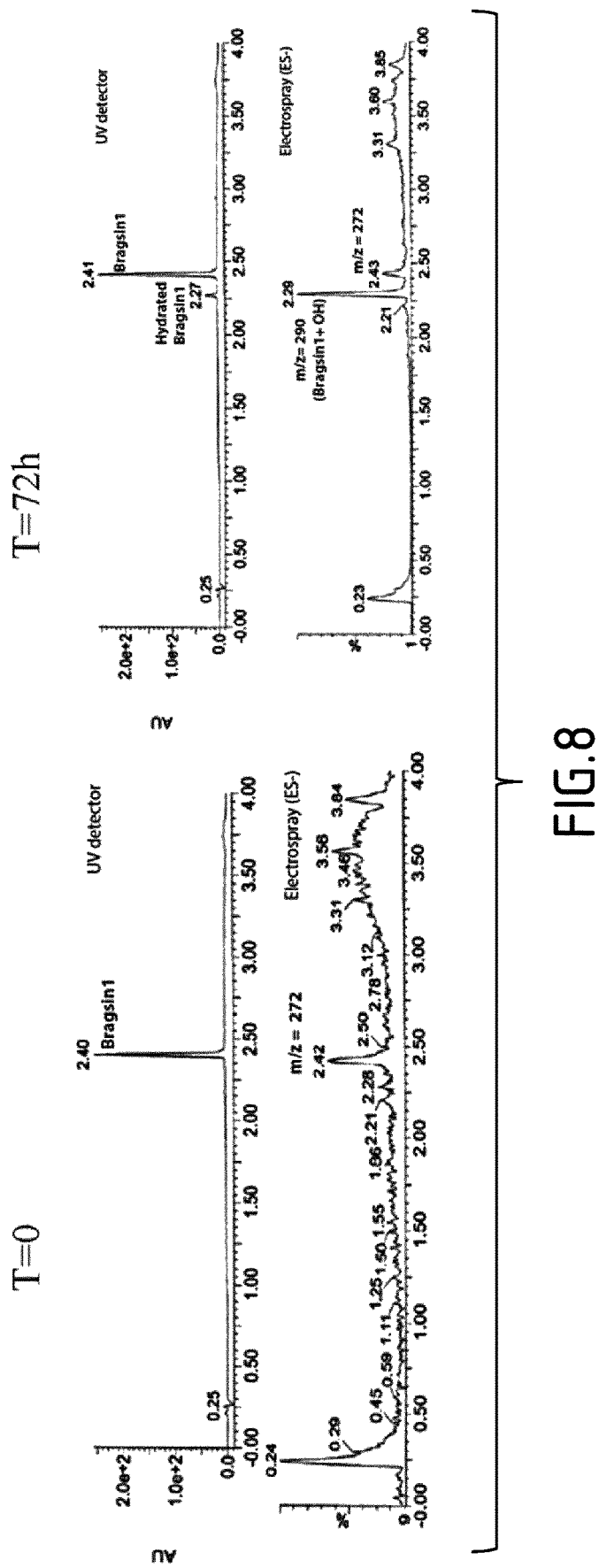
Figure 9:
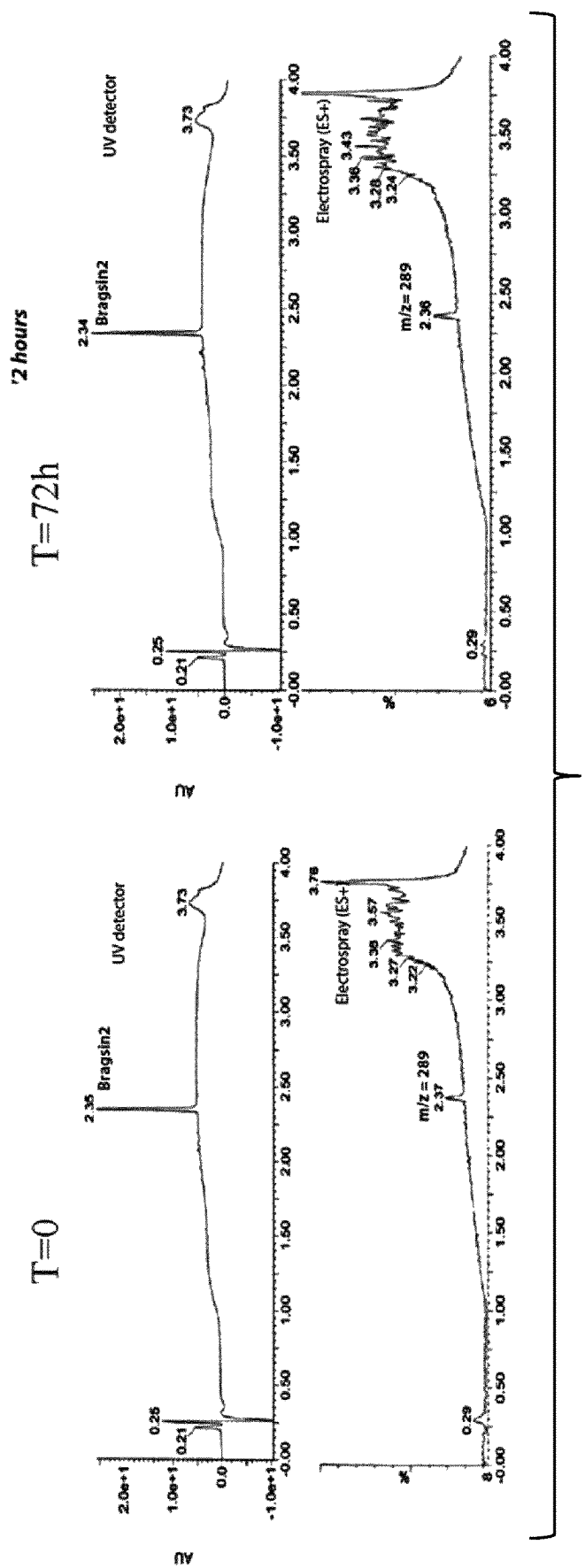

FIGS. 7-9. Analysis of the stability of Bragsin1 and Bragsin2

FIG. 7. Bragsin1 that has been kept in a stock solution in DMSO for several months lost activity towards BRAG2 (not shown). $^1$H-NMR analysis shows that it completely decomposed to hydrated compound (13)

FIG. 8-9. Mass spectroscopy analysis shows Bragsin1 is less stable than Bragsin2. Bragsin1 and Bragsin2 were dissolved in PBS. Bragsin1 slowly decomposed to hydrolyzed compound within 72 hours (FIG. 8) while Bragsin2 remained stable (Fig. c).

FIGS. 10-13: Bragsin1 has the same cellular effects as Bragsin2

Figure 10:
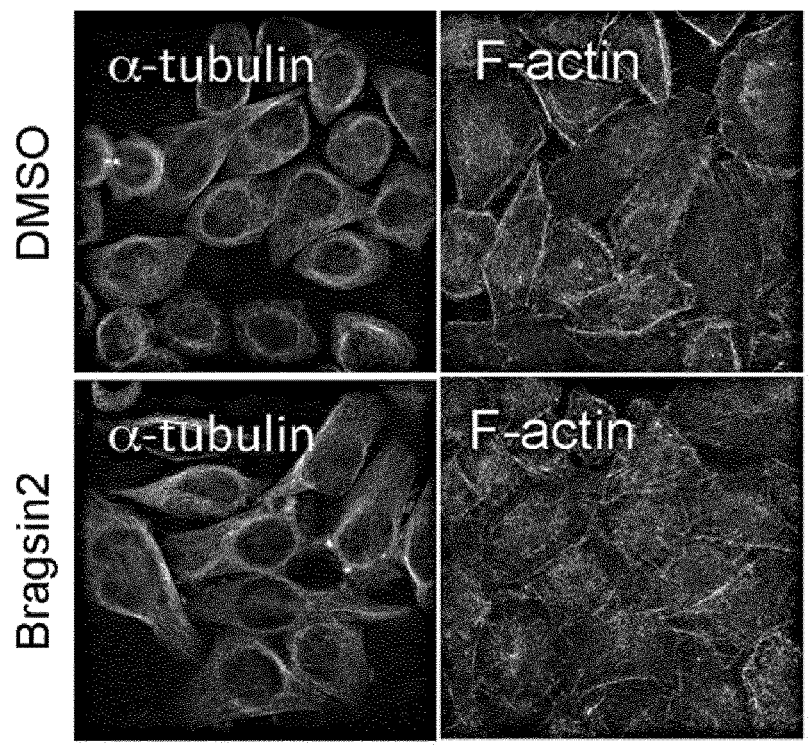

FIG. 10: Bragsin2 has no effect on the tubulin and actin networks in Hela cells. HeLa cells were treated with either DMSO (0.25%) or Bragsin2 (50 µM) for 30 min, immunostained for α-tubulin (green channel) or F-actin (magenta channel) and analysed by confocal microscopy.

FIG. 11: Bragsin1 disperses the TGN46 and GM130 markers. Hela cells were treated as in FIG. 10 with 50 µM Bragsin1 and immunostained for TGN46 or GM130 (green channel) prior to confocal microscopy analysis.

FIG. 12: Dispersion of GM130 and TGN46 by Bragsin1 is reversible. After treatment with either DMSO (0.25%) or Bragsin1 (50 µM) for 30 min, Hela cells were washed and incubated for an additional 30 min in fresh medium (wash) prior to immunostaining for TGN46 or GM130 (green channel) and confocal microscopy analysis.

FIG. 13: Expression of constitutively active Arf1, Arf5 and Arf6 constructs rescues the effect of Bragsin1. Hela cells were transiently transfected with a plasmid encoding the Q/L mutant of the indicated Arf-mCherry isoform; non transfected cells are stamped with a white asterisk. Scale bars, 10 μm.

FIGS. 14-19: Bragsin is a specific inhibitor of BRAG2

14: Representative fluorescence kinetic traces of the experiments shown in FIG. 2a. The GDP/GTP nucleotide exchange of N-terminally truncated Arf-GDP was followed in solution by tryptophan fluorescence in the presence of 50 μM of Bragsin1 (light grey) or 0.25% of DMSO (dark grey) after addition of catalytic amount of the indicated ArfGEF Sec7 domain and an excess of GTP (see material and methods for details). The spontaneous curve (black) corresponds to Arf activation in the absence of GEF.

15: Representative fluorescence kinetic traces of the experiments shown in FIG. 2b. $^{myr}$Arf1 or Rac1 activation by catalytic amount of the indicated GEF was performed as in FIG. 14 except that the experiments contained 100 μM liposomes (see material and methods for details; example 7).

16: Representative fluorescence kinetic traces of the experiments shown in FIG. 2c. $^{myr}$Arf6 activation was performed in the presence of liposomes as described in FIG. 15.

Figure 18:
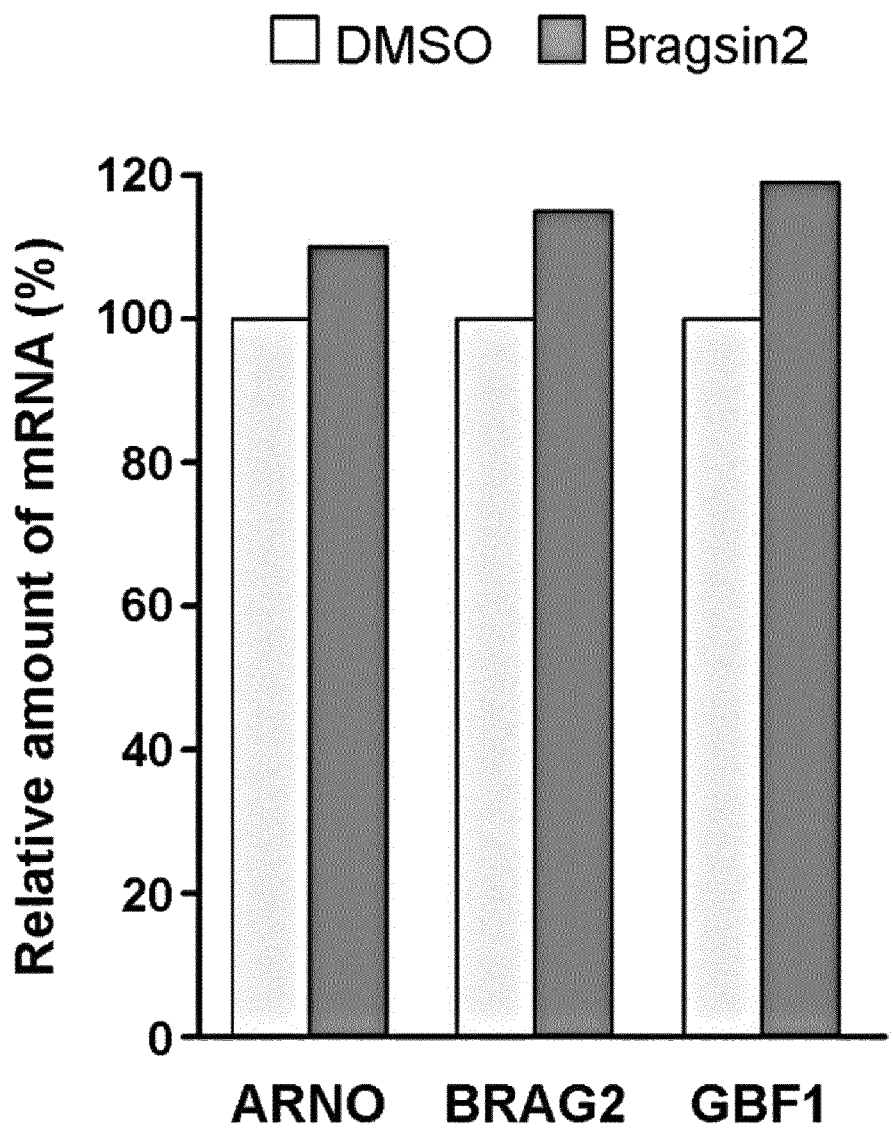

17-18: RT-qPCR analysis of ARNO, BRAG2 and GBF1 mRNA levels. HeLa cells were either transfected with siRNAs targeting BRAG2 (siBRAG2, light grey bars), ARNO (siARNO, medium grey bars), GBF1 (siGBF1, dark grey bars) or with a nontargeting siRNA (siCTRL, white bars) as a control (FIG. 17), or treated with Bragsin2 (dark grey bars) or with DMSO (white bars) as a control (FIG. 18). Total RNAs were extracted, reverse-transcribed and submitted to real-time PCR using primer pairs specific for mRNAs encoding ARNO, BRAG2 or GBF1 (as indicated below graphs). The graphs show the amounts of mRNAs relative to control values, which are set to 100%.

19: Statistical analysis of the dispersal of TGN46 staining of the experiments shown in FIG. 2e. Area of cells (polygon) and TGN (minimal ellipse) were determined manually after sum Z projection of stacks and measured using Fiji/ImageJ. Their ratio expressed the relative area (%) occupied by the TGN46 staining in the cell. Statistical analyses were done using ANOVA with Tukeýs post-test. Counted cells>200, *p<0.05, ****p<0.0001.

FIGS. 20-21:

20: Shows that Bragsin3 (compound 14) strongly inhibits BRAG2 in the presence of liposomes. Nucleotide exchange kinetics were determined in the presence of Bragsin3 (50 microM) or DMSO with BRAG2$^{Sec7PH}$ construct and myristoylated Arf1 (see material and methods for details).

21: Bragsin3 disperses the TGN46 marker. Hela cells were treated as in FIG. 1b with 50 mM Bragsin3 and immunostained for TGN46 prior confocal microscopy analysis.

FIGS. 22-29:

22: Shows the viability and cytotoxicity of Bragsine 2, Compound 14 and Compound 3 on Cell line MDA-MB-231.

23: Shows the viability and cytotoxicity of Bragsine 2, Compound 14 and Compound 3 on Cell line MCF7.

24: Shows the viability of Bragsine 2, Compound 14 and Compound 3 on Cell line SUM149.

25: Shows the viability and cytotoxicity of Bragsine 2, Compound 14 and Compound 3 on Cell line SUM159.

26: Shows the viability and cytotoxicity of Bragsine 2, Compound 14 and Compound 3 on Cell line A549.

27: Shows the viability and cytotoxicity of Bragsine 2, Compound 14 and Compound 3 on Cell line U87-MG.

28: Shows the viability and cytotoxicity of Bragsine 2, Compound 14 and Compound 3 on Cell line PANC-1.

29: Shows the viability and cytotoxicity of Bragsine 2, Compound 14 and Compound 3 on Cell line.

Viability tests (measure of the quantity of ATP after cell lysis, CelltiterGlo, Promega) and cytotocixity (measure of LDH after cell lysis, CytoTox-One, Promega).

Results in FIGS. 22-29 were analysed by one-way ANOVA followed by Tukey's multiple comparisons (vs DMSO), *P<0.05, P<0.01, *P<0.001, ****P<0.0001.

Bragsin2: 6-methoxy-5-nitro-2-(trifluoromethyl)-4H-chromen-4-one

Compound 14 (2MetO): 6,8-dimethoxy-5-nitro-2-(trifluoromethyl)-4H-chromen-4-one

Compound 3 (—NO2): 6-methoxy-2-(trifluoromethyl)-4H-chromen-4-one (negative control).

The present invention is further illustrated by means of the following examples.

The data presented in these examples, and also in parts of the patent description, are in part taken from preliminary analysis and as such represent a close approximation to the final, validated dataset. However, this fully supports the present invention.

Other aims, characteristics and advantages of the invention will appear clearly to the person skilled in the art upon reading the explanatory description which makes reference to the Examples which are given simply as an illustration and which in no way limit the scope of the invention.

The Examples make up an integral part of the present invention, and any characteristic which appears novel with respect to any prior state of the art from the description taken in its entirety, including the Examples, makes up an integral part of the invention in its function and in its generality.

Thus, every example has a general scope.

Furthermore, in the Examples, all percentages are given by mass, unless indicated otherwise, temperature is expressed in degrees Celsius unless indicated otherwise, and the pressure is atmospheric pressure, unless indicated otherwise.

EXAMPLES

A small molecule Bragsin1 was originally discovered in a yeast chemogenomic screen; Bragsin perturbs the function of the yeast ArfGEF Sec7p, and a related analog, such as Bragsin2 or molecules according to the present invention, especially as defined by any of the claimed structures, referred to collectively as Bragsin (FIG. 1a). Bragsin is a specific inhibitor of the ArfGEF BRAG2 in vitro and in cells. Cell-based assays and in vitro reconstitution of GEF activities in artificial membranes using pure proteins were performed. Bragsin is a non-competitive inhibitor, which binds at the GEF/membrane interface and acts to orient the GEF on the membrane in a manner that makes BRAG2 incompetent for nucleotide exchange activity according to crystallographic analysis coupled to structure-activity relationship (SAR) analysis. Consistent with a role of BRAG2 in breast cancer, Bragsin depletes the cancer stem cell population in mammary tumor cell lines. Bragsin is as a novel type of inhibitor that targets protein-membrane interactions with potential in breast cancer treatment.

Example 1—Bragsin Inhibits the Activation of Arf GTPases in Cells

Bragsin1 may affect Arf pathways in cells because Bragsin 1 perturbs the function of the yeast ArfGEF Sec7p. Bragsin1 was found to be chemically unstable after a few days in aqueous solution leading to a biologically inactive hydrated derivative. A related analog bearing a methoxy group instead of a methyl group (Bragsin2) was resistant to hydration and stable (FIGS. 7-9). In initial experiments Bragsin2 was used to assess possible effects on the structure of the cis-Golgi and trans-Golgi network (TGN) compartments, which are regulated by Arf-dependent pathways. In Hela cells, the cis-Golgi marker GM130 and the TGN marker TGN46 was dispersed by Bragsin2 into punctate structures of heterogeneous sizes (FIG. 1b), and this effect was reversible (FIG. 1c). In contrast, Bragsin2 had no effect on the early endosome marker EEA1 (FIG. 1b) nor did it affect tubulin and actin networks (FIG. 10). Cells were transfected with Arf-mCherry constructs carrying a QL mutation that makes Arf constitutively active to assess if this effect was mediated via interference with Arf GTPase pathways,. Arf1, Arf5 and Arf6 expression rescued Bragsin2-induced dispersion of the TGN46 compartment, consistent with an effect of the compound on Arf pathways (FIG. 1d). The phenotypes of cells treated with freshly prepared Bragsin1 were identical to those treated with Bragsin2 (FIG. 11), were reversible (FIG. 12) and rescued by expression of constitutively active Arf GTPases (FIG. 13). Together, these data suggest that Bragsin1 and Bragsin2 inhibit Arf pathways in cells, in agreement with the original activity observed in a chemogenomic screen of Bragsin1 towards the yeast ArfGEF Sec7p.

Example 2—Bragsin is a Specific Inhibitor of BRAG2 that Necessitates the Presence of Membranes for Inhibition Arf GTPases are activated in human cells, by several ArfGEF subfamilies, all of which contain a conserved Sec7 domain decorated with variable appended domains (Nastou, K. C., Tsaousis, G. N., Kremizas, K. E., Litou, Z. I. & Hamodrakas, S. J. The human plasma membrane peripherome: visualization and analysis of interactions. *Biomed Res Int* 2014, 397145 (2014); DiNitto, J. P. et al. *Mol Cell* 28, 569-83 (2007)).

Figure 14:
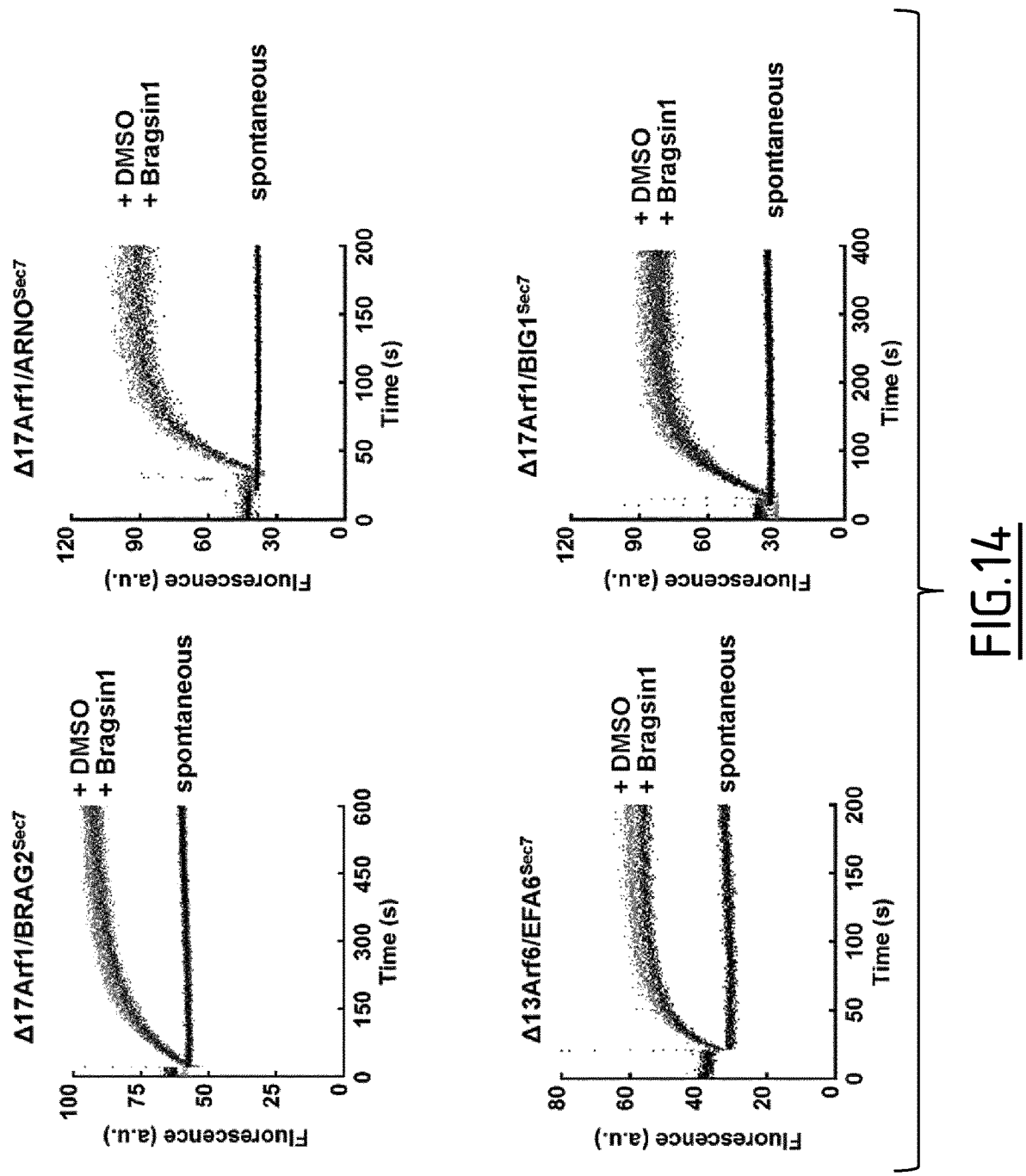
Figure 15:
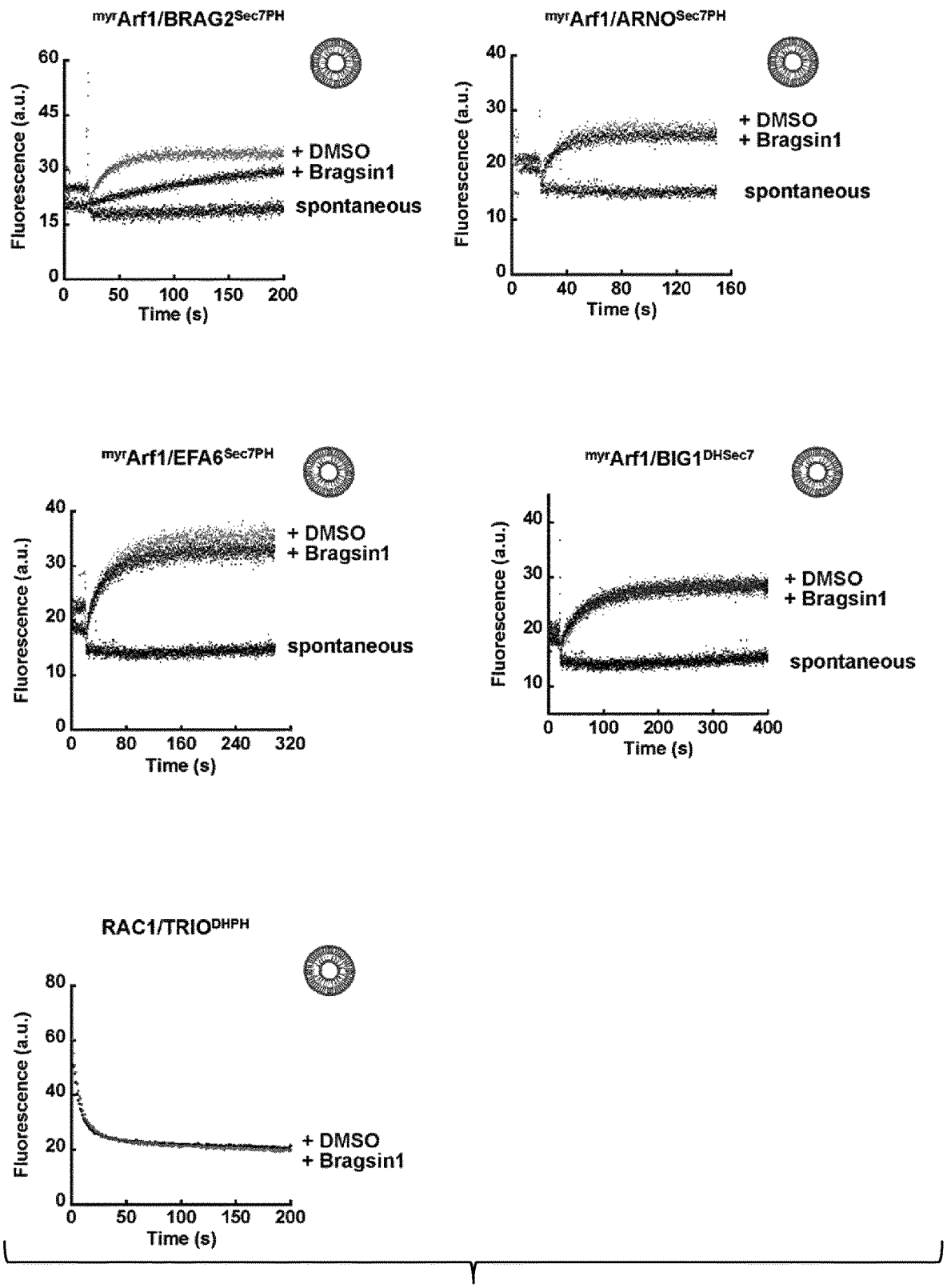
Figure 16:
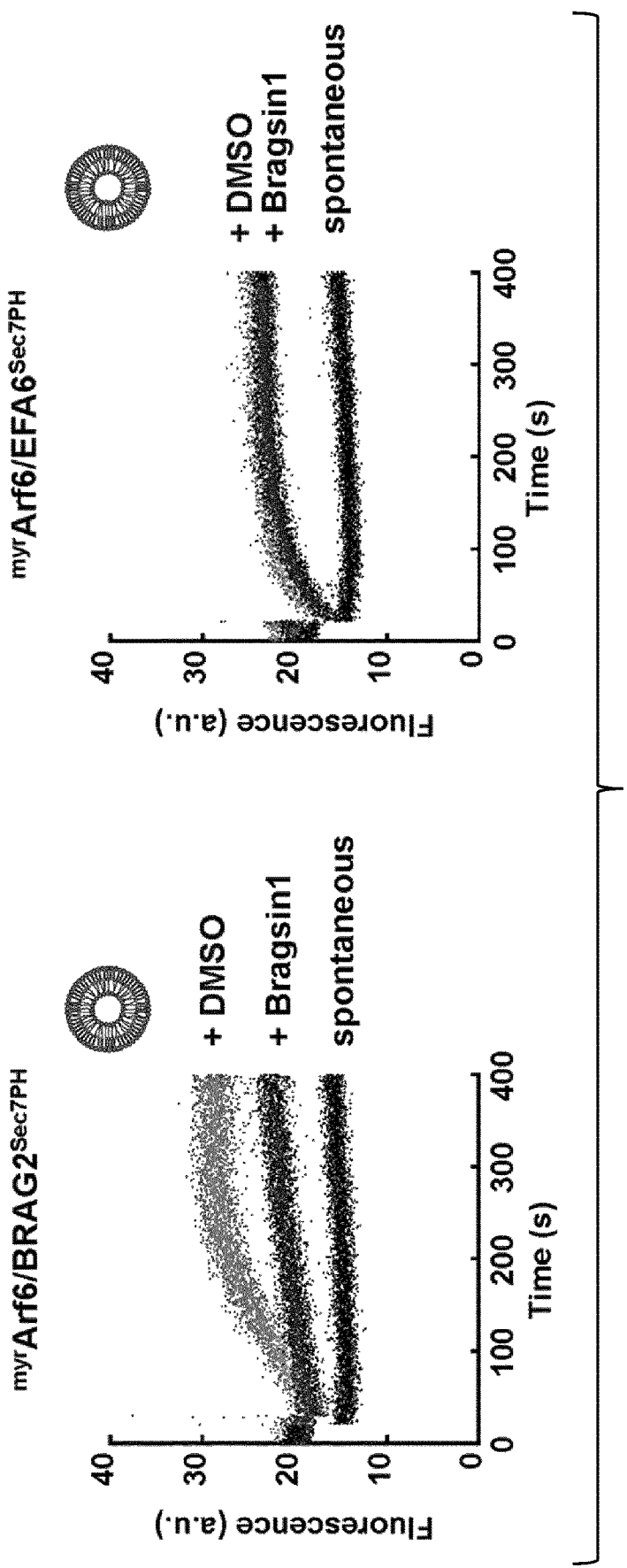

The effect of Bragsin1 on the GEF efficiency of representative human ArfGEFs was evaluated by fluorescence kinetics using highly purified recombinant Arf GTPases and ArfGEFs. In a first series of assays, the Sec7 domains of BIG1, a Golgi ArfGEF, and of ARNO, EFA6a and BRAG2, which function at the plasma membrane, were used. When tested in solution, Bragsin1 had no effect on the activation of Arf1 by any of these Sec7 domains (FIGS. 2a and 14). Separately, we reconstituted the activation of myristoylated Arf1 by the same ArfGEFs on liposomes using ArfGEF constructs that contain a membrane-binding domain (DCB-HUS domain for BIG1, PH domains for the other GEFs). Remarkably, Bragsin1 strongly inhibited BRAG2 on liposomes, while it had no effect on the other ArfGEFs (FIGS. 2b and 15) or on Rac1/Trio, an unrelated small GTPase/GEF system (FIGS. 2b and 15). BRAG2 activates several Arf isoforms, including the plasma membrane-located Arf6 isoform. Bragsin1 also inhibited the BRAG2-mediated activation of myristoylated Arf6, indicating that inhibition is independent of the Arf isoform used (FIGS. 2c and 16). Bragsin1 and Bragsin2 have the same $IC_{50}$ towards BRAG2 (3 mM) according to dose-response analysis, confirming that Bragsin1 and Bragsin2 can be used interchangeably (FIG. 2d). The specific inhibition of BRAG2 by Bragsin in vitro predicts that BRAG2 silencing by siRNA should yield the same phenotype as treatment by the small molecule. Silencing of BRAG2 induced the redistribution of TGN46 into tubular or punctate structures, which phenocopied the effects induced by Bragsin (FIGS. 2e, 17 and 18). As a control, silencing of the Golgi ArfGEF GBF1 resulted in a markedly different phenotype, in which TGN46 was either concentrated into punctate structures or became diffuse throughout the cytosol. Silencing of ARNO, which is located at the plasma membrane, had no effect on TGN46 distribution. Overexpression of BRAG2-mCherry rescued the dispersion of the TGN46 structure induced by Bragsin, which is consistent with the silencing experiments (FIG. 2f). Bragsin is a specific inhibitor of the ArfGEF BRAG2 in vitro and in cells according to these experiments. These oexperiments identify a mechanism of inhibition that requires the membrane to manifests itself.

Example 3—Bragsin Binds to the PH Domain of BRAG2

In vitro and cellular assays support that the $BRAG2^{Sec7-PH}$ construct used in vitro recapitulates the inhibitory effects seen with full-length BRAG2 in cells. This construct was used to obtain the crystal structure of the $BRAG2^{Sec7-PH}$ Bragsin1 complex (Table 1). Unambiguous electron density was observed near the PH domain in which the inhibitor could be modeled (FIG. 3a), and its position was not involved in crystal contacts. Bragsin1 interacts with the PH domain by a combination of polar and hyrdophobic contacts involving Leu 651, His 652 and Arg 654 in strand b1, Lys 667 in strand b3 and Arg 681 in strand b4 (FIG. 3b). $CF_3$ and carbonyl groups of Bragsin2 interact with the PH domain, but not the methyl group, which explains why, where this latter group is replaced by a methoxy group, is as potent as Bragsin1. Conversely, hydration of Bragsin1 leading to a sp3 geometry and a different orientation of the carbon bearing the $CF_3$ substituent, was in agreement with the loss of activity of Bragsin1 over time (see above). R654E or R681E mutations were introduced in the PH domain of BRAG2 to confirm the location of the binding site, the. Inhibition was affected for both mutants (FIG. 3c). The R681E mutation rendered BRAG2 insensitive to Bragsin and, interestingly, the R654E mutant was more inhibited by Bragsin than the wild type BRAG2. Next, Bragsin analogs were synthesized wherein $NO_2$ or $CF_3$ functional groups, which establish interactions with BRAG2 in the crystal, were removed or modified (compounds (3) to (6), FIG. 1a and Example 6). All analogs displayed reduced inhibition of BRAG2 in vitro (FIG. 3d) and were not capable to disperse TGN46 (compounds 3, 4, and 6) or had less effect (compound 5) in cells (FIG. 3e). Together, the crystallographic, mutagenesis and structure-activity relationship analyses consistently pinpointed a specific binding site for Bragsin within the PH domain of BRAG2.

Example 4—Bragsin is a Non-Competitive Inhibitor of BRAG2/Membrane Interactions

Bragsin may partially overlap with a lipid bound at this position was predicted by comparison of the PH domain of a cytohesin ArfGEF with a phosphoinositide headgroup bound to the canonical lipid-binding site (DiNitto, J. P. et al. *Mol Cell* 28, 569-83 (2007))(FIG. 4a). Bragsin inhibition could act by blocking the interaction of BRAG2 with membranes. Surprisingly, Bragsin2 did not displace BRAG2 from $PIP_2$-containing liposomes, showing that it does not inhibit BRAG2 by disrupting its association with the membrane (FIG. 4b). Alternatively, Bragsin may bind at the interface between the PH domain and the membrane if inhibition is sensitive to the lipid composition of the membrane. Using liposomes that support strong BRAG2 activity, inventors found that Bragsin2 inhibits BRAG2 more efficiently on liposomes that contain $PIP_2$ compared to liposomes that contain PS as the sole negatively charged lipids (FIG. 4c). These experiments support that Bragsin inhibits BRAG2 by binding at the interface between BRAG2 and the lipid bilayer in a non-competitive manner, causing a mode of binding of BRAG2 that is not competent for promoting nucleotide exchange on membrane-attached myristoylated Arf.

Example 5—Bragsin Affects Breast Cancer Stem Cells

Cancer stem cells represent the cell population that sustains tumor growth, metastasis, resistance to chemo- and radio-therapies and recurrence after treatment. Targeting stem cell populations has become a key step in the design of efficient anticancer strategies because their relative abundance in tumors correlates with poor prognosis in patients. It was tested whether Bragsin affects breast cancer stem cells (bCSCs) as BRAG2 has been reported to be involved in breast cancer cell invasion (Morishige, M. et al. GEP100 links epidermal growth factor receptor signalling to Arf6 activation to induce breast cancer invasion. *Nat Cell Biol* 10, 85-92 (2008)). It was first evaluated the effect of Bragsin on the bCSC population in three different breast cancer cell lines (SUM159, SUM149, S68), using aldehyde dehydrogenase ($ALDH^{br}$) activity as a marker of the malignant bCSC population (Charafe-Jauffret, E. et al. ALDH1-positive cancer stem cells predict engraftment of primary breast tumors and are governed by a common stem cell program. *Cancer Res* 73, 7290-300 (2013); Ginestier, C. et al. ALDH1 is a marker of normal and malignant human mammary stem cells and a predictor of poor clinical outcome. *Cell Stem Cell* 1, 555-67 (2007). Bragsin treatment (50 µM) depleted the bCSC population in two of the three cell lines tested (SUM149 and S68) (FIG. 5a). A single-cell tumorsphere formation assay was performed to functionally validate these observations. A marked decrease was observed in tumorsphere-forming efficiency (SFE) in SUM149 and S68 cell lines following treatment by Bragsin, consistent with the depletion of the bCSC $ALDH^{br}$ population (FIG. 5b). In contrast, the SUM159 cell line, whose bCSC $ALDH^{br}$ activity was not decreased by Bragsin, presented a similar SFE, whether they were treated by Bragsin or not. Together, these results indicate that Bragsin may target the bCSC population of some breast cancers.

Example 6—Synthesis of Bragsin1, Bragsin 2 and Analogs Used in this Study (FIG. 1a)

6.1. General Information

Unless otherwise stated, all glassware was flame-dried or oven dried before use and all reactions were performed under an atmosphere of argon. Dichloromethane, acetonitrile, toluene, methanol and DMSO were purchased from Sigma-Aldrich anhydrous grade and used as received; all other solvents are distilled before use. All reagents were used as received from commercial suppliers unless stated otherwise. Reaction progress was monitored by thin layer chromatography (TLC) performed on aluminium plates coated with silica gel $F_{254}$. Visualization was achieved by fluorescence quenching with UV light at 254 nm or by staining using potassium permanganate, phosphomolibdic acid solution, p-anisaldehyde solution or vanillin solution and heating. Flash column chromatography was performed using silica gel 60 (230-400 mesh, Merck and co.). $^1H$ NMR and $^{13}C$ NMR spectra were recorded using a Bruker AV-300, AV-400 and AV-500 spectrometer at 300K. Chemical shifts were given in parts per million (ppm, δ), referenced to the solvent peak of $CDCl_3$, defined at δ=7.26 ppm ($^1H$ NMR) and δ=77.16 ($^{13}C$ NMR). Coupling constants are quoted in Hz (J). $^1H$ NMR splitting patterns are designated as singlet (s), doublet (d), doublet of doublet (dd), triplet (t), quartet (q), pentet (p). Splitting patterns that could not be interpreted or easily visualized are designated as multiplet (m) or broad (br).

6.2. Experimental Procedures

Synthesis of Bragsin1, Bragsin2 and Compound (3)

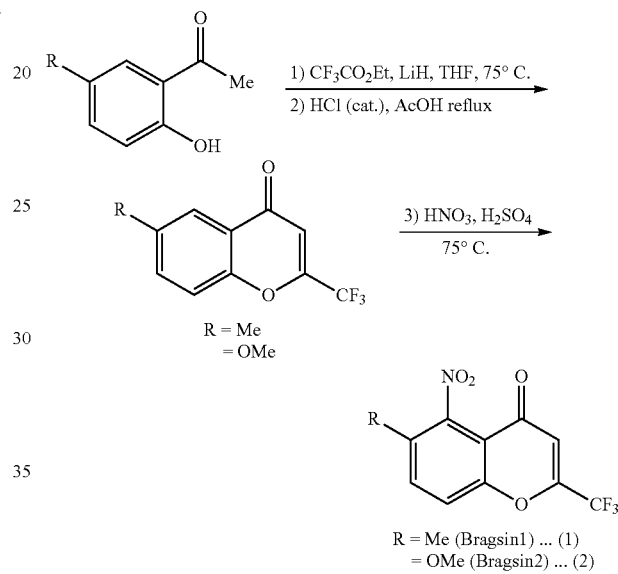

6.2.1. General Procedure
Step 1 and 2

Dry THF (1.5 ml) and finely dispersed LiH (3.4 equivalent) were placed in a round-bottom two-necked flask under argon and the mixture was brought to reflux. A solution of the desired ketone (1.0 equivalent) and ethyl 2,2,2-trifluoroacetate (1.5 equivalent) in dry THF was added over 10-15 min, under stirring. The mixture was refluxed for 2 h and then quenched with an aqueous solution of aqueous 1 N HCl. The reaction mixture was extracted with EtOAc three times and the organic layers were combined, washed with brine, dried over $MgSO_4$, filtered, and concentrated under reduced pressure vacuo. The product was used in the next step without further purifications.

A drop of a 37% aq. HCl solution was added to a solution containing the reaction product obtained after step 1 (1.0 equivalent) in acetic acid (5 ml), under stirring and the solution was refluxed for 1 h. After this time, the reaction was diluted with water and the solvent was removed under vacuum. The crude mixture was obtained and purified by column chromatography (cyclohexane:ethyl acetate, gradient from 0% to 60% ethyl acetate) to deliver designed chromenone derivatives.

Step 3

A mixture of concentrated $H_2SO_4$ (0.6 ml) and concentrated $HNO_3$ (0.6 ml) was added to a solution of purified product from step 2 (1 equiv) in conc. $H_2SO_4$ (2 ml). The reaction mixture was stirred at 75° C. for 35 min and then diluted with ice-cold water. The reaction mixture was extracted by using ethyl acetate 3 times, washed with brine, dried over MgSO$_4$, filtered and concentrated under reduced pressure. The crude mixture was purified by chromatography (reverse/normal phase) to deliver designed nitro-chromenone products.

6-methyl-5-nitro-2-(trifluoromethyl)-4H-chromen-4-one (Bragsin1, FIG. 1a)

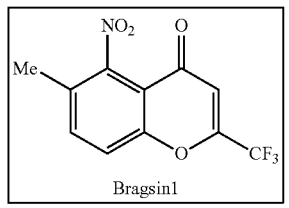

The title compound was prepared from commercially available 2'-hydroxy-5'-methylacetophenone, according to general procedure. Bragsin1 was obtained in 11% yield (in 3 steps). Data is in accordance with the literature. $^1$H-NMR (500 MHZ, CDCl$_3$): δ 7.71 (d, J=8.9 Hz, 1H), 7.63 (d, J=8.9 Hz, 1H), 6.74 (s, 1H), 2.39 (s, 3H).

6-methoxy-5-nitro-2-(trifluoromethyl)-4H-chromen-4-one (Bragsin2, FIG. 1a)

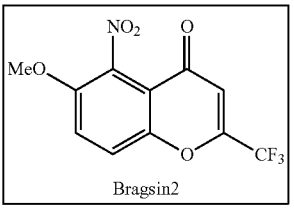

The title compound was prepared from commercial available 2'-hydroxy-5'-methoxyacetophenone, according to general procedure. Bragsin2 was obtained in 78% yield (in 3 steps). Data is in accordance with the literature. $^1$H-NMR (500 MHz, CDCl$_3$): δ 7.71 (d, J=9.5 Hz, 1H), 7.54 (d, J=9.5 Hz, 1H), 6.70 (s, 1H), 3.98 (s, 3H).

6-methoxy-2-(trifluoromethyl)-4H-chromen-4-one (3) (compound 3, FIG. 1a)

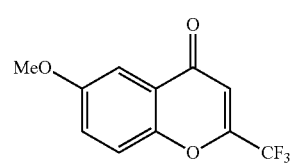

The title compound was prepared from commercial available 2'-hydroxy-5'-methoxyacetophenone, according to general procedure (step 1 and 2). Compound 3 was obtained in 90% yield (in 2 steps). Data is in accordance with the literature. $^1$H-NMR (300 MHZ, CDCl$_3$): δ 7.54 (d, J=3.1 Hz, 1H), 7.48 (d, J=9.2 Hz, 1H), 7.34 (dd, J=9.2, 3.1 Hz, 1H), 6.70 (s, 1H), 3.91 (s, 3H).

Quality Analysis of Compound (4) (Compound 4, FIG. 1a)

6-methoxy-5-nitro-2-(trifluoromethyl)-4H-chromen-4-one (4)

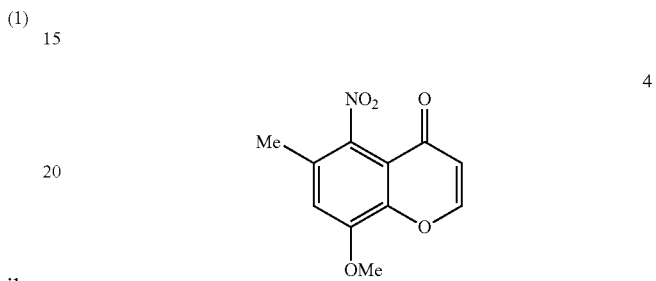

The title compound is commercial available compound (CAS: 354128-13-5). $^1$H-NMR (500 MHZ, CDCl$_3$): δ 7.88 (d, J=6.0 Hz, 1H), 7.00 (s, 1H), 6.37 (d, J=6.0 Hz, 1H), 4.03 (s, 3H), 2.37 (s, 3H).

Synthesis of Compound (5) (Compound 5, FIG. 1a)

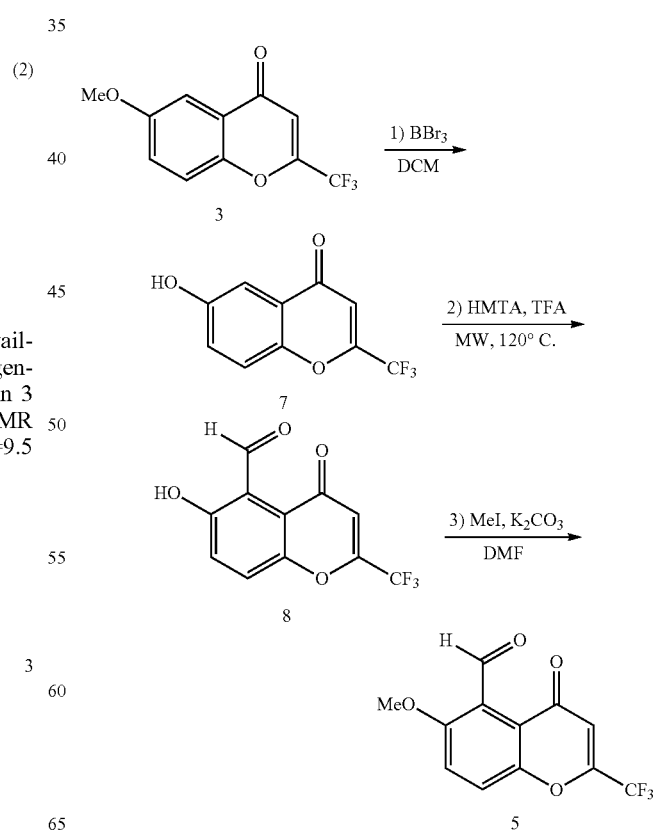

6-hydroxy-2-(trifluoromethyl)-4H-chromen-4-one (7)

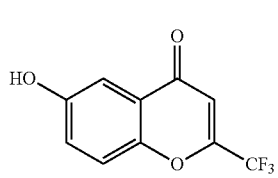

Chromenone 3 (0.1 g, 0.41 mmol, 1.0 equiv.) was dissolved in DCM. Over the reaction mixture was added dropwise 1 mL of BBr$_3$ (1M, 0.82 mmol, 2.0 equiv.) at 0° C. The reaction was stirred at room temperature for 2 hours. Then, it was quenched with water, extracted with DCM, washed with NaHCO$_3$ and dried over MgSO$_4$. The volatiles were removed under reduced pressure. The collected residues were purified via column chromatography (hexane: EtOAc=1:2). Compound 7 was obtained in 69% yield (65 mg, 0.28 mmol). $^1$H-NMR (300 MHZ, CDCl$_3$): δ 7.84 (d, J=3.0 Hz, 1H), 7.50 (d, J=9.2 Hz, 1H), 7.38 (dd, J=9.2, 3.0 Hz, 1H), 6.75 (s, 1H). $^{13}$C-NMR (75 MHZ, CDCl$_3$): δ 178.2, 155.3, 152.9 (q, J=39.2 Hz), 150.4, 125.2, 124.7, 120.1, 118.7 (q, J=274.2 Hz), 109.4 (q, J=2.8 Hz), 109.2. HRMS (ESI): calculated for C$_{10}$H$_6$F$_3$O$_3$ [M+H]$^+$: 231.0259, found: 231.0264.

6-hydroxy-4-oxo-2-(trifluoromethyl)-4H-chromene-5-carbaldehyde (8)

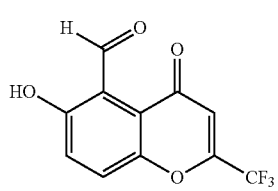

A mixture of chromenone 7 (100 mg, 0.44 mmol, 1.0 equiv.) and hexamethylenetetramine (121.9 mg, 0.87 mmol, 2.0 equiv.) was dissolved in TFA (2 ml). The mixture was heated up at 120° C. in microwave equipment for 30 minutes. Then, the reaction was cooled to room temperature and quench with ice water, extracted with Et$_2$O and dried over MgSO$_4$. After the solvent was removed, the collected residues were purified via column chromatography (hexane: EtOAc=3:2). Compound 8 was obtained in 48% yield (55 mg, 0.21 mmol). $^1$H-NMR (300 MHZ, CDCl$_3$): δ 13.09 (s, 1H), 11.43 (s, 1H), 7.75 (d, J=9.4 Hz, 1H), 7.43 (d, J=9.4 Hz, 1H), 6.78 (s, 1H). $^{13}$C-NMR (75 MHZ, CDCl$_3$): δ 198.6, 178.1, 162.5, 151.3 (q, J=39.2 Hz), 150.3, 128.0, 127.2, 122.4, 118.5 (q, J=273.9 Hz), 115.4, 111.8 (q, J=2.7 Hz). HRMS (ESI): calculated for C$_{11}$H$_6$F$_3$O$_4$ [M+H]$^+$: 259.0218, found: 259.0212.

6-methoxy-4-oxo-2-(trifluoromethyl)-4H-chromene-5-carbaldehyde (5) (compound 5, FIG. 1a)

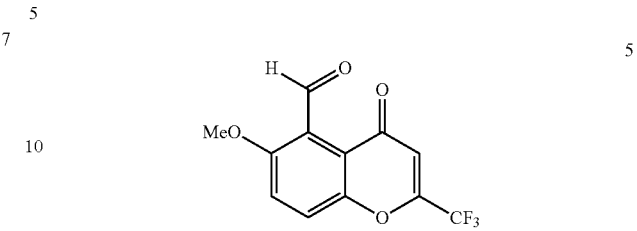

Under argon, compound 8 (50 mg, 0.19 mmol, 1.0 equiv.) was dissolved in dry DMF followed by the addition of K$_2$CO$_3$ (80 mg, 0.582 mmol, 3.0 equiv.) at 0° C. Then, methyl iodide (15 μL, 0.23 mmol, 1.2 equiv.) was added dropwise to the mixture at 0° C. The reaction was stirred for 12 hours at room temperature. The mixture was quenched with NH4Cl, extracted with ethyl acetate, washed with brine and dried over MgSO$_4$. The organic layers were combined and the volatiles were removed under reduced pressure. The crude product was purified via column chromatography (hexane: EtOAc, 3:2) to afford the titled product in 86% yield (55 mg, 0.21 mmol). $^1$H-NMR (300 MHZ, CDCl$_3$): δ 10.57 (s, 1H), 7.67 (d, J=9.3 Hz, 1H), 7.46 (d, J=9.3 Hz, 1H), 6.67 (s, 1H), 3.91 (s, 3H). $^{13}$C-NMR (75 MHz, CDCl$_3$): δ 191.9, 177.5, 154.7, 152.5 (q, J=39.4 Hz), 149.6, 126.0, 123.6, 121.9, 120.0, 118.6 (q, J=274.2 Hz), 110.0 (q, J=2.8 Hz), 57.1. HRMS (ESI): calculated for C$_{12}$H$_8$F$_3$O$_4$ [M+H]$^+$: 273.0374, found: 273.0369.

Synthesis of Compound (6) (Compound 6, FIG. 1a)

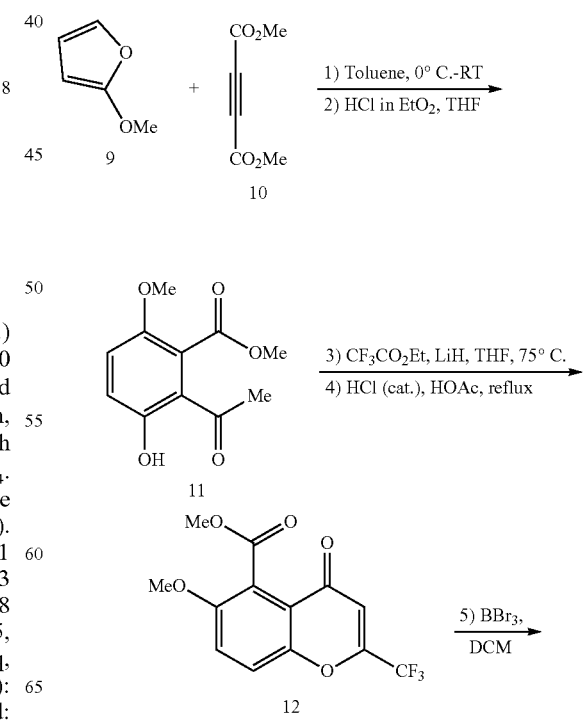

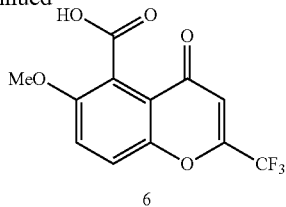

methyl 2-acetyl-3-hydroxy-6-methoxybenzoate (11)

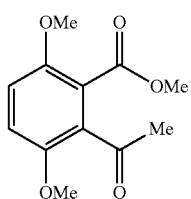

To a stirred solution of furan 9 (389 mg 3.96 mmol, 1.0 equiv.) toluene (1.5 mL) at 0° C. was added keto ester 10 (500 mg, 3.96 mmol, 1.0 equiv.) in one portion. Upon complete addition the amber solution was allowed to warm to 90° C. After 1 hour the reaction mixture was concentrated in vacuo to give a bicyclic mixture as 1:3 regioselectivity (observed by NMR) as viscous burgundy oil. To a stirred solution of this bicyclic mixture (875 mg, 3.97 mmol, 1.0 equiv.) in THF (4 mL) was slowly added a solution of dry hydrochloric acid in ether (1.0 M, 0.8 mL, 0.78 mmol, 0.2 equiv.) at 0° C. over 5 min. Upon complete addition the amber solution was allowed to warm to room temperature. After 2 hours the reaction mixture was concentrated in vacuo to give an amber oil. The crude material (412 mg, 43% yield over 2 steps) was purified via silica gel column chromatography (hexane:EtOAc, 10:1) to give product 11 (89 mg) as a clear light yellow oil. $^1$H-NMR (300 MHZ, CDCl$_3$): δ 11.91 (s, 1H), 7.17 (d, J=9.2 Hz, 1H), 7.04 (d, J=9.2 Hz, 1H), 3.95 (s, 3H), 3.81 (s, 3H), 2.52 (s, 3H). $^{13}$C-NMR (75 MHZ, CDCl$_3$): δ 203.8, 168.6, 156.5, 149.1, 124.0, 121.3, 121.0, 117.5, 57.7 53.2, 29.3. HRMS (ESI): calculated for C$_{11}$H$_{12}$O$_5$Na [M+Na]$^+$: 247.0582, found: 247.0580.

methyl 6-methoxy-4-oxo-2-(trifluoromethyl)-4H-chromene-5-carboxylate (12)

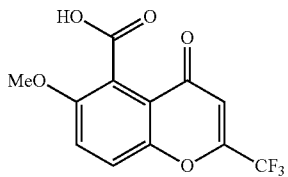

The title compound was prepared from benzoquinone 11, according to general procedure. Compound 12 was obtained in 85% yield. $^1$H-NMR (300 MHZ, CDCl$_3$): δ 7.63 (d, J=9.4 Hz, 1H), 7.42 (d, J=9.4 Hz, 1H), 6.65 (s, 1H), 4.01 (s, 3H), 3.93 (s, 3H). $^{13}$C-NMR (75 MHZ, CDCl$_3$): δ 176.0, 166.9, 154.2, 152.0 (q, J=39.4 Hz), 149.6, 121.9, 120.7, 120.4, 119.0, 118.6 (q, J=274.5 Hz), 109.9 (q, J=2.7 Hz), 57.0, 53.3. HRMS (ESI): calculated for C$_{13}$H$_{10}$F$_3$O$_5$ [M+H]$^+$: 303.0430, found: 303.0475.

6-methoxy-4-oxo-2-(trifluoromethyl)-4H-chromene-5-carboxylic acid (6) (compound 6, FIG. 1a)

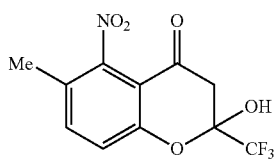

Chromenone 12 (50 mg, 0.16 mmol, 1.0 equiv.) dissolved in DCM. Over the reaction mixture was added dropwise 0.3 mL of BBr$_3$ (1 M, 0.33 mmol, 2.0 equiv.) at 0° C. The reaction was stirred at room temperature for 1 hour. Then, it was quenched with water, extracted with DCM, washed with NaHCO$_3$ and dried over MgSO$_4$. The volatiles removed under reduced pressure. The collected residues were purified via column chromatography (hexane: EtOAc=2:3). After chromatography separation, compound 6 was obtained in 22 mg (46% yield) as white solid. $^1$H-NMR (300 MHZ, CDCl$_3$): δ 7.56 (d, J=9.3 Hz, 1H), 7.40 (d, J=9.3 Hz, 1H), 6.69 (s, 1H), 3.96 (s, 3H). $^{13}$C-NMR (75 MHZ, CDCl$_3$): δ 175.6, 168.8, 154.8, 151.7 (q, J=39.3 Hz), 150.2, 125.3, 122.9, 122.8, 118.6 (q, J=274.3 Hz), 113.3, 110.7 (q, J=2.7 Hz), 53.3. HRMS (ESI): calculated for C$_{12}$H$_8$F$_3$O$_5$ [M+H]$^+$: 289.0324, found: 289.0317.

2-hydroxy-6-methyl-5-nitro-2-(trifluoromethyl)chroman-4-one (13)

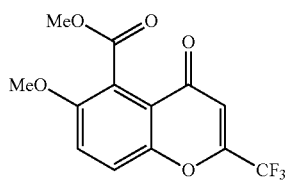

Data is in accordance with the literature $^1$H-NMR (300 MHz, CDCl$_3$): δ 7.49 (d, J=8.6 Hz, 1H), 7.15 (d, J=8.6 Hz, 1H), 5.71 (s (br), 1H, OH), 3.10 (q, J=9.6 Hz, 2H), 2.24 (s, 3H).

6,8-dimethoxy-5-nitro-2-(trifluoromethyl)-4H-chromen-4-one (14)

Step 1
Charge Pd(OAc)$_2$ (4.4 mg, 0.02 mmol), K$_2$S$_2$O$_8$ (216 mg, 0.8 mmol) in a 4 mL intillation vial, followed by 2 mL TFA and ketone substrate (0.4 mmol). Seal the reaction with a teflon-lined cap. Heat the reaction at 50° C. for 1.5 hours on a pie block. Monitor the reaction by TLC. Remove the solvent in vacuo. Subject the residue to flash chromatography (silica gel) using Hex/DCM to obtain hydroxy-3Ê$^1$,5Ê$^1$-dimethoxyacetophenone.

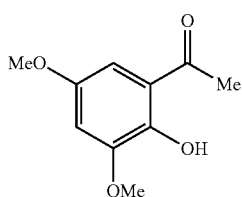

$^1$H-NMR (400 MHZ, CDCl$_3$): δ 12.21 (s, 1H), 6.69 (d, J=0.7 Hz, 2H), 3.86 (s, 3H), 3.79 (s, 3H), 2.61 (s, 3H)

General Procedure

Step 2

Dry THF (1.5 ml) and finely dispersed LiH (3.4 equivalent) were placed in a round-bottom two-necked flask under argon and the mixture was brought to reflux. A solution of containing, corresponding ketone, commercial starting material (1.0 equivalent) and ethyl 2,2,2-trifluoroacetate (1.5 equivalent) in dry THF was added over 10-15 min, under stirring. The mixture was refluxed for 2 h and then quenched with an aqueous solution of aqueous 1 N HCl. The reaction mixture was extracted with EtOAc three times and the organic layers were combined, washed with brine, dried over MgSO$_4$, filtered, and concentrated in vacuo. The product was used in the next step without further purifications.

Step 3

One drop of conc. HCl was added to a solution of crude from step 1 (1.0 equivalent) in acetic acid, under stirring and the solution was refluxed for 1 h. After this time, the reaction was diluted with water and the solvent was removed under vacuum. The crude mixture was obtained and purified by chromatography to deliver designed chromenone derivatives.

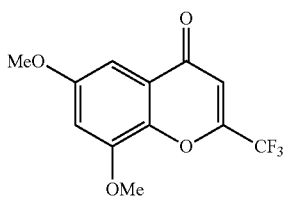 [SMILES: COc1cc(OC)c2oc(C(F)(F)F)cc(=O)c2c1]

Step 4 (Nitration)

A mixture of conc. H2SO4 (0.6 ml) and conc. HNO3 (0.6 ml) was added to a solution of purified product from step 2 (1 equiv) in conc. H2SO4 (2.3 ml). The reaction mixture was stirred at 75° C. for 35 min and then diluted with ice-cold water. The precipitate was filtered off, washed with water, dried and recrystallized from BuOH. Compound 14 (Bragsin3) was obtained as a white crystal solid.

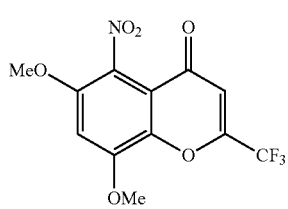

14

Example 7—Material and Methods 7.1. Chemicals.

Nucleotides were purchased from Jena Bioscience. BFA was from Sigma. Bragsin1 (6-methyl-5-nitro-2-(trifluoromethyl)-4H-chromen-4-one) and Bragsin2 (6-methoxy-5-nitro-2-(trifluoromethyl)-4H-chromen-4-one) were purchased from Vitas-M laboratory, further purified and analyzed as described in example 6. Analysis of the stability of Bragsin1 and Bragsin2 is shown in FIGS. 7-9. Bragsin1 became commercially unavailable in the course of this study, and some experiments were therefore carried out only with Bragsin2 (effect on BRAG2 mutants-FIG. 3*c*, effect on BRAG2 membrane binding-FIG. 4*b*, and effect of membrane composition on Bragsin efficiency-FIG. 4*c*). Bragsin1 and Bragsin2 can be used indifferently. Synthesis of Bragsin analogs shown in FIG. 1*a* is described in example 6.

7.2. Antibodies and cDNAs.

Mouse monoclonal anti-GM130 (cis-Golgi matrix protein of 130 kDa) and anti-EEA1 (early endosome antigen 1) were from Transduction Laboratories. Mouse monoclonal anti-α-tubulin was from Sigma. Sheep antibody against TGN46 (trans-Golgi network protein of 46 kDa) was purchased from AbD Serotec. Alexa 647-labelled phalloidin was from Invitrogen. For secondary antibodies, Alexa 488-conjugated with goat anti-mouse or donkey anti-sheep IgGs (Invitrogen) was used for immunofluorescence and horseradish peroxidase-conjugated chicken anti-mouse IgG (Santa Cruz Biotechnology) was used for Western blotting. Plasmids encoding full-length Arf1 Q71L, Arf5 Q71L and Arf6 Q67L mutants were kindly provided by Julie Ménétrey (LEBS, CNRS, Gif-sur-yvette, France) and used as templates for sub-cloning in the pmCherry-N1 vector (Clontech) for expression of mCherry C-terminal fusion mutant proteins in mammalian cells. Full-length sequence coding for human BRAG2b (1-963) was synthetized by ProteoGenix and sub-cloned into pmCherry-N1 (Clontech) for transient expression of BRAG2-mCherry in mammalian cells. BRAG2$^{Sec7PH}$ mutants were generated by site-directed mutagenesis using Quickchange kit (Stratagene) as per manufacturer's protocol.

7.3. Cell Culture, Transfection and Treatment with Inhibitors.

Hela cells were grown in Dulbecco's modified Eagle's medium supplemented with Glutamax™ and 10% fetal bovine serum (Invitrogen). For immunofluorescence studies, cells were grown on Labtek glass slides (Nunc) and transfected for 18 to 24 h using Lipofectamine 2000 (Invitrogen), according to the supplier's instructions. When specified, cells were treated with the indicated concentration of small molecule or corresponding volume of vehicle (DMSO) in growth medium for 30 min at 37° C.

7.4. Immunofluorescence and Confocal Microscopy.

Immunostaining procedure was as described in (Viaud, J. et al. Structure-based discovery of an inhibitor of Arf activation by Sec7 domains through targeting of protein-protein complexes. *Proc Natl Acad Sci USA* 104, 10370-5 (2007)) except that secondary antibody incubation was performed for 1h using Alexa 488-conjugated goat anti-mouse (1:600) or donkey anti-sheep (1:500) IgG and Alexa 647-conjugated phalloidin (1:100). Anti-GM130 was used at dilution 1:200. Images were bidirectionally recorded using an inverted Leica TCS SP8 laser-scanning confocal microscope with a 100× (N. A. 1.40) oil objective (HCX APO, Leica). Fluorochromes were detected sequentially using excitation laser lines at 488 nm (Alexa 488), 594 nm (mCherry) and 633 nm (Alexa 647). Stacks were generated using a z-step of 0.5 μm and processed using Fiji/ImageJ (Schindelin, J. et al. Fiji: an open-source platform for biological-image analysis. Nat Methods 9, 676-82 (2012)). Images are representative of at least two independent experiments.

7.5. siRNA Knockdown.

Gene silencing was achieved using siRNAs targeting all the known transcript variants of each GEF gene: siBRAG2, Hs_IQSEC1_5 (Qiagen, SI03019408); siARNO, Hs_P-SCD2_3 (Qiagen, SI00061299); siGBF1, Hs_GBF1_3 (Qiagen, SI00425418). Nontargeting control siRNA: siCTRL, AllStars Negative Control siRNA (Qiagen, 1027280). Hela cells were submitted to a double reverse transfection using Lipofectamine® RNAiMAX (Invitrogen, 12323563) following the manufacturer's instructions. Briefly, trypsinized cells were seeded at 15,000 cells/cm$^2$ into the wells of a 12-well plate, each containing the transfection mix: 10 pmol siRNA and 3 μl Lipofectamine@ RNAiMAX in 200 μl Opti-MEM® for a final volume of 1 ml. 48 hours later, cells were replated and transfected again following the same protocol, in 6-well plates for RNA extraction (final volume 2.5 ml/well) and in 8-well Lab-Tek® glass slides for immunofluorescence staining (final volume 200 μl/well). Analyses were performed 48 hours after the second transfection. As determined by RT-qPCR, BRAG2, ARNO and GBF1 mRNA levels were specifically decreased by about 50%, 83% and 88% in the presence of their respective siRNAs (FIG. 17) and these levels were not modified by treatment with Bragsin (FIG. 18). Total RNA was extracted with the RNeasy® Mini Kit (Qiagen, 74104) following the manufacturer's instructions. Each sample RNA (1 μg) was reverse-transcribed using the iScript™ Reverse Transcription Supermix for RT-qPCR (Bio-Rad, 170-8840). cDNAs (100 ng) were quantified by real-time PCR in a CFX Connect instrument (Bio-Rad) using the SsoAdvanced™ Universal SYBR® Green Supermix (Bio-Rad, 172-5270). Amplification was performed according to the Bio-Rad standard Prime-PCR protocol. Primers were chosen with the NCBI Primer-BLAST algorithm as follows: BRAG2,

```
                                    (SEQ ID NO: 2)
    5'-CGTGGCATTTCTTTGGTGTC-3' and (SEQ ID NO: 3)
    5'-ACCCGAGAATTGATGAGTCG-3';

(SEQ ID NO: 4)
    ARNO, 5'-TTGTGTCAAGGATAGGGCTG-3' and (SEQ ID NO: 5)
    5'-ACTTCACCTTCATAGAGGCG-3';

(SEQ ID NO: 6)
    GBF1, 5'-TGTCACTCTCTACCTTTGCG-3' and (SEQ ID NO: 7)
    5'-AAATCTCCGCTGTGTCCATC-3';

(SEQ ID NO: 8)
    GAPDH, 5'-ACAAGAGGAAGAGAGAGACCC-3' and (SEQ ID NO: 9)
    5'-TACATGACAAGGTGCGGCTC-3'
```

7.6. Proteins.

Bovine Δ17Arf1 and human Δ13Arf6, full-length myristoylated Arf1 and Arf6, human BRAG2$^{Sec7}$ (390-594) and BRAG2$^{Sec7PH}$ (390-811), human EFA6$^{Sec7}$ (527-727) and EFA6$^{Sec7PHCt}$ (527-1024), ARNO$^{Sec7}$ (50-256), BIG1$^{Sec7}$ (691-889), BIG1$^{DcbHusSec7}$ (2-888) and ARNO$^{Sec7PH}$ (50-399) were expressed and purified as in (Benabdi, S. et al. Family-wide Analysis of the Inhibition of Arf Guanine Nucleotide Exchange Factors with Small Molecules: Evidence of Unique Inhibitory Profiles. *Biochemistry* 56, 5125-5133 (2017)) and references therein. BRAG2$^{Sec7PH}$ mutants were purified as the wild type protein. Purification of human full-length Rac1 carrying a 6xHis tag in C-terminus and human TRIO$^{DH1PH1}$ (1232-1550) was described in (Peurois, F. et al. Characterization of the activation of small GTPases by their GEFs on membranes using artificial membrane tethering. *Biochem J* 474, 1259-1272 (2017)).

7.7. Liposomes and Flotation Assay.

Lipids (of natural origin) were from Avanti Polar Lipids, except NBD-PE from Sigma. Liposomes were prepared as described in (Aizel, K. et al. Integrated conformational and lipid-sensing regulation of endosomal ArfGEF BRAG2. *PLOS Biol* 11, e1001652 (2013)) and extruded at 0.2 μm. For the Arf GEF specificity studies, liposomes contained 48% phosphatidylcholine (PC), 20% phosphatidylethanolamine (PE), 30% phosphatidylserine (PS) and 2% phosphatidylinositol-4,5-bisphosphate (PIP$_2$). For Rac activation assay, liposomes contained 43% PC, 20% PE, 10% PS, 20% cholesterol, 2% PIP$_2$, 5% NiNTA lipids and 0.2% NBD-PE. To exclude aggregation or disruption of the liposomes, their size distribution was controlled before and after experiments by dynamic light scattering as described in (Benabdi, S. et al. *Biochemistry* 56, 5125-5133 (2017)). Dose-response and flotation assays were carried out with liposomes containing 37.9% PC, 20% PE, 20% PS, 2% PIP$_2$, 20% cholesterol and 0.1% NBD-PE. Flotation assays were carried out as in 18.

7.8. Nucleotide Exchange Assays.

Nucleotide exchange kinetics were monitored by tryptophan fluorescence with excitation/emission wavelengths of 292/340 nm using a Cary Eclipse fluorimeter (Varian) at 37° C. and under continuous stirring as described in [50,51]. For specificity assays, 50 μM of Bragsin1 or 0.25% DMSO were incubated for 2 min at 37° C. in HKM buffer (50 mM HEPES pH 7.4, 120 mM potassium acetate, 1 mM MgCl$_2$ and 1 mM DTT) with either 1 μM of N-terminally truncated Arf-GDP and 100 nM of indicated Sec7 domain (in solution) or 0.4 μM of $^{myr}$Arf1 in the presence of 100 μM of liposomes and 2 to 100 nM of ArfGEFs as described in (Benabdi, S. et al. *Biochemistry* 56, 5125-5133 (2017) and Peurois, F. et al. *Biochem J* 474, 1259-1272 (2017). Nucleotide exchange rates (k$_{obs}$) were determined from monoexponential fits and means are given as the percentage of control activity±SD. All experiments were done in triplicate.

7.9. Crystallization and Structure Determination.

BRAG2 was concentrated to 5 mg/ml for crystallization and crystals were obtained at 293 K by vapor diffusion in 18% PEG 20000, 0.1 M Tris-HCl pH 8.5. Crystals were transferred to the reservoir solution supplemented with 10% glycerol and soaked with 20 μM Bragsin1 in a final volume of 100 μl and incubated for 24 hours at room temperature. Diffraction data were collected at PROXIMA2 beamline (SOLEIL Synchrotron, Gif-sur-Yvette, France) from a single crystal and processed with autoPROC (Vonrhein, C. et al. Data processing and analysis with the autoPROC toolbox. *Acta Crystallogr D Biol Crystallogr* 67, 293-302 (2011)). The structure was solved by molecular replacement with Phaser (McCoy, A. J. et al. Phaser crystallographic software. *J Appl Crystallogr* 40, 658-674 (2007)) using unbound BRAG2 (PDB 5NLY) (Karandur, D. et al., *J. Proc Natl Acad Sci USA* 114, 11416-11421 (2017)) as a model. The ligand fit was done using RHOFIT (Global Phasing Ltd.) or the ligand fit option in Phenix, which both gave the same ligand orientation. The structure was refined with Phenix (Adams, P. D. et al. PHENIX: a comprehensive Python-based system for macromolecular structure solution. *Acta Crystallogr D Biol Crystallogr* 66, 213-21 (2010)) and Buster (Blanc, E. et al. Refinement of severely incomplete structures with maximum likelihood in BUSTER-TNT. *Acta Crystallogr D Biol Crystallogr* 60, 2210-21 (2004)), in alternation with model building in Coot (Emsley, P. & Cowtan, K. Coot: model-building tools for molecular graphics. *Acta crystallographica. Section D, Biological crystallography* 60, 2126-32 (2004)). Statistics for data processing and refinement are reported in Table 1. Coordinates and structure factors have been deposited to the Protein Data Bank with entry code 6FNE.

7.10. Cancer Stem Cell Assays

Three breast cancer cell lines (BCL) from three distinct molecular subtypes (SUM149/basal, SUM159/mesenchymal and S68/luminal) were used in this study. All BCLs were grown in standard medium as previously described (Charafe-Jauffret, E. et al. *Cancer Res* 73, 7290-300 (2013)). The ALDEFLUOR Kit (Stem Cell Technologies) was used to isolate the population with high aldehyde dehydrogenase enzymatic activity using an LSR2 cytometer (Becton-Dickinson Biosciences) as previously described (Ginestier, C. et al. *Cell Stem Cell* 1, 555-67 (2007)). For the tumorsphere assay, BCLs were grown in adherent condition under Bragsin2 treatment (50 mM) or vehicle for 72 hours, then seeded as single cells in ultra-low attachment plates (Corning) following a limiting dilution. Tumorspheres were grown in a serum-free mammary epithelium basal medium. The capacity of cells to form tumorspheres was quantified under microscope. Statistical analysis of tumorsphere-forming efficiency was done with Extreme LDA software (http://bioinf.wehi.edu.au/software/elda/).

Conclusions of Examples

In the present invention, Bragsin has been identified as a potent and selective inhibitor of BRAG2 that affects breast cancer stem cells in view of reconstitution of lipidated Arf GTPases and GEFs on artificial membranes together with cell-based assays. The mechanism of inhibition was supported by crystallography, mutagenesis, SAR and membrane-binding assays. Inventors supporte by these experiments implications for the cell biology of BRAG2 and its role in breast cancer. Interfacial inhibition of protein-membrane interactions as a new concept in drug discovery was also established.

The characterization of Bragsin reveals a previously overlooked aspect of BRAG2 functions in controlling the integrity of the TGN compartment. Previous studies reported a general role of BRAG2 in regulating plasma membrane receptor signaling, such as AMPA, EGF, VEGF and GNAQ receptors and trafficking of adhesion proteins including b1-integrins and N-cadherin, but the underlying functional pathways have remained unclear. Interestingly, recent studies showed that b1-integrins use a retrograde route to the TGN to be secreted in a polarized manner leading to cell adhesion or persistent migration, and that recycling b1-integrins transiently localize to TGN46-positive post-Golgi carriers. The conspicuous effect of Bragsin on the structure of the TGN suggest a role of BRAG2 in regulating main aspects of the traffic of b1-integrins and other receptors to and from the TGN.

Bragsin involves a unique mechanism of action at the protein-membrane interface. Bragsin binds at the edge of the canonical lipid-binding site of the PH domain without disrupting the interaction of BRAG2 with the liposomes. It is thus likely that Bragsin is able to contact BRAG2 and the membrane simultaneously.

$PIP_2$-containing membranes potentiate the GEF activity of BRAG2 as highlighted by previous studies (Aizel, K. et al. Integrated conformational and lipid-sensing regulation of endosomal ArfGEF BRAG2. *PLOS Biol* 11, e1001652 (2013); Jian, X., Gruschus, J. M., Sztul, E. & Randazzo, P. A. The pleckstrin homology (PH) domain of the Arf exchange factor Brag2 is an allosteric binding site. *J Biol Chem* 287, 24273-83 (2012). This involves contacts with multiple lipids leading to a well-defined apposition of the Arf-BRAG2 complex on the membrane (Karandur, D., Nawrotek, A., Kuriyan, J. & Cherfils, J. Multiple interactions between an Arf/GEF complex and charged lipids determine activation kinetics on the membrane. *Proc Natl Acad Sci USA* 114, 11416-11421 (2017)). It can be predicted that mispositioning of BRAG2 on the membrane should affect its efficiency. The biophysical and structural data reported in the present invention robustly suggest that this is the mechanism whereby Bragsin inhibits BRAG2, as summarized in the model shown in FIG. 6. Given that Bragsin targets a PH domain, which is widespread in signaling peripheral membrane proteins (Lemmon, M. A. Membrane recognition by phospholipid-binding domains. *Nat Rev Mol Cell Biol* 9, 99-111 (2008)), it is remarkable and surprising that it did not inhibit the exchange activity of the ArfGEFs ARNO and EFA6 and of the RacGEF Trio, all of which also carry PH domains that bind to the plasma membrane. Such selectivity is supported by the mounting evidence that lipid cooperativity and/or recognition of several types of phosphoinositides is a common principle for the specific membrane recruitment of many PH domains and other peripheral membrane-binding domains. As a consequence, the collective physico-chemical properties of a lipid bilayer encode specificity determinants that are recognized by peripheral membrane proteins in addition to, or in place of, a particular interaction with an individual lipid, leading to unique protein-membrane interfaces. Accordingly, the specificity of Bragsin likely results from its interfacial mechanism, whereby it recognizes BRAG2 in the context of its unique interface with the lipid bilayer.

Membrane peripheral proteins constitute a large class of signaling proteins that control vital cellular processes, yet the "peripherome" is still considered poorly druggable according to the prior art. Targeting the interactions of peripheral membrane proteins with membranes exemplifies an emerging paradigm shift in drug development, where focus has traditionally rather been on the inhibition of catalytic activities and protein-protein interactions, notably in cancer. Bragsin represents an entirely novel class of inhibitors, which exploit the protein-membrane interface for efficient inhibition. This mode of inhibition is reminiscent of interfacial inhibitors of protein-protein interactions to some extent, such as the natural compound Brefeldin A, which traps another subfamily of ArfGEFs in a non-productive complex with the small GTPase Arf1, and a growing list of protein-protein stabilizers that work according to the same principle. The present invention demonstrates that the protein-membrane interface is a novel Achille's heel in peripheral membrane proteins owing to specificity determinants and energetic features that can be exploited by small molecules for inhibition. As illustrated by inventor's observation, Bragsin affects the stemness of breast cancer cells.

The present invention has characterized novel inhibitors that exploit protein-membrane interactions. The present invention represents an exquisite tool to dissect pathways reliant on BRAG2 involved in receptor signaling and cancer. The present invention also defines a novel concept that can apply to a broad range of peripheral membrane signaling proteins and opens avenues for drug development based on the mechanisms described in this study.

TABLE 1

Crystal structure of Brag2/Bragsin1 complex. Crystallographic statistics.

| X-ray source | Proxima 2, synchrotron SOLEIL |
|---|---|
| Data collection: | |
| Space group | P2₁2₁2₁ |
| Cell dimensions | |
| a, b, c (Å) | 65.92, 66.16, 218.79 |
| a, b, g (°) | 90, 90, 90 |
| Wavelength (Å) | 0.980105 |
| Resolution (Å) | 65.9-2.50 (2.78-2.50) |
| $R_{sym}$ (%) | 18 (142) |
| $R_{pim}$ (%) | 5 (46) |
| Completeness (%) | 93.9 (70) |
| Redundancy | 13.0 (10.5) |
| I/s | 9.9 (1.7) |
| CC(1/2) (%) | 99.7 (54) |
| Total number of reflection | 286171 (11487) |
| Refinement: | |
| $R_{work}/R_{free}$ | 0.22/0.27 |
| Nb. Atoms | |
| Protein | 5641 |
| Water | 18 |
| B-factors | |
| Protein | 66 |
| Bragsin1 | 74 |
| Water | 43 |
| R.M.S. deviations | |
| Bond lengths (Å) | 0.009 |
| Bond angles (°) | 1.136 |
| PDB ID | 6FNE |

Human BRAG2 (IQ motif and SEC7 domain-containing protein 1) has the following sequence: (https://www.uniprot.org/uniprot/Q6DN90.fasta)
>sp|Q6DN90|IQEC1_HUMAN IQ motif and SEC7 domain-containing protein 1 OS=Homo sapiens OX=9606 GN=IQSEC1 PE=1 SV=1

MWCLHCNSERTQSLLELELDSGVEGEAPSSETGTSLDSPSAYPQGPLVP
GSSLSPDHYEHTSVGAYGLYSGPPGQQQRTRRPKLQHSTSILRKQAEEE
AIKRSRSLSESYELSSDLQDKQVEMLERKYGGRLVTRHAARTIQTAFRQ
YQMNKNFERLRSSMSENRMSRRIVLSNMRMQFSFEGPEKVHSSYFEGKQ
VSVTNDGSQLGALVSPECGDLSEPTTLKSPAPSSDFADAITELEDAFSR
QVKSLAESIDDALNCRSLHTEEAPALDAARARDTEPQTALHGMDHRKLD
EMTASYSDVTLYIDEEELSPPLPLSQAGDRPSSTESDLRLRAGGAAPDY
WALAHKEDKADTDTSCRSTPSLERQEQRLRVEHLPLLTIEPPSDSSVDL
SDRSERGSLKRQSAYERSLGGQQGSPKHGPHSGAPKSLPREEPELRPRP
PRPLDSHLAINGSANRQSKSESDYSDGDNDSINSTSNSNDTINCSSESS
SRDSLREQTLSKQTYHKEARNSWDSPAFSNDVIRKRHYRIGLNLFNKKP
EKGVQYLIERGFVPDTPVGVAHFLLQRKGLSRQMIGEFLGNRQKQFNRD
VLDCVVDEMDFSTMELDEALRKFQAHIRVQGEAQKVERLIEAFSQRYCI
CNPGVVRQFRNPDTIFILAFAIILLNTDMYSPNVKPERKMKLEDFIKNL
RGVDDGEDIPREMLMGIYERIRKRELKTNEDHVSQVQKVEKLIVGKKPI
GSLHPGLGCVLSLPHRRLVCYCRLFEVPDPNKPQKLGLHQREIFLFNDL
LVVTKIFQKKKNSVTYSFRQSFSLYGMQVLLFENQYYPNGIRLTSSVPG
ADIKVLINFNAPNPQDRKKFTDDLRESIAEVQEMEKHRIESELEKQKGV
VRPSMSQCSSLKKESGNGTLSRACLDDSYASGEGLKRSALSSSLRDLSE
AGKRGRRSSAGSLESNVEFQPFEPLQPSVLCS

Human IQ motif and SEC7 domain-containing protein 1 is also known with the following sequence:
(https://www.uniprot.org/uniprot/A0A087WWK8.fasta):
>tr|A0A087WWK8|A0A087WWK8_HUMAN IQ motif and SEC7 domain-containing protein 1 OS=Homo sapiens OX=9606 GN=IQSEC1 PE=1 SV=1

MACRRRYFVEGEAPSSETGTSLDSPSAYPQGPLVPGSSLSPDHYEHTSV
GAYGLYSGPPGQQQRTRRPKLQHSTSILRKQAEEEAIKRSRSLSESYEL
SSDLQDKQVEMLERKYGGRLVTRHAARTIQTAFRQYQMNKNFERLRSSM
SENRMSRRIVLSNMRMQFSFEGPEKVHSSYFEGKQVSVTNDGSQLGALV
SPECGDLSEPTTLKSPAPSSDFADAITELEDAFSRQVKSLAESIDDALN
CRSLHTEEAPALDAARARDTEPQTALHGMDHRKLDEMTASYSDVTLYID
EEELSPPLPLSQAGDRPSSTESDLRLRAGGAAPDYWALAHKEDKADTDT
SCRSTPSLERQEQRLRVEHLPLLTIEPPSDSSVDLSDRSERGSLKRQSA
YERSLGGQQGSPKHGPHSGAPKSLPREEPELRPRPPRPLDSHLAINGSA
NRQSKSESDYSDGDNDSINSTSNSNDTINCSSESSSRDSLREQTLSKQT
YHKEARNSWDSPAFSNDVIRKRHYRIGLNLFNKKPEKGVQYLIERGFVP
DTPVGVAHFLLQRKGLSRQMIGEFLGNRQKQFNRDVLDCVVDEMDFSTM
ELDEALRKFQAHIRVQGEAQKVERLIEAFSQRYCICNPGVVRQFRNPDT
IFILAFAIILLNTDMYSPNVKPERKMKLEDFIKNLRGVDDGEDIPREML
MGIYERIRKRELKTNEDHVSQVQKVEKLIVGKKPIGSLHPGLGCVLSLP
HRRLVCYCRLFEVPDPNKPQKLGLHQREIFLFNDLLVVTKIFQKKKNSV
TYSFRQSFSLYGMQVLLFENQYYPNGIRLTSSVPGADIKVLINFNAPNP
QDRKKFTDDLRESIAEVQEMEKHRIESELEKQKGVVRPSMSQCSSLKKE
SGNGTLSRACLDDSYASGEGLKRSALSSSLRDLSEAGKRGRRSSAGSLE
SNVEGSIISSPHMRRRATSTRECPSRPHQTMPNSSSLLGSLFGSKRGKP
PPQAHLPSAPALPPPHPPVVLPHLQHSVAGHHLGPPEGLPQAAMHGHHT
QYCHMQNPPPYHHHHHHHPPQHIQHAHQYHHGPHGGHPAYGAHAHGHPP
LPSAHVGHTVHHHGQPPAPPPPTSSKAKPSGISTIVSAHVGHTVHHHGQ
PPAPPPPTSSKAKPSGISTIV

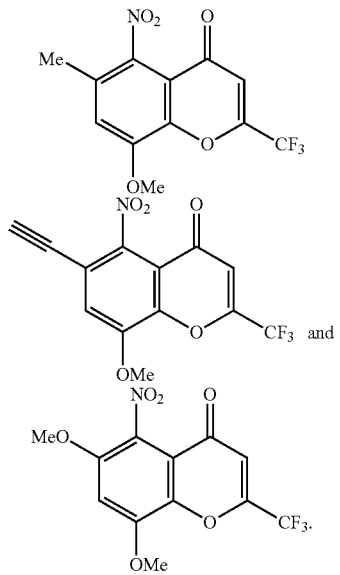

The invention claimed is:

1. A method of treating a cancer or pathogenic angiogenesis in a subject in need thereof, comprising the step of administering a therapeutically effective amount of a pharmaceutical composition comprising an inhibitor of a mammalian brefeldin-resistant Arf-GEF 2 protein (BRAG2) having the chemical structure (I):

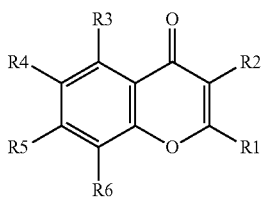

(I)

wherein:
R1 is a fluorinated alkyl;
R2 is hydrogen,
R3 is $NO_2$; and
R4, R5 and R6 are independently atoms or groups of atoms selected from the group consisting of an hydrogen, an hydroxy, an alkyl, an O-alkyl (or alkoxy), an alkene, an O-alkylene, an alkyne, and an O-alkyne.

2. The method of claim 1, wherein said inhibitor is:

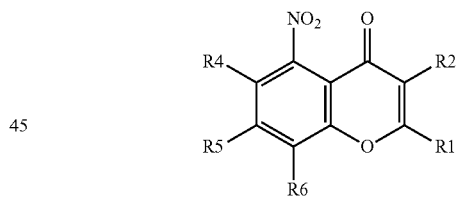

wherein R' is a chemical group of atoms and R2, R4, R5 and R6 are as defined in claim 1.

3. The method of claim 1, wherein at least one of R4, R5 and R6 is independently an alkyl or alkoxy group substituted by a substituent selected from the group consisting of halogen; alkyl; alkenyl; alkynyl; hydroxy; alkoxy; nitro; thiol; thioether; imine; cyano; amido; phosphonato; phosphine; carboxyl; thiocarbonyl; sulfonyl; sulfonamide; ketone; aldehyde; ester; oxygen (—O); haloalkyl; trifluoromethyl; monocyclic cycloalkyl, fused or non-fused polycyclic cycloalkyl; monocyclic heterocycloalkyl; fused or non-fused polycyclic heterocycloalkyl, monocyclic aryl; fused or non-fused polycyclic aryl; monocyclic heteroaryl; fused or non-fused polycyclic heteroaryl; primary amino; secondary amino; tertiary amino; —CO2CH3; CONH2; OCH2CONH2; NH2; $SO_2NH2$; OCHF2; and CF3; OCF3.

4. The method of claim 1, wherein R2, R5 and R6 are hydrogen atoms.

5. The method of claim 1, wherein said inhibitor is selected from the group consisting of:

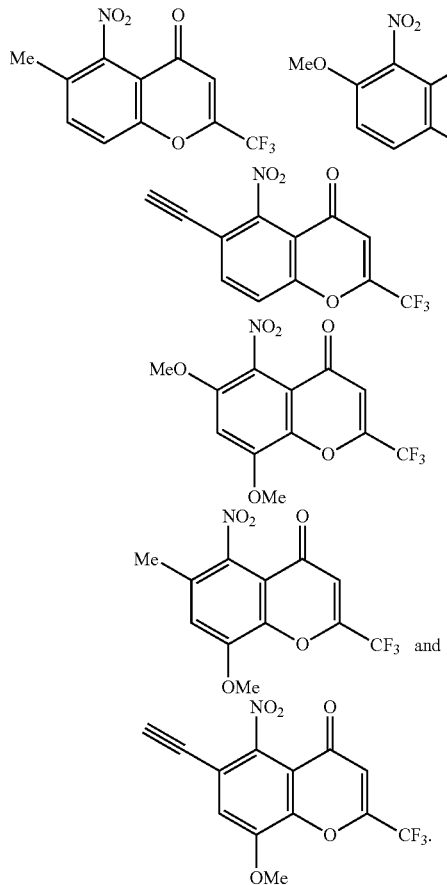

6. An inhibitor of a mammalian brefeldin-resistant Arf-GEF 2 protein (BRAG2) having the following chemical structure (I):

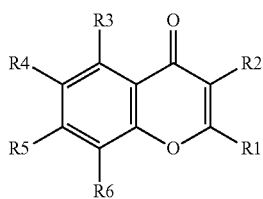

wherein:

R1 is a fluorinated alkyl;

R2 is hydrogen,

R3 is NO$_2$; and

R4, R5 and R6 are independently atoms or groups of atoms selected from the group consisting of an hydrogen, an hydroxy, an alkyl, an O-alkyl (or alkoxy), an alkene, an O-alkylene, an alkyne, and an O-alkyne, and wherein said inhibitor is selected from the group consisting of:

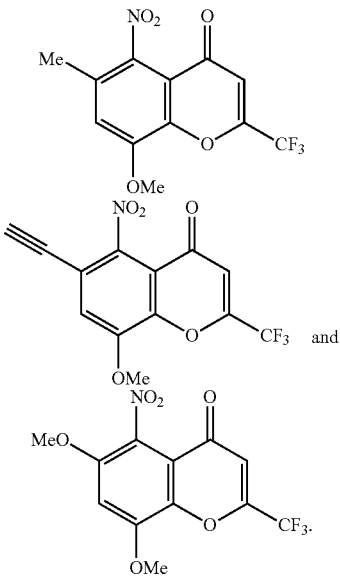

7. The method of claim 1, wherein said pharmaceutical composition further comprises one or more excipients and optionally one other pharmaceutically active ingredient.

8. A method of therapeutic treatment, said method comprising administering to a mammal in need thereof an effective amount of at least one inhibitor of mammalian BRAG2 selected from the group according to claim 6.

9. The method of claim 8, wherein said method is for treating a disease presenting a deregulated expression of brefeldin-resistant Arf-GEF 2 protein (BRAG2), wherein the disease is selected from the group consisting of a cancer, pathological angiogenesis and diabetic retinopathy.

10. The method of claim 8, wherein said method is for treating a disease selected from the group consisting of a cancer, an invasive cancer, a cancer with metastasis, a cancer resistant to an EGFR and/or ErbB2 modulator, pathological angiogenesis and diabetic retinopathy.

11. The method of claim 8, wherein said molecule is an inhibitor binding at an interface between the BRAG2 and a lipid bilayer having one or more protein-membrane interactions and inhibiting the BRAG2, and wherein said method is for treatment of a cancer.

12. The method according to claim 1, wherein
the alkyl is methyl (Me) or ethyl (Et); and/or
the O-alkyl is OMe or OEt; and/or
the alkyne, is —CCH; and/or
the O-alkyne is —OCH2-CCH.

13. The method of claim 1, wherein R2 is hydrogen and wherein R4, R5 and R6 substituents are independently and optionally further substituted with a substituent selected from the group consisting of an alkyl, an alkenyl, an alkynyl, an cycloalkyl, an cycloalkenyl, a heterocycloalkyl, an aryl, a heteroaryl, an aralkyl, a heteraralkyl, a haloalkyl, —C(O)NR11R12, —NR13C(O)R14, a halo, —OR13, cyano, nitro and a haloalkoxy.

14. The method of claim 1, wherein R2 is hydrogen and wherein R4, R5 and R6 substituents are independently and optionally further substituted with a substituent selected from the group consisting of —C(O)R13, —NR11R12, —SR13, —C(O)OR13, —OC(O)R13, —NR13C(O) NR11R12, —OC(O)NR11R12, —NR13C(O)OR14, —S(O) rR13, —NR13S(O)rR14, —OS(O)rR14, S(O)rNR11R12, —O, —S, and —N—R13, wherein r is 1 or 2;

R13 and R14 for each occurrence are, independently, selected from the group consisting of H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, and an optionally substituted heteraralkyl; and R11 and R12, for each occurrence are, independently, selected from the group consisting of H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, and an optionally substituted heteraralkyl; or R11 and R12 taken together with the nitrogen to which they are attached is optionally substituted heterocycloalkyl or optionally substituted heteroaryl.

15. The method of claim 5, wherein said molecule is selected from the group consisting of: